(12) United States Patent
Shyu et al.

(10) Patent No.: US 11,458,171 B2
(45) Date of Patent: Oct. 4, 2022

(54) ENGINEERING STEM CELLS FOR CANCER THERAPY

(71) Applicant: CHINA MEDICAL UNIVERSITY, Taichung (TW)

(72) Inventors: Woei-Cherng Shyu, Taichung (TW); Chen-Huan Lin, Taichung (TW); Wei Lee, Taipei (TW); Chien-Lin Chen, New Taipei (TW); Long-Bin Jeng, Taichung (TW); Chang-Hai Tsai, Taichung (TW)

(73) Assignee: CHINA MEDICAL UNIVERSITY, Taichung (TW)

(*) Notice: Subject to any disclaimer, the term of this patent is extended or adjusted under 35 U.S.C. 154(b) by 539 days.

(21) Appl. No.: 16/356,463

(22) Filed: Mar. 18, 2019

(65) Prior Publication Data

US 2020/0061119 A1 Feb. 27, 2020

Related U.S. Application Data

(60) Provisional application No. 62/646,014, filed on Mar. 21, 2018.

(51) Int. Cl.
| | | |
|---|---|---|
| *A61K 35/28* | (2015.01) | |
| *A61P 35/00* | (2006.01) | |
| *C07K 14/705* | (2006.01) | |
| *C12N 5/0775* | (2010.01) | |
| *C12N 9/12* | (2006.01) | |

(52) U.S. Cl.
CPC .............. *A61K 35/28* (2013.01); *A61P 35/00* (2018.01); *C07K 14/70521* (2013.01); *C07K 14/70575* (2013.01); *C12N 5/0668* (2013.01); *C12N 9/1211* (2013.01); *C12Y 207/01021* (2013.01)

(58) Field of Classification Search
CPC . A61P 35/00; A61K 2300/00; C12N 2510/00; C12N 9/1211
See application file for complete search history.

(56) References Cited

U.S. PATENT DOCUMENTS

| | | | |
|---|---|---|---|
| 2014/0369979 | A1 | 12/2014 | Sung et al. |
| 2018/0214544 | A1 | 8/2018 | Mitchell et al. |

FOREIGN PATENT DOCUMENTS

| | | |
|---|---|---|
| DE | 102006020307 A1 | 11/2007 |
| WO | WO-2017135800 A1 | 8/2017 |

OTHER PUBLICATIONS

Kim et al. 2013; Complete regression of metastatic renal cell carcinoma by multiple injections of engineered mesenchymal stem cells expressing dodecameric TRAIL and HSV-TK. Clin. Cancer Res. 19(2): 415-427.*
Hendriks et al. 2016; Programmed death ligand 1 (PD-L1) targeted TRAIL combines PD-I1 mediated checkpoint inhibition with TRAIL mediated apoptosis induction. Oncoimmunology. 5(8): 1-13.*
Corsello, Salvatore Maria, et al. "Endocrine side effects induced by immune checkpoint inhibitors." The Journal of Clinical Endocrinology & Metabolism 98.4 (2013): 1361-1375.
Johnstone, Ricky W., Ailsa J. Frew, and Mark J. Smyth. "The TRAIL apoptotic pathway in cancer onset, progression and therapy." Nature Reviews Cancer 8.10 (2008): 782-798.
Ashkenazi, Avi, and Vishva M. Dixit. "Death receptors: signaling and modulation." Science 281.5381 (1998): 1305-1308.
Duiker, E. W., et al. "The clinical trail of TRAIL." European Journal of Cancer 42.14 (2006): 2233-2240.
Zuk, Patricia A., et al. "Human adipose tissue is a source of multipotent stem cells." Molecular Biology of the Cell 13.12 (2002): 4279-4295.
Casucci M, Bondanza A. "Suicide Gene Therapy to Increase the Safety of Chimeric Antigen Receptor-Redirected T Lymphocytes" J Cancer 2011; 2:378-382.
Iwao, Keiichiro, et al. "Heparan sulfate deficiency leads to Peters anomaly in mice by disturbing neural crest TGF-β2 signaling." The Journal of Clinical Investigation 119.7 (2009): 1997-2008.
Lee, Shin-Da, et al. "Role of stress-inducible protein-1 in recruitment of bone marrow derived cells into the ischemic brains." EMBO Molecular Medicine 5.8 (2013): 1227-1246.
Nöth, Ulrich, et al. "Multilineage mesenchymal differentiation potential of human trabecular bone-derived cells." Journal of Orthopaedic Research 20.5 (2002): 1060-1069.
Laczka-Osyczka, Anna, et al. "Behavior of bone marrow cells cultured on three different coatings of gel-derived bioactive glassceramics at early stages of cell differentiation." Journal of Biomedical Materials Research: An Official Journal of The Society for Biomaterials, The Japanese Society for Biomaterials, and the Australian Society for Biomaterials 42.3 (1998): 433-442.
Rafii, Shahin, et al. "Vascular and haematopoietic stem cells: novel targets for anti-angiogenesis therapy?." Nature Reviews Cancer 2.11 (2002): 826-835.
Lin et al. "In Vitro Differentiation of Human Neural Progenitor Cells Into Striatal GABAergic Neurons" Stem Cells Transl Med. Jul. 2015;4(7):775-788.

(Continued)

*Primary Examiner* — Karen Cochrane Carlson
(74) *Attorney, Agent, or Firm* — Duane Morris LLP

(57) ABSTRACT

The present disclosure provides an engineered stem cell, comprising a vector comprising a polynucleotide comprising a nucleic acid sequence of suicide gene, a nucleic acid sequence of immune checkpoint gene and a natural cytotoxicity triggering receptor or a TNF-related apoptosis-inducing ligand, wherein the stem cell is a tumor-targeting cell. The present disclosure also provides a method for treating a cancer or enhancing intratumor immunity or enhancing immunity in tumor microenvironment in a subject, comprising administering an effective amount of the engineered stem cell of the present disclosure to the subject.

16 Claims, 52 Drawing Sheets
(30 of 52 Drawing Sheet(s) Filed in Color)
Specification includes a Sequence Listing.

(56) References Cited

OTHER PUBLICATIONS

Bain et al. "Resident and pro-inflammatory macrophages in the colon represent alternative context-dependent fates of the same Ly6Chi monocyte precursors" Mucosal Immunology vol. 6(3), pp. 498-510 (2013).

Quah, Ben JC, Hilary S. Warren, and Christopher R. Parish. "Monitoring lymphocyte proliferation in vitro and in vivo with the intracellular fluorescent dye carboxyfluorescein diacetate succinimidyl ester." Nature Protocols 2.9 (2007) 2049-2056.

Shinojima, Naoki, et al. "TGF-β Mediates Homing of Bone Marrow-Derived Human Mesenchymal Stem Cells to Glioma Stem Cells." Cancer Research 73.7 (2013): 2333 2344.

Björck, Pia. "Isolation and characterization of plasmacytoid dendritic cells from Flt3 ligand and granulocyte-macrophage colony-stimulating factor-treated mice." Blood 98.13 (2001): 3520-3526.

Asahara, Takayuki, et al. "Isolation of putative progenitor endothelial cells for angiogenesis." Science 275.5302 (1997): 964-967.

Yasuhara, Takao, et al. "Intravenous grafts recapitulate the neurorestoration afforded by intracerebrally delivered multipotent adult progenitor cells in neonatal hypoxic-ischemic rats." Journal of Cerebral Blood Flow & Metabolism 28.11 (2008): 1804-1810.

Barnett, et al."Single-cell imaging of retinal ganglion cell apoptosis with a cell-penetrating, activatable peptide probe in an in vivo glaucoma model" Proc. Natl. Acad. Sci. Jun. 9, 2009 106 (23) 9391-9396.

Gnanasammandhan, Muthu Kumara, et al. "Near-IR photoactivation using mesoporous silica-coated NaYF 4: Yb, Er/Tm upconversion nanoparticles " Nature Protocols 11.4 (2016): 688-713.

Chittaranjan, Suganthi, et al. "Steroid hormone control of cell death and cell survival: molecular insights using RNAi." PLoS Genetics 5.2 (2009): e 1000379, 17 pages.

Liu, Jing, et al. "Assessing immune-related adverse events of efficacious combination immunotherapies in preclinical models of cancer." Cancer Rsearch 76.18 (2016): 5288-5301.

D'Ippolito, Gianluca, et al. "Marrow-isolated adult multilineage inducible (MIAMI) cells, a unique population of postnatal young and old human cells with extensive expansion and differentiation potential." Journal of Cell Science 117.14 (2004): 2971-2981.

Okazaki, Taku, and Tasuku Honjo. "The PD-1-PD-L pathway in immunological tolerance." Trends in Immunology 27.4 (2006): 195-201.

Dong, et al. "PD-1 and its ligands are important immune checkpoints in cancer", Oncotarget, vol. 8, (No. 2), 2171-2186 (2017).

Loebinger, M et al., "Mesenchymal Stem Cell Delivery of TRAIL Can Eliminate Metastatic Cancer", *Cancer Res* 2009;69:4134-4142. Published Online First May 12, 2009.

Li et al., "Structure of the human activating natural cytotoxicity receptor NKp30 bound to its tumor cell ligand B7-H6", The Rockefeller University Press, J. Exp. Med. vol. 208 No. 4 703-714 (2011).

Extended European Search Report in EP Application No. 19771445.4, dated Nov. 30, 2021, in 14 pages.

\* cited by examiner

FIG. 1E-(a)
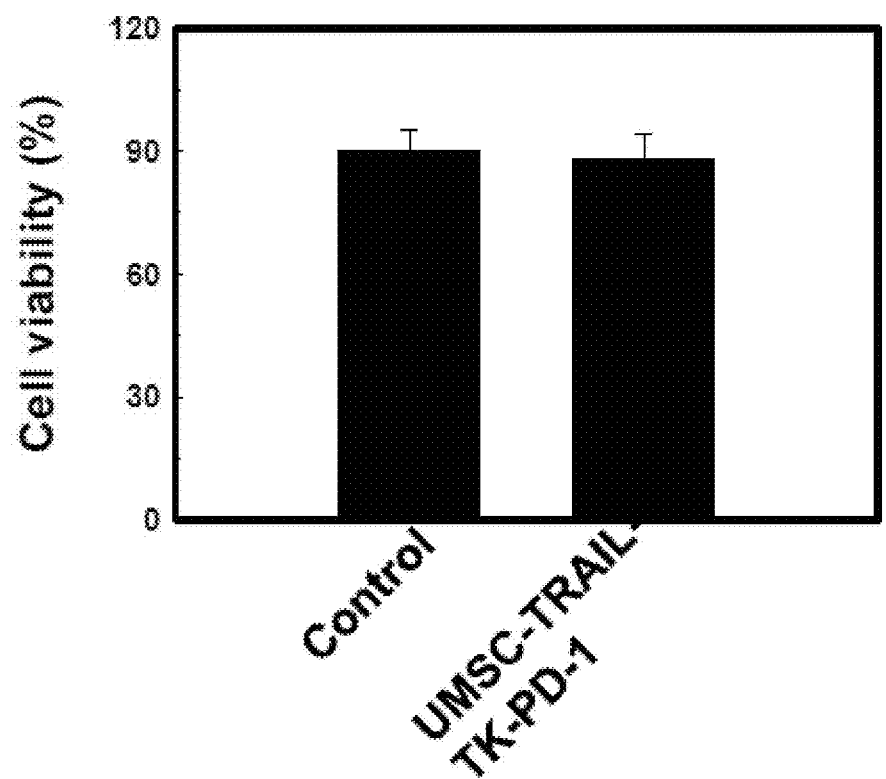

FIG. 1E-(b)
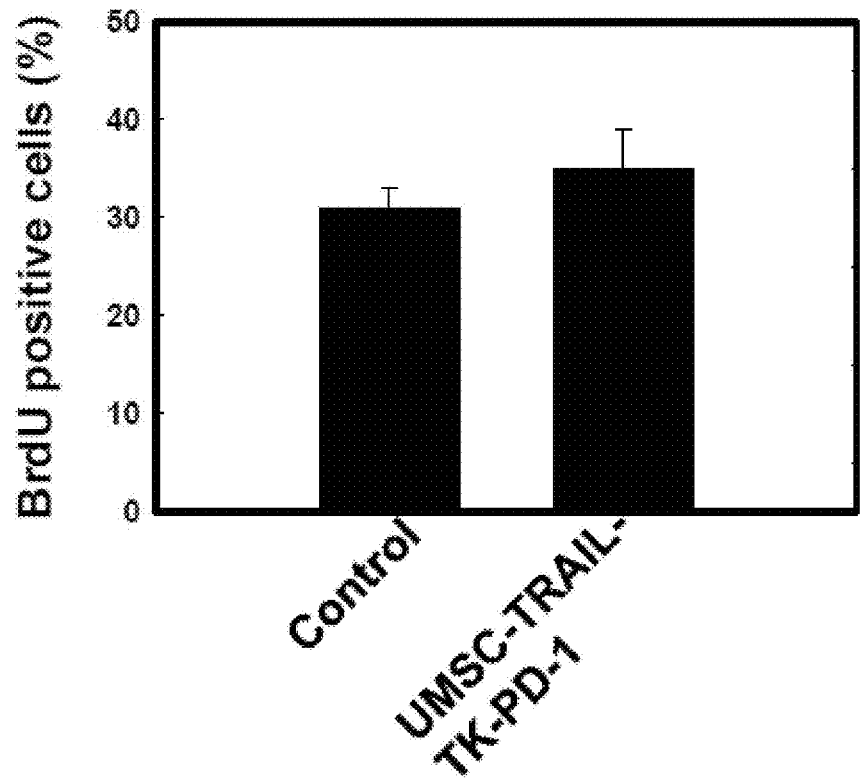
FIG. 1E-(c)
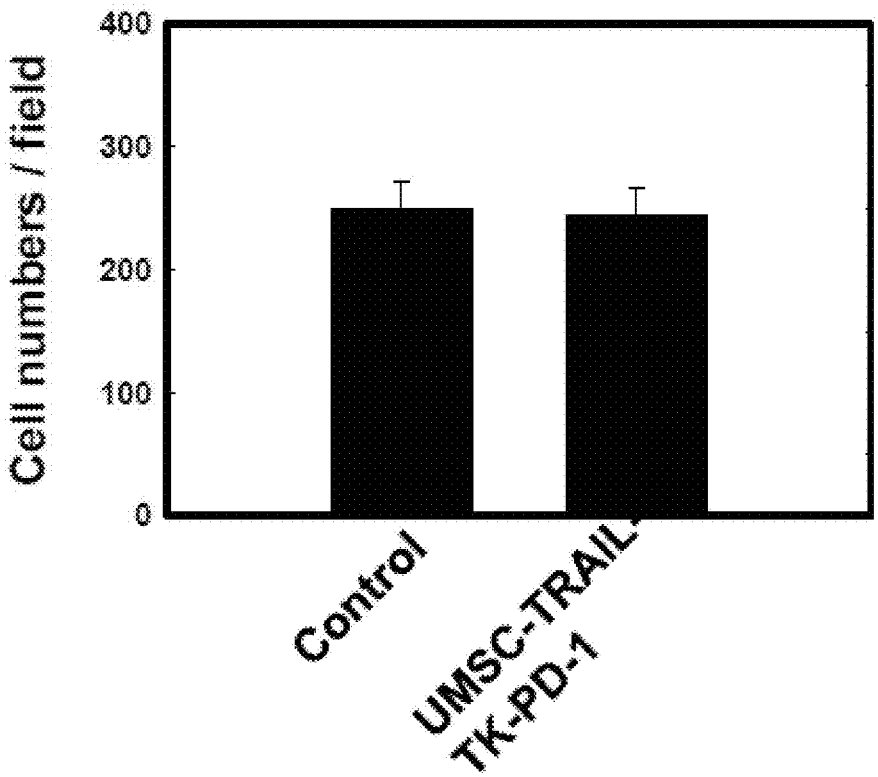

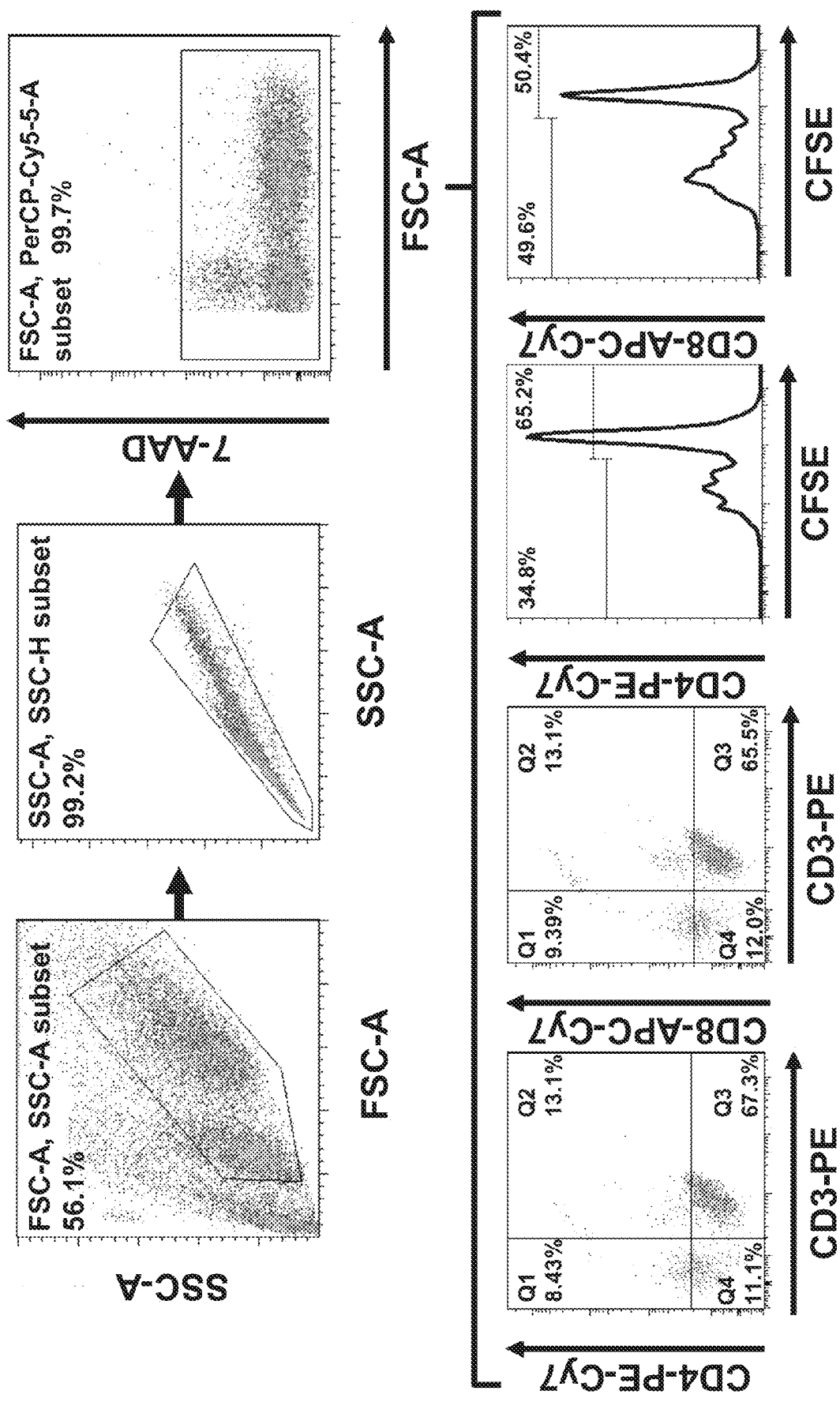
FIG. 2B-(a)

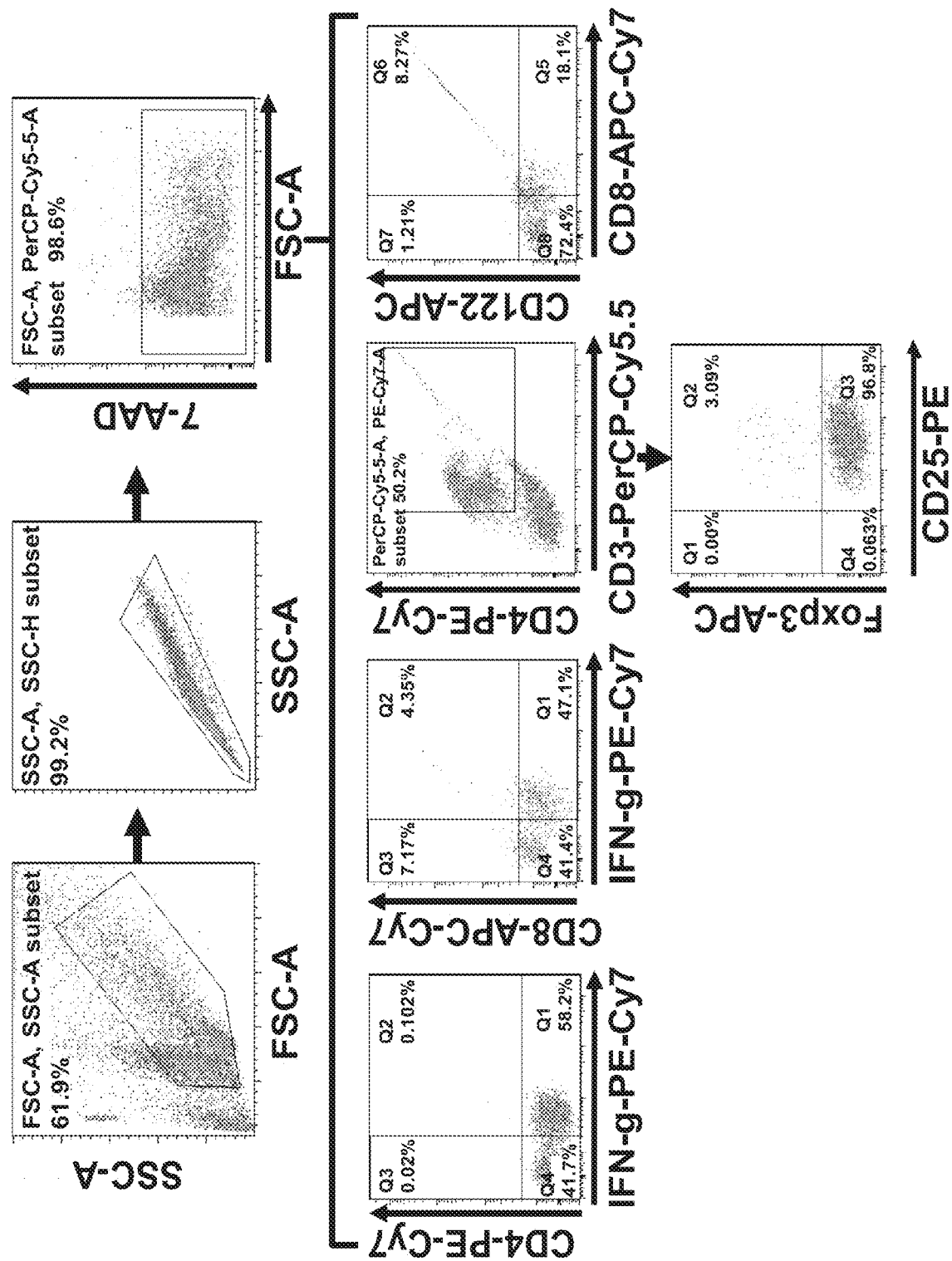
FIG. 2B-(b)

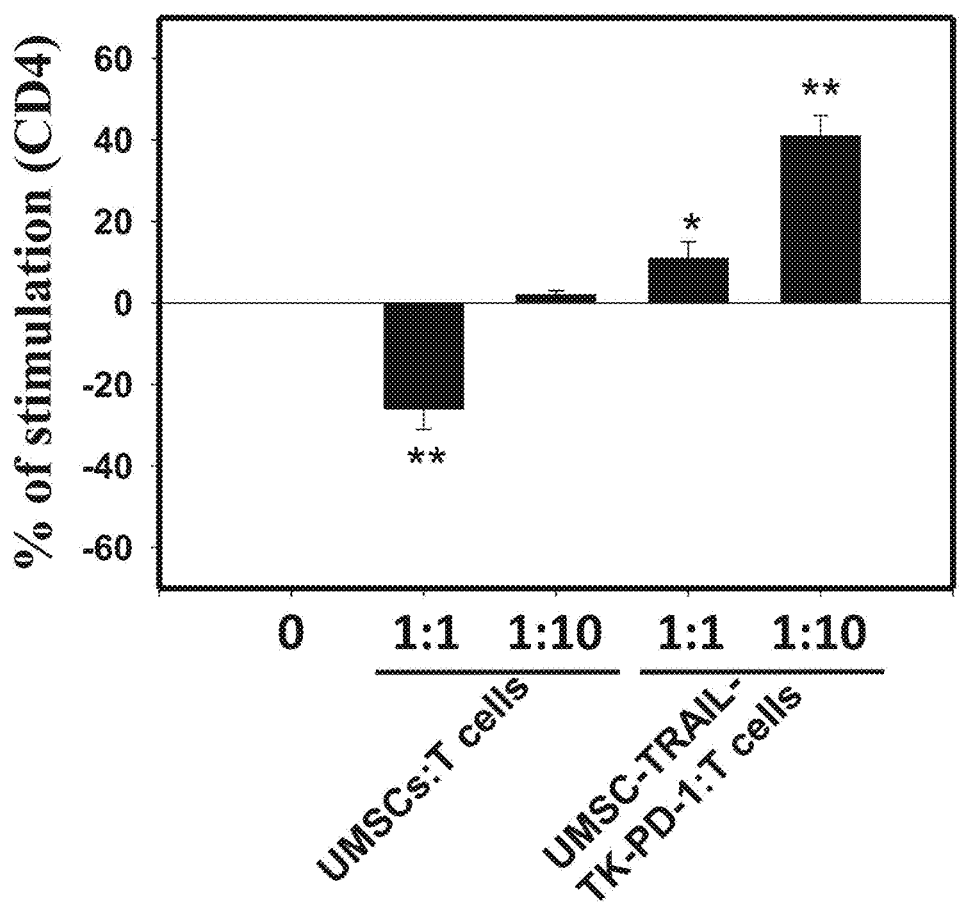
FIG. 2C-(a)

FIG. 2C-(b)
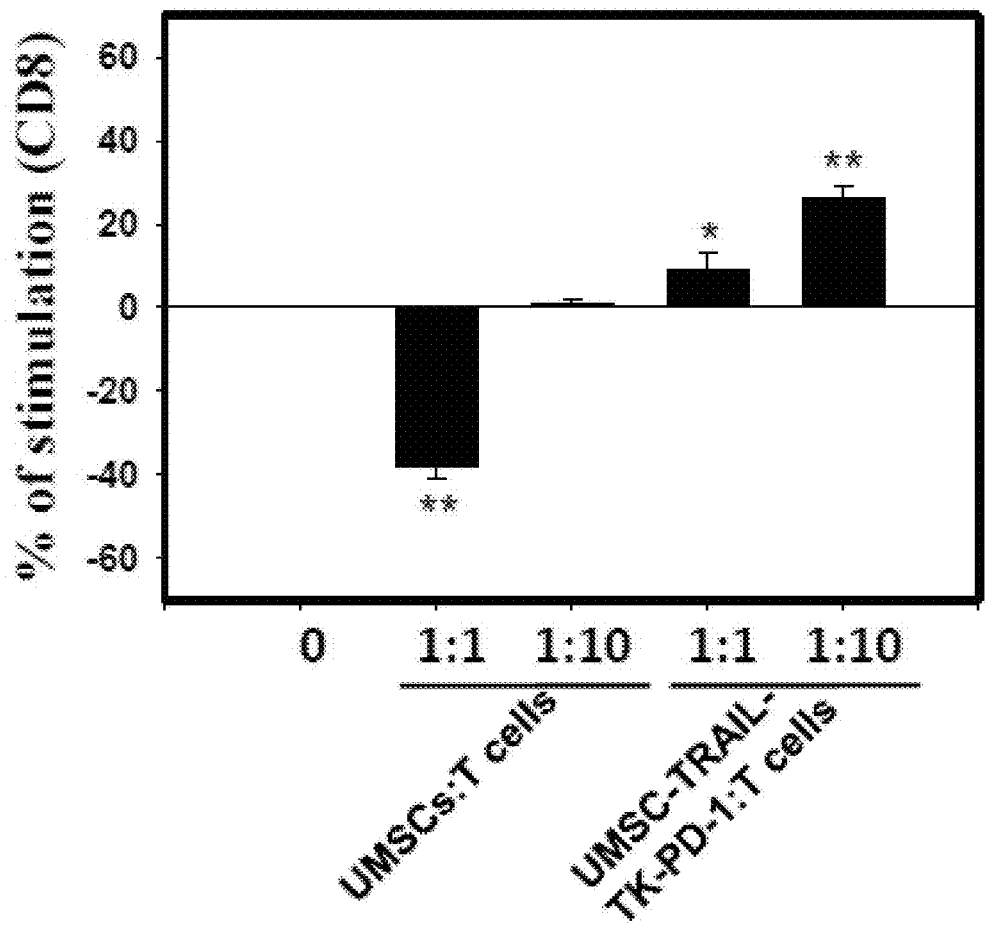
FIG. 2D-(a)
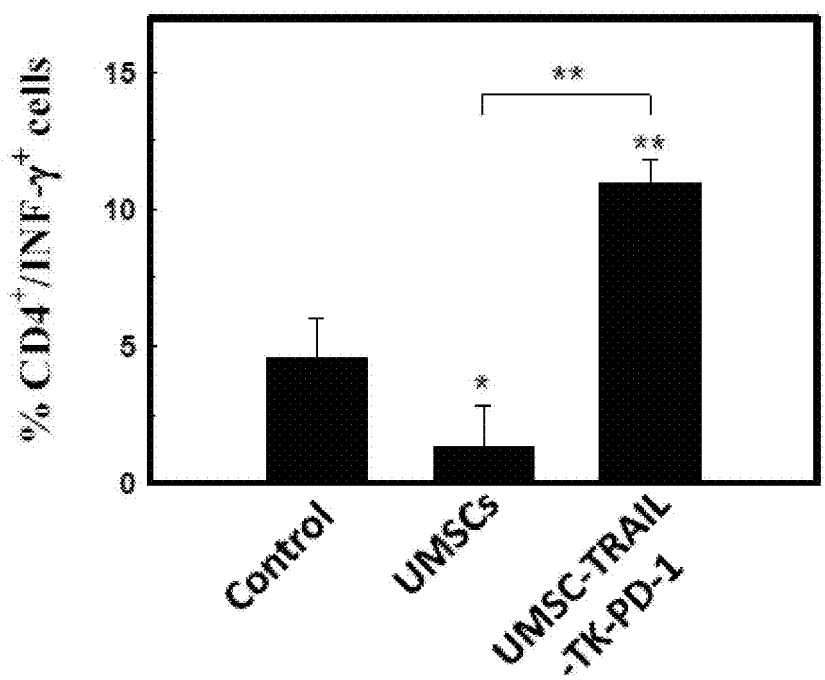

FIG. 2D-(b)
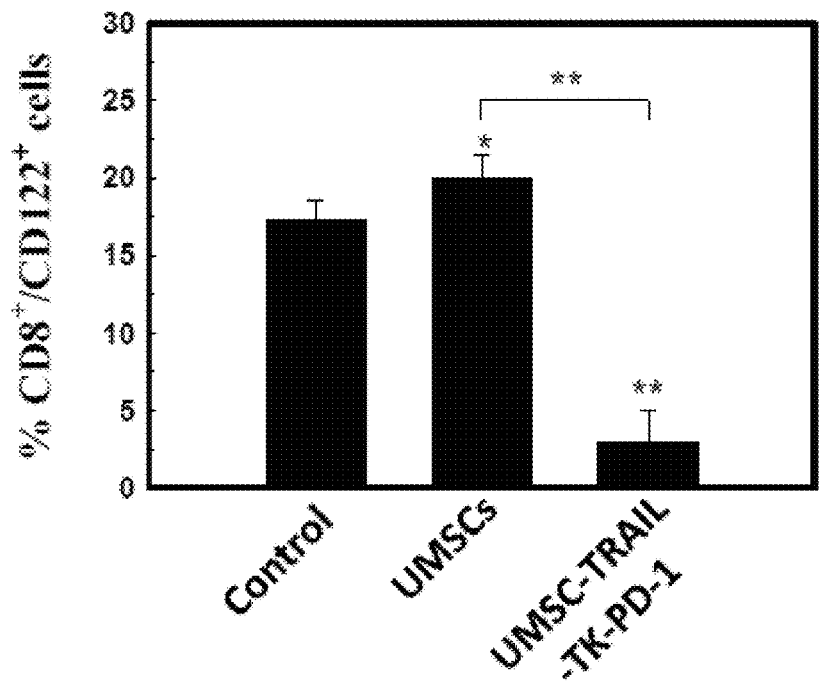
FIG. 3A
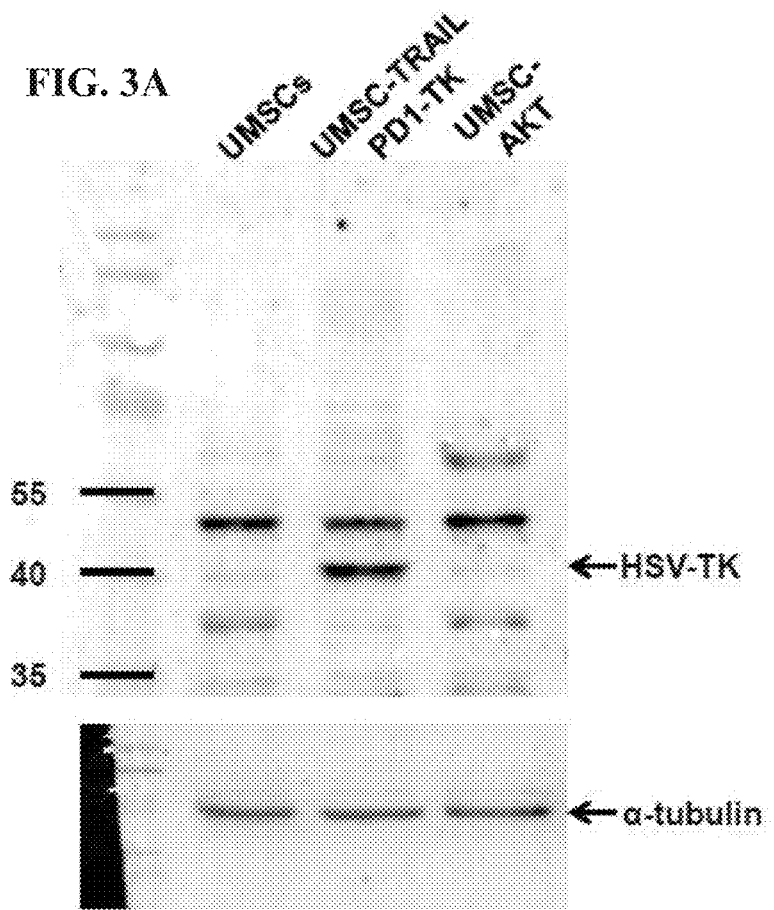

FIG. 3B-(a)
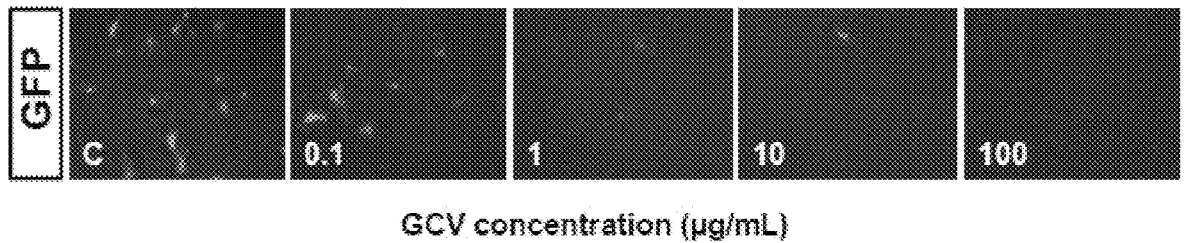
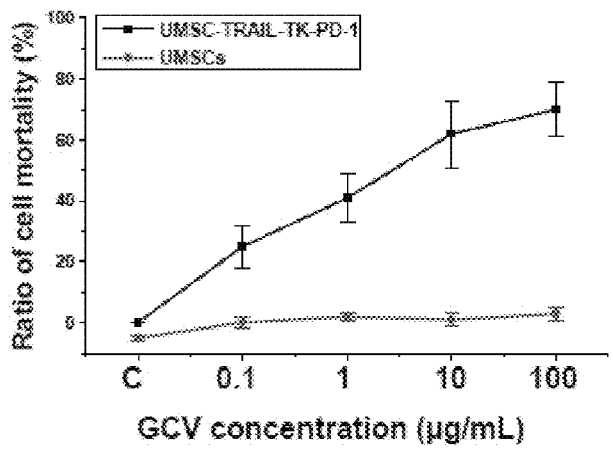
FIG. 3B-(b)
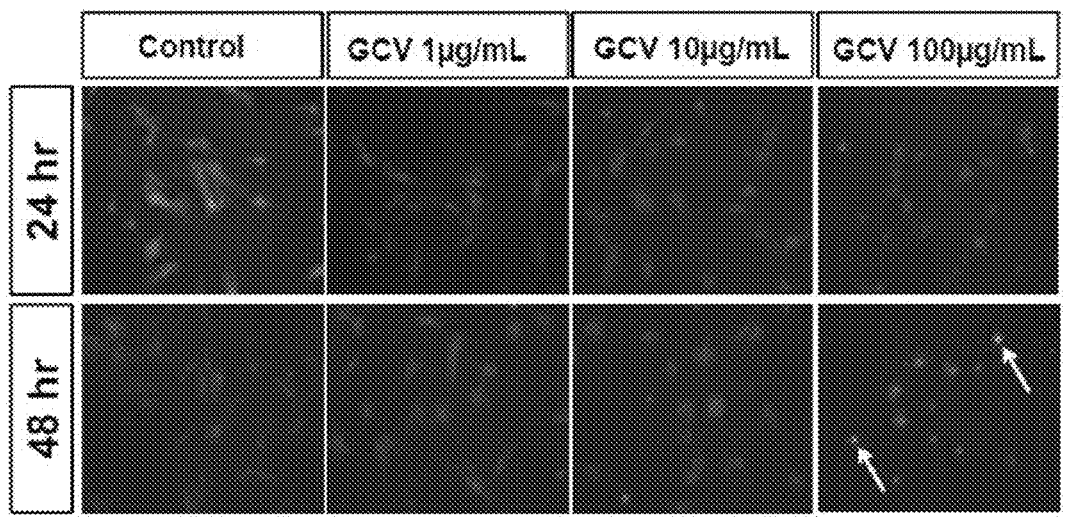

FIG. 3C-(a)
Bystander effect
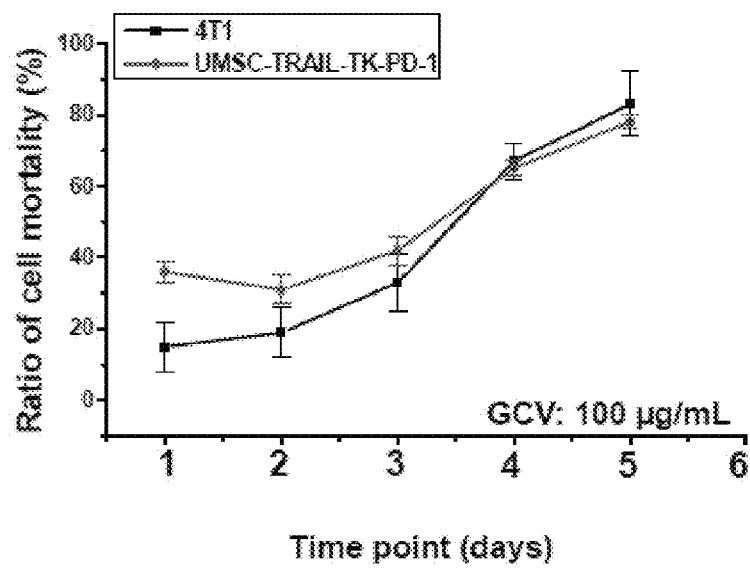
FIG. 3C-(b)
4T1/UMSC-TRAIL-TK-PD-1-GFP co-culture
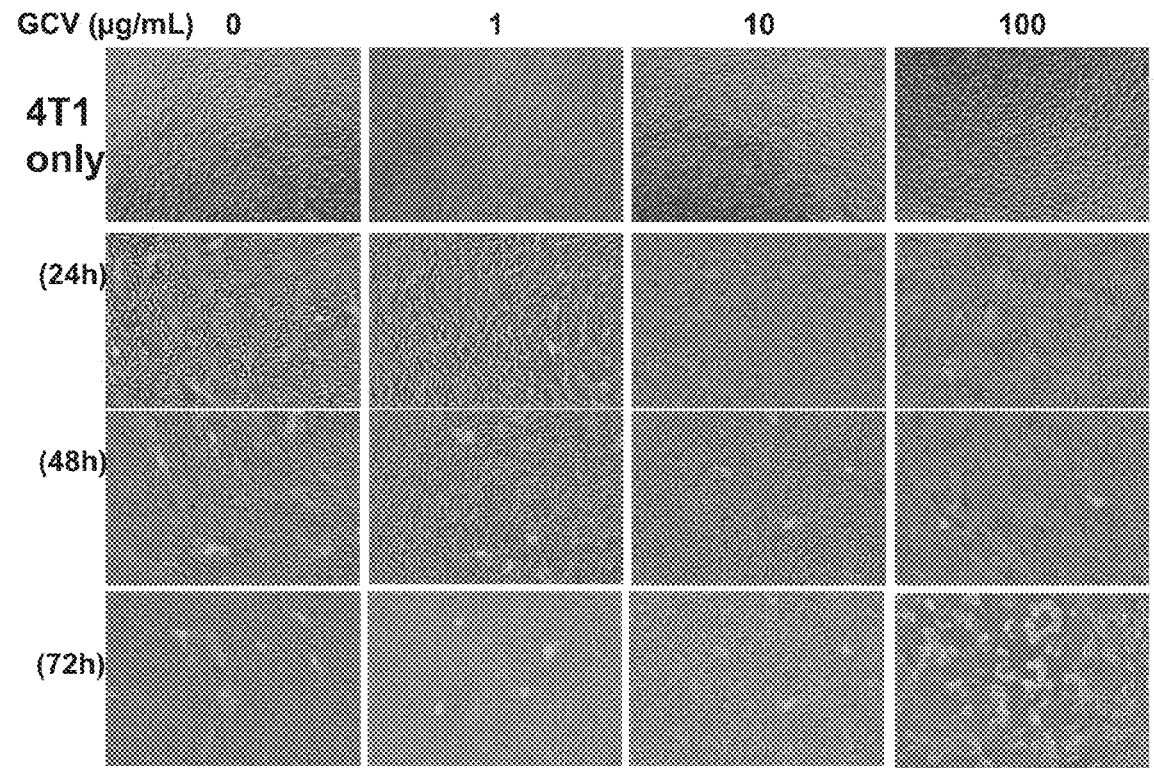

FIG. 3C-(c)
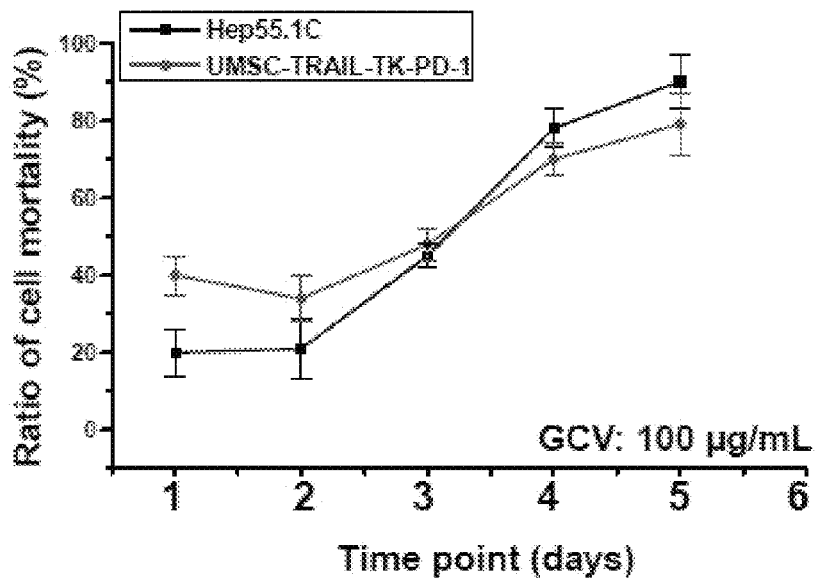
FIG. 3C-(d)
Hep55.1C/UMSC-TRAIL-TK-PD-1-GFP co-culture
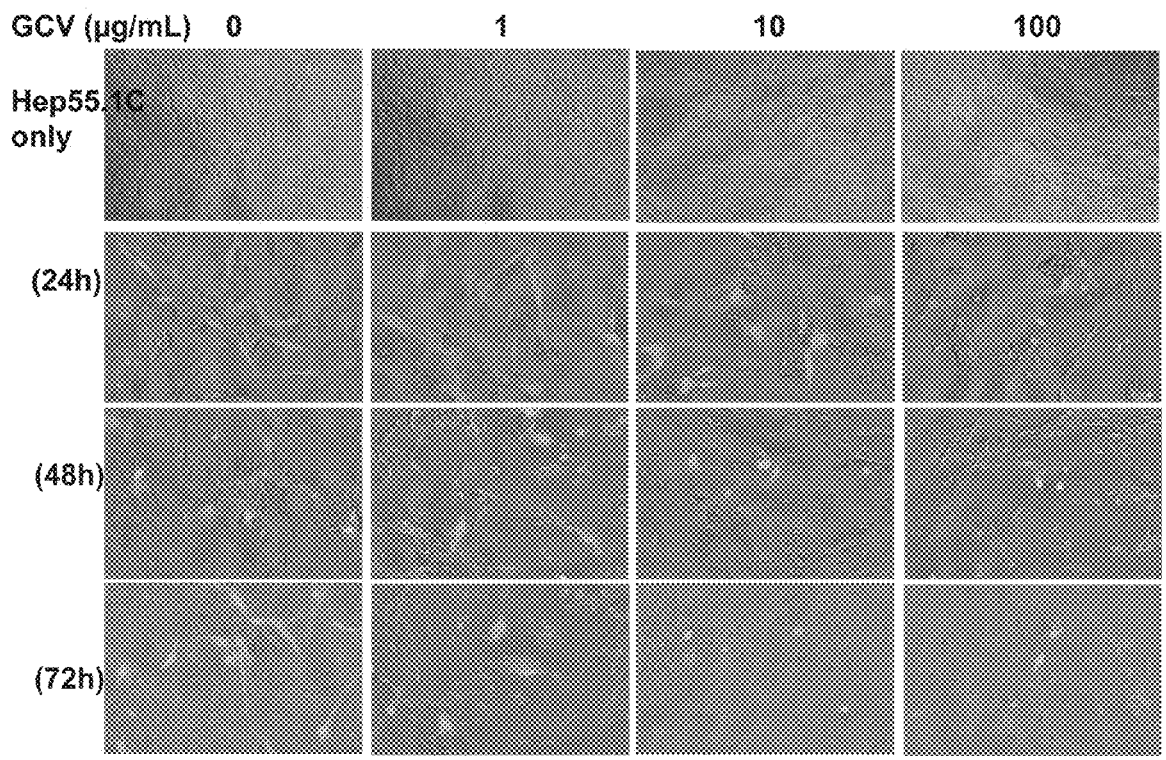

FIG. 3C-(e)
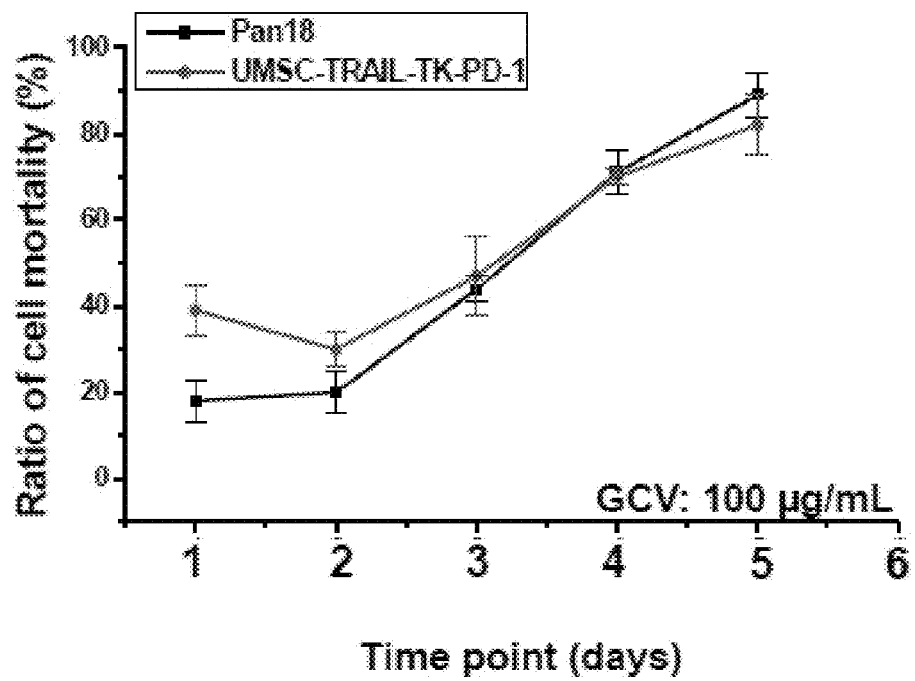
FIG. 3C-(f)
Pan18/UMSC-TRAIL-TK-PD-1-GFP co-culture
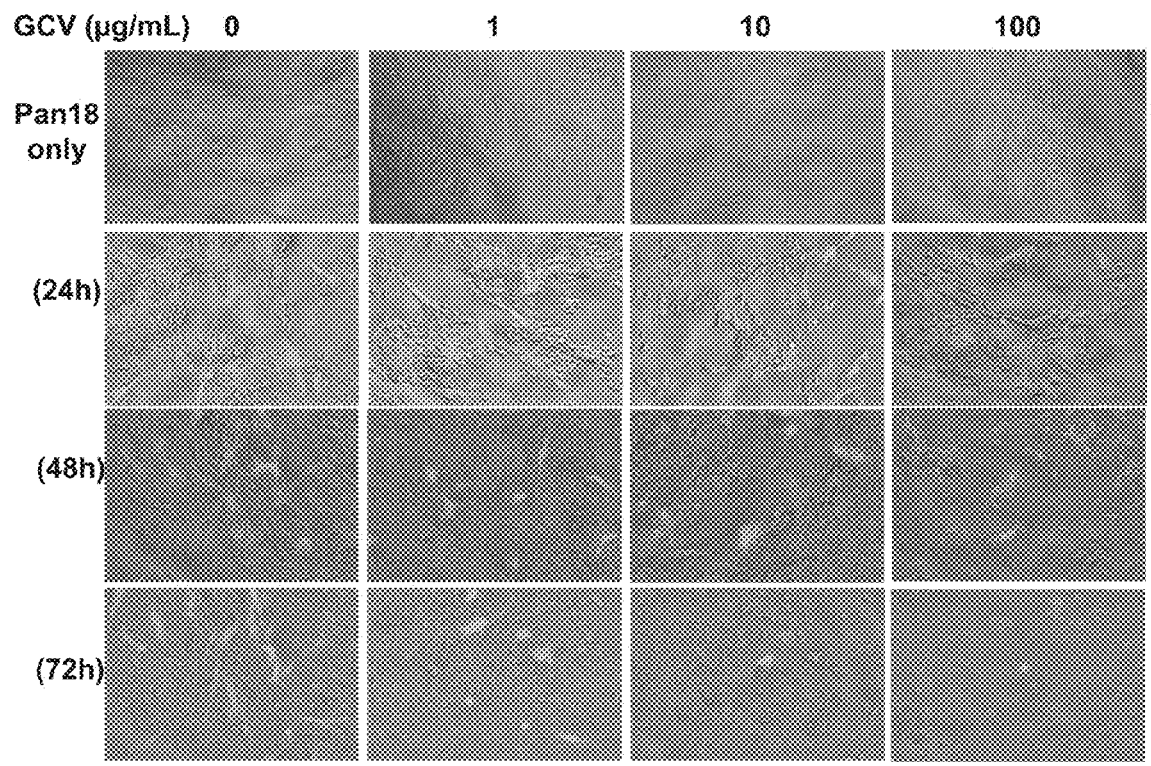

FIG. 3C-(g)
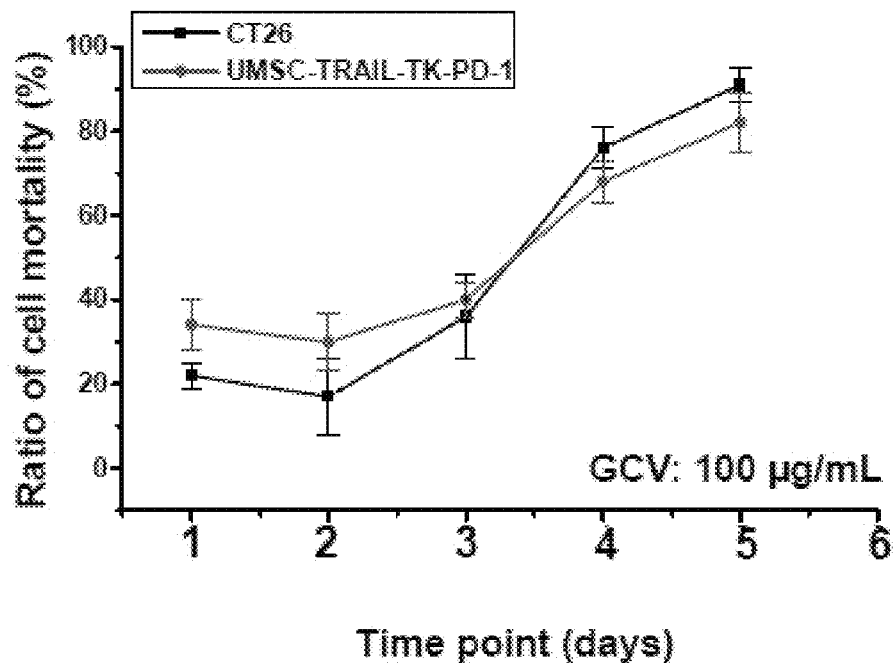
FIG. 3C-(h)
CT26/UMSC-TRAIL-TK-PD-1-GFP co-culture
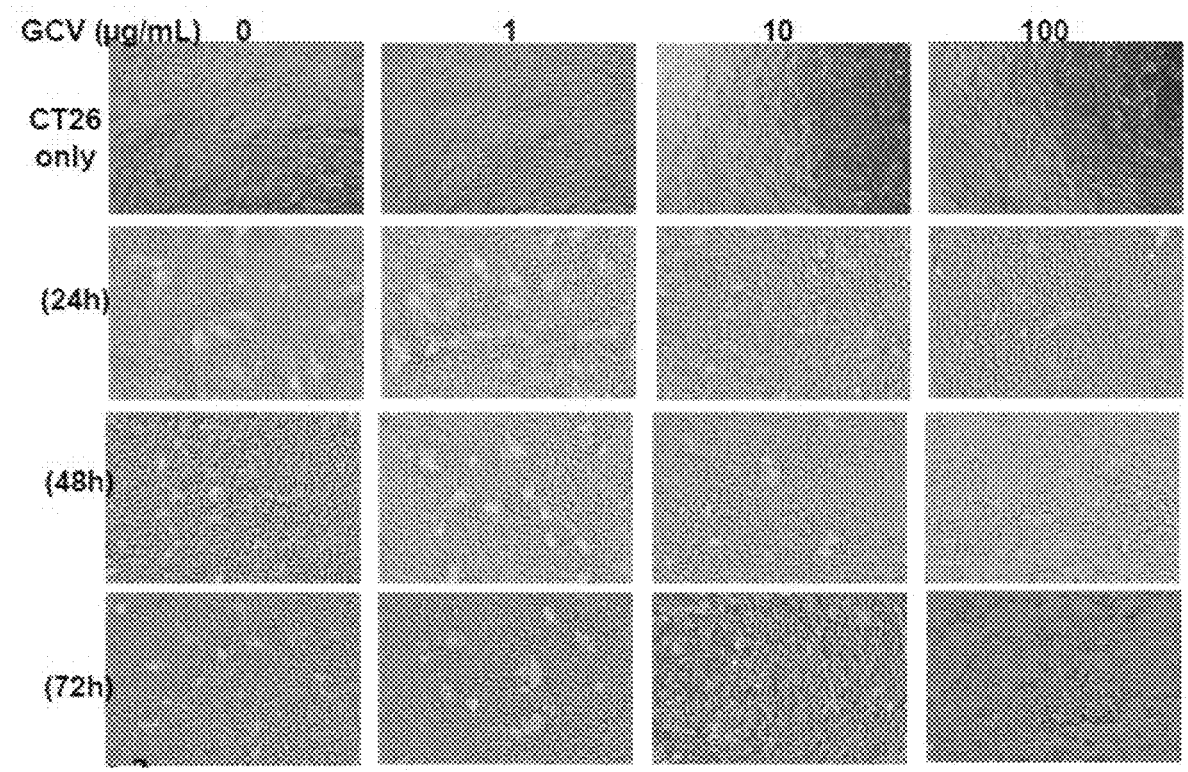

FIG. 3C-(i)
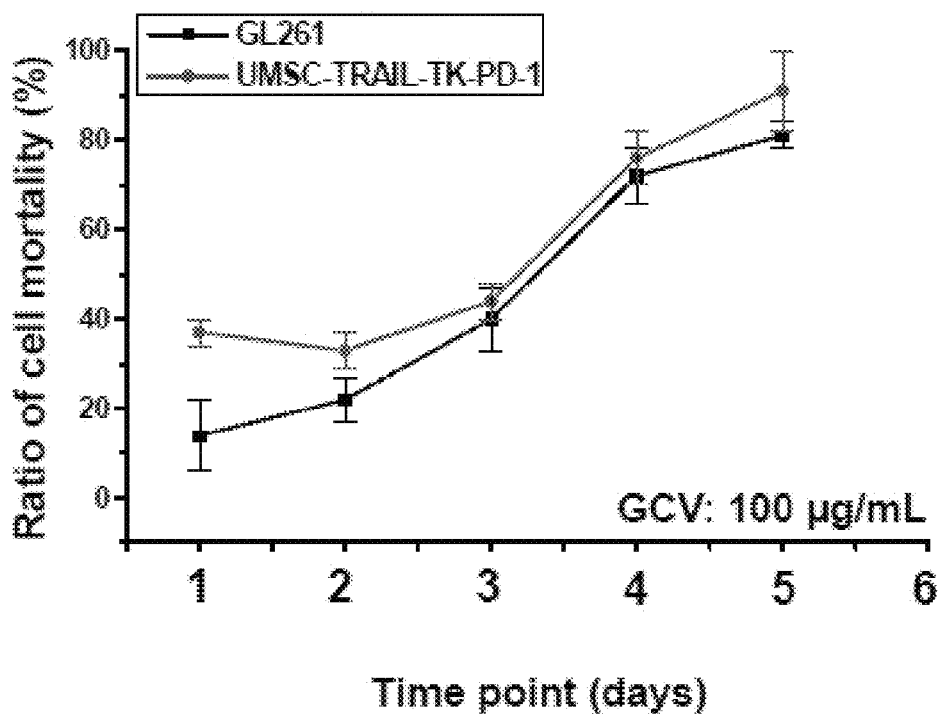
FIG. 3C-(j)
GL261/UMSC-TRAIL-TK-PD-1-GFP co-culture
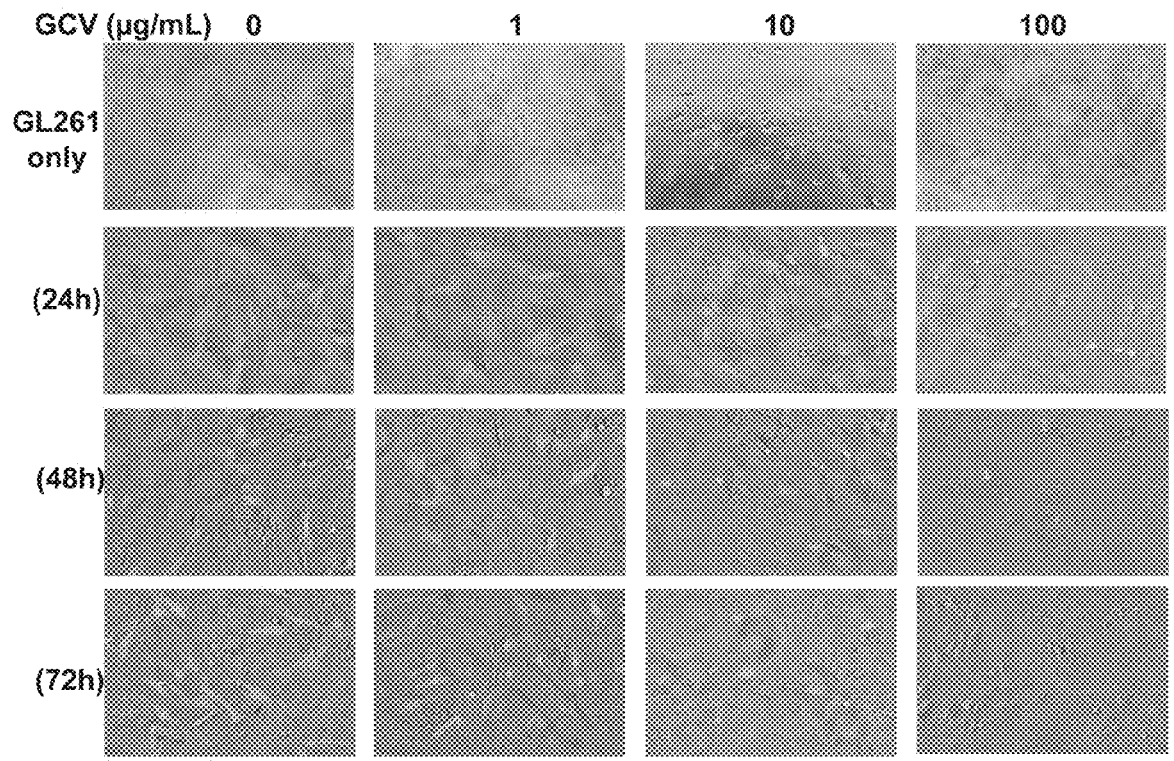

FIG. 3E-(a)

Bystander effect

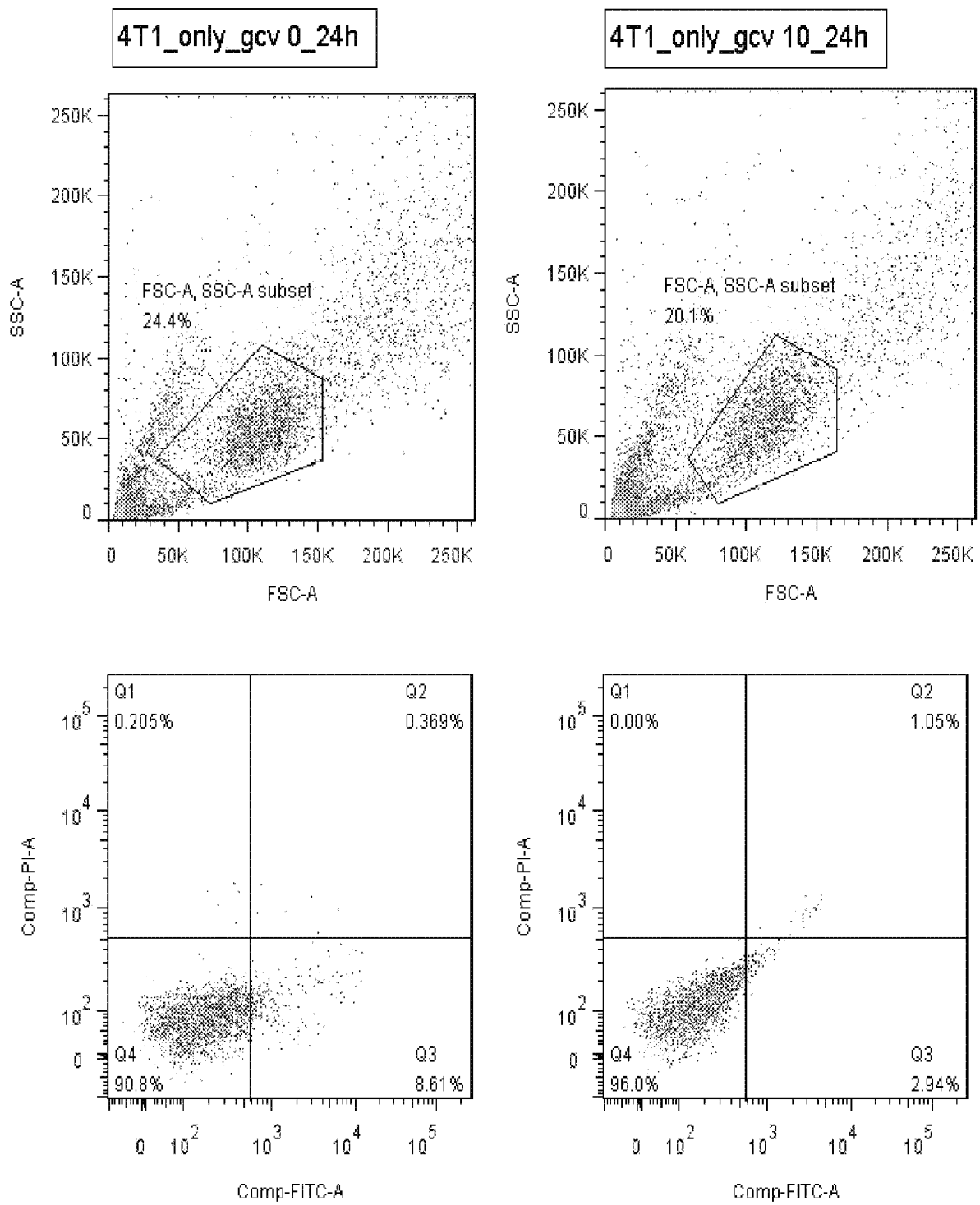
FIG. 3E-(b)
4T1/UMSC-TRAIL-TK-PD-1, co-culture 24h (PI/Annexin-V)

FIG. 3E-(b) (Continued-1)
4T1/UMSC-TRAIL-TK-PD-1, co-culture 24h (PI/Annexin-V)
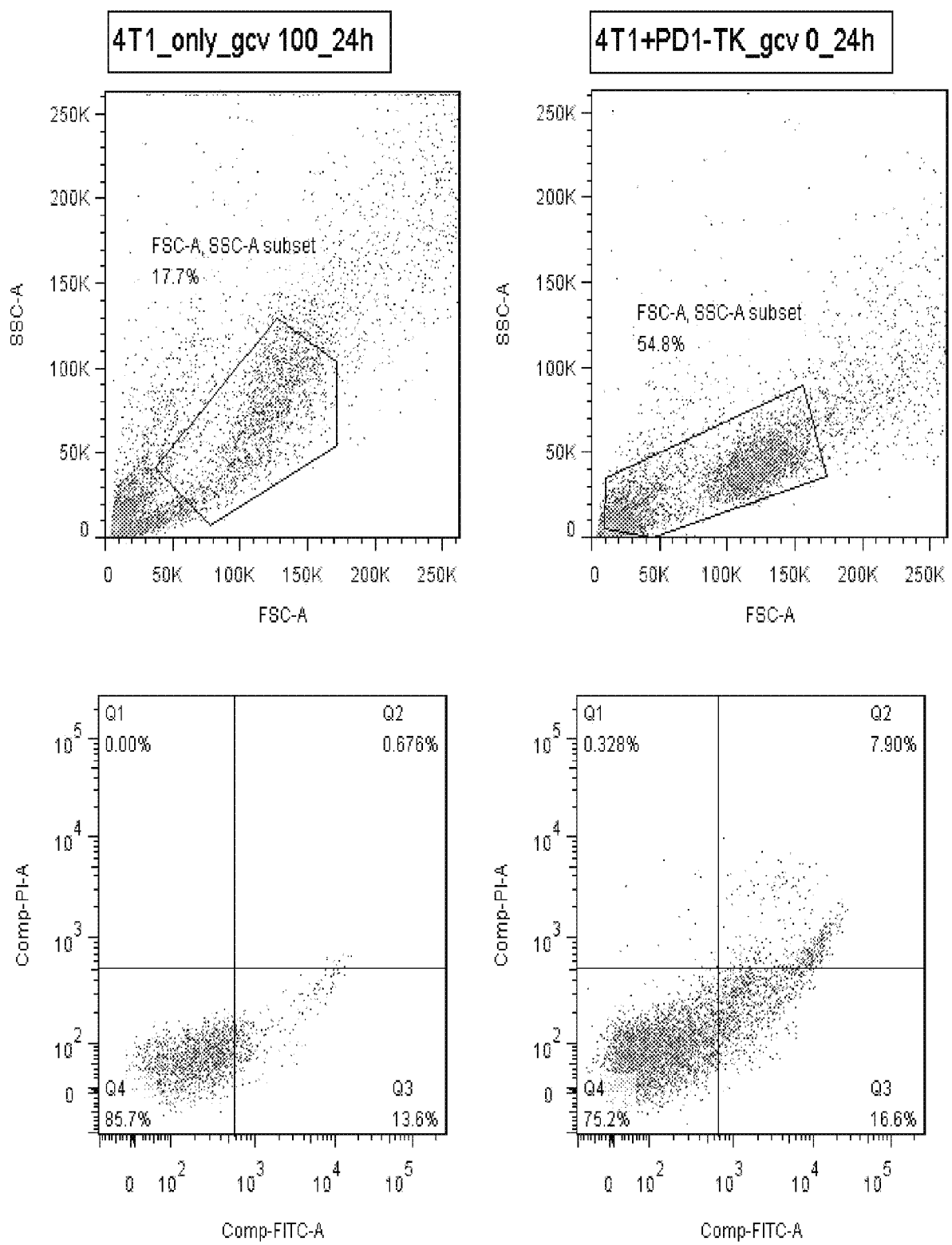

FIG. 3E-(b) (Continued-2)
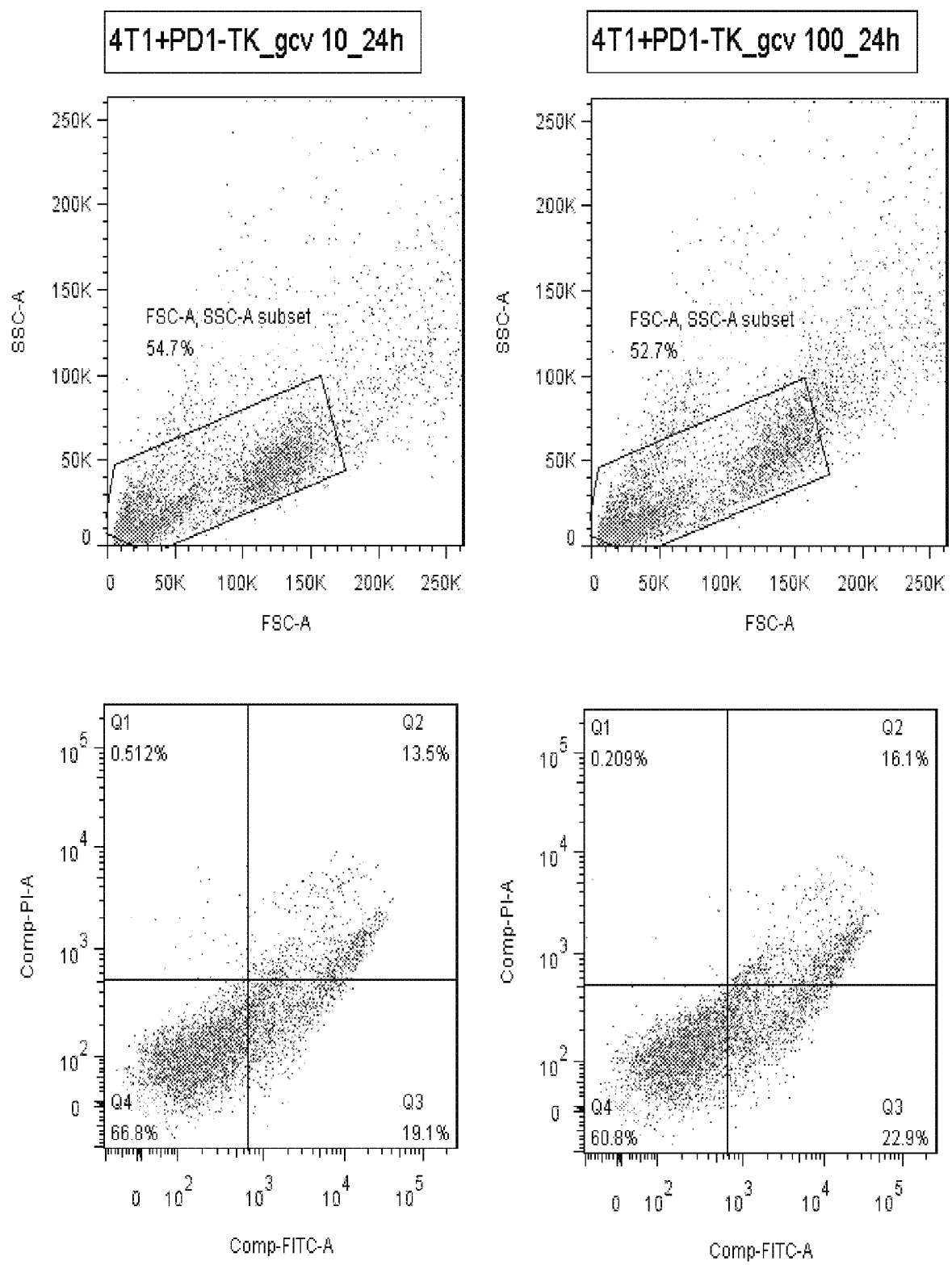

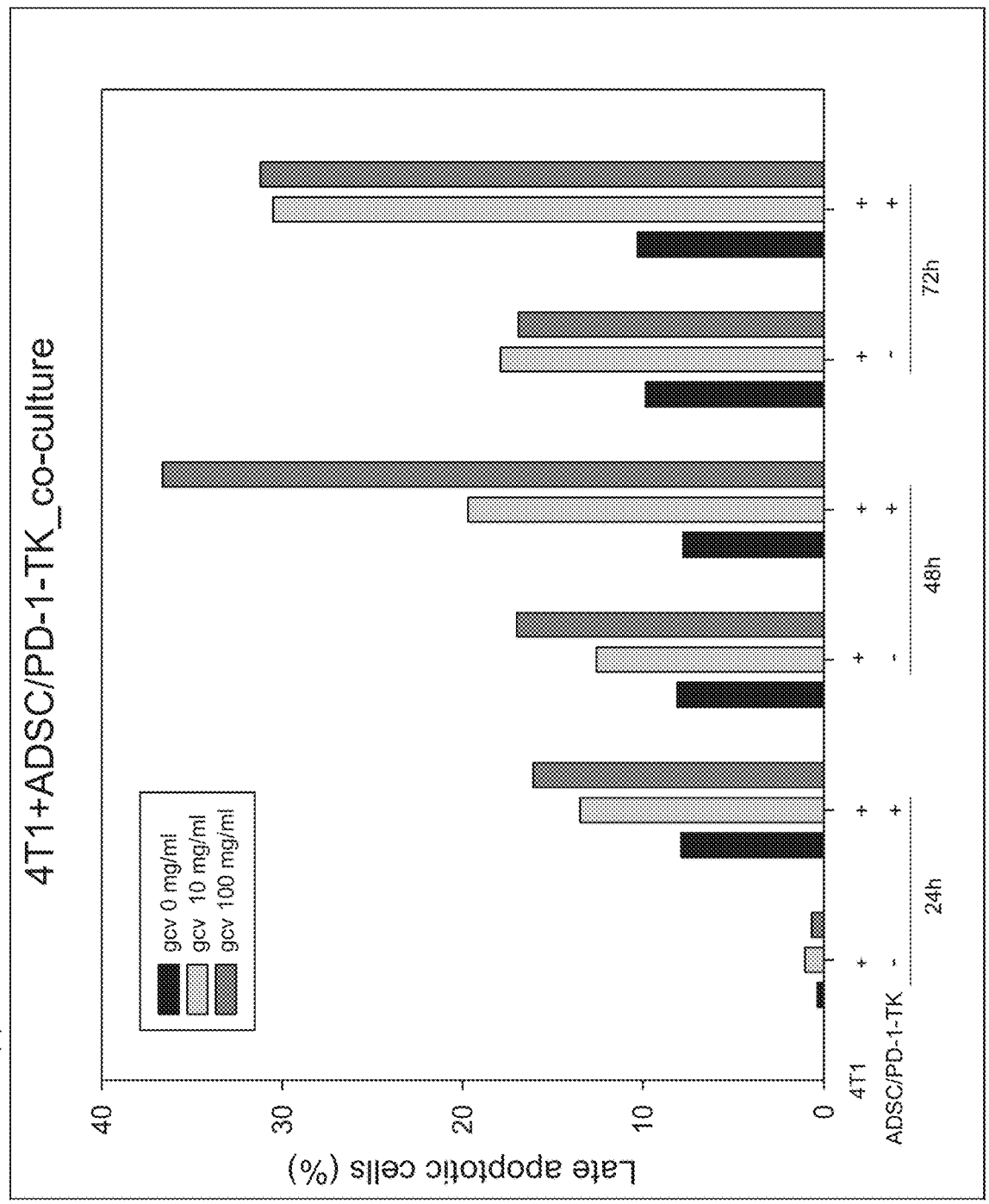
FIG. 3E-(c)

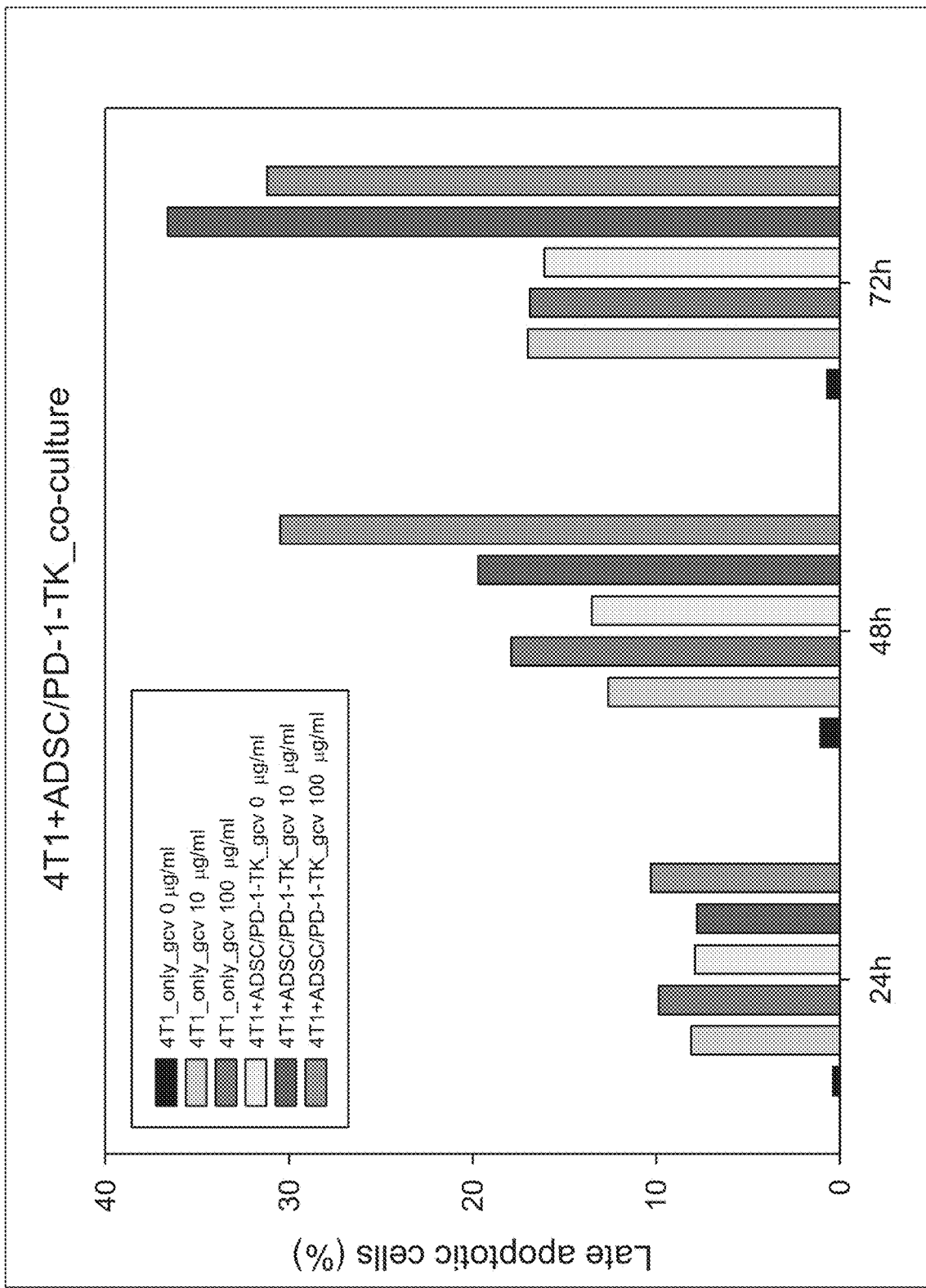
FIG. 3E-(c) (Continued)

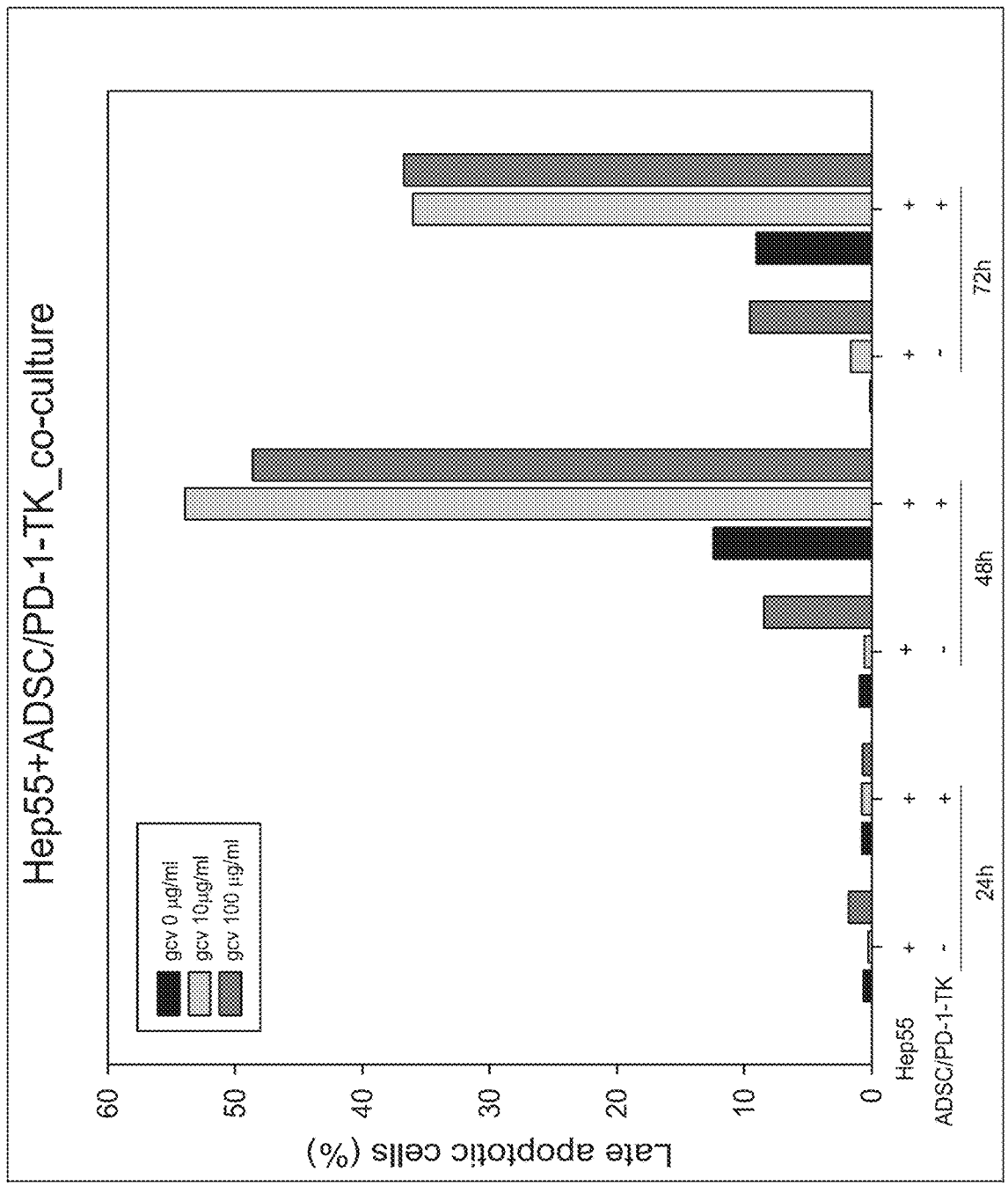
FIG. 3E-(d)

FIG. 3E-(d) (Continued)
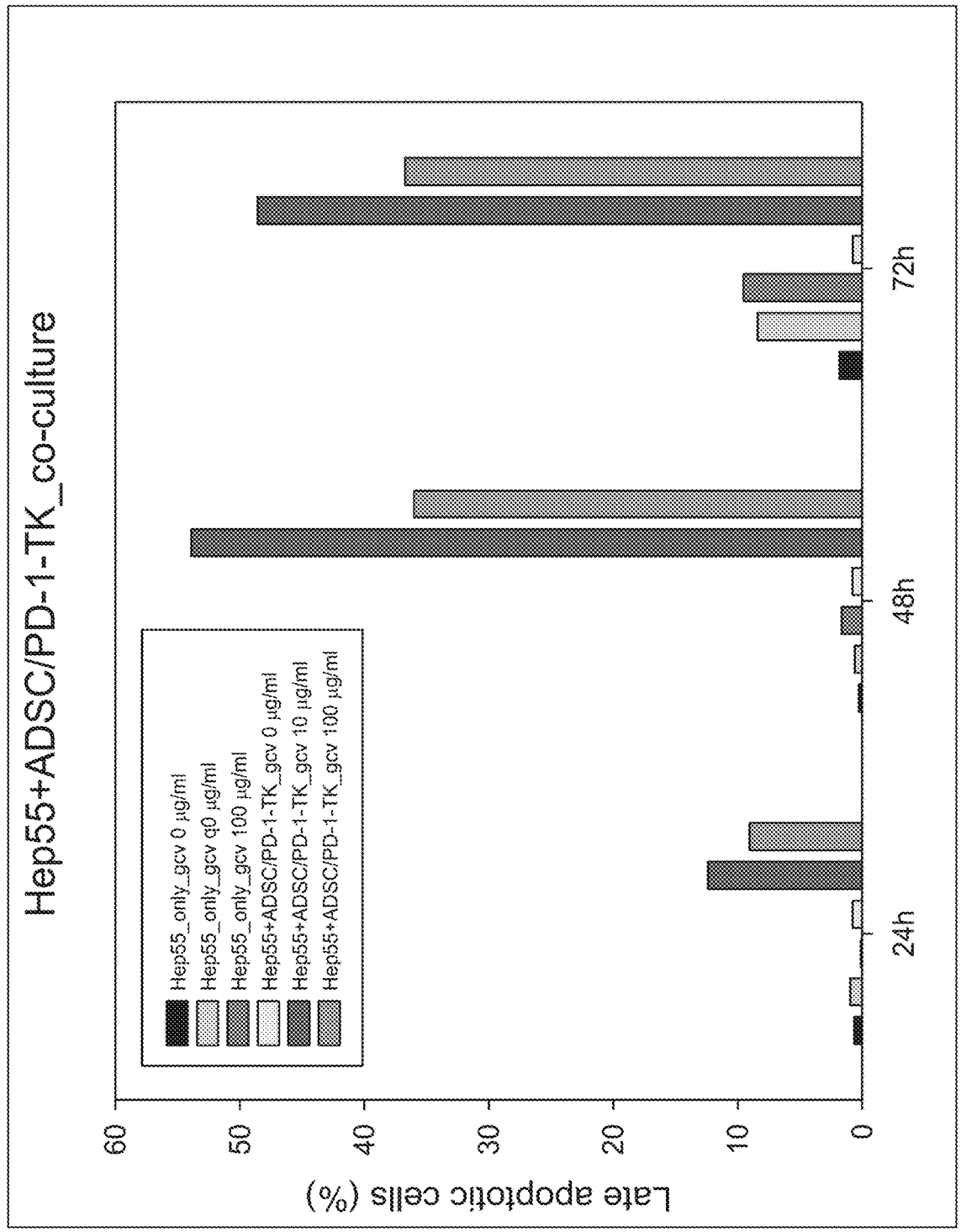

FIG. 4B-(a)

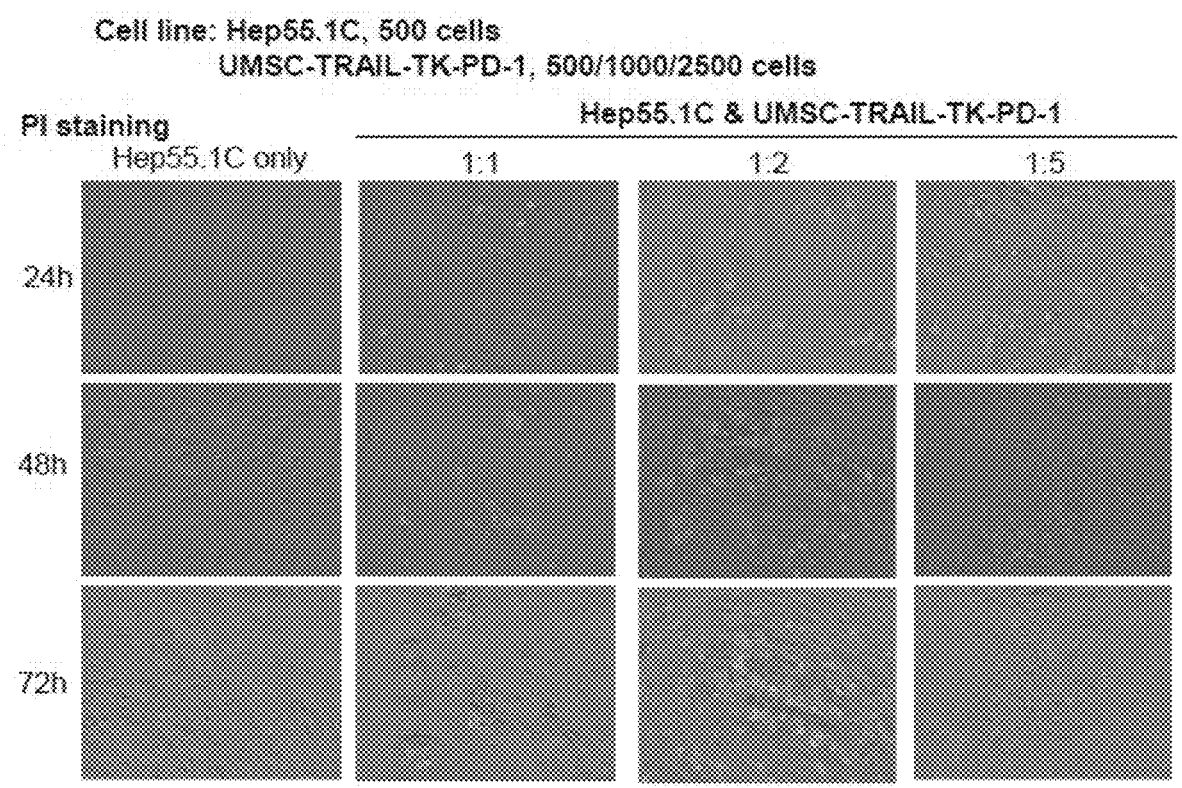
FIG. 4B-(b)

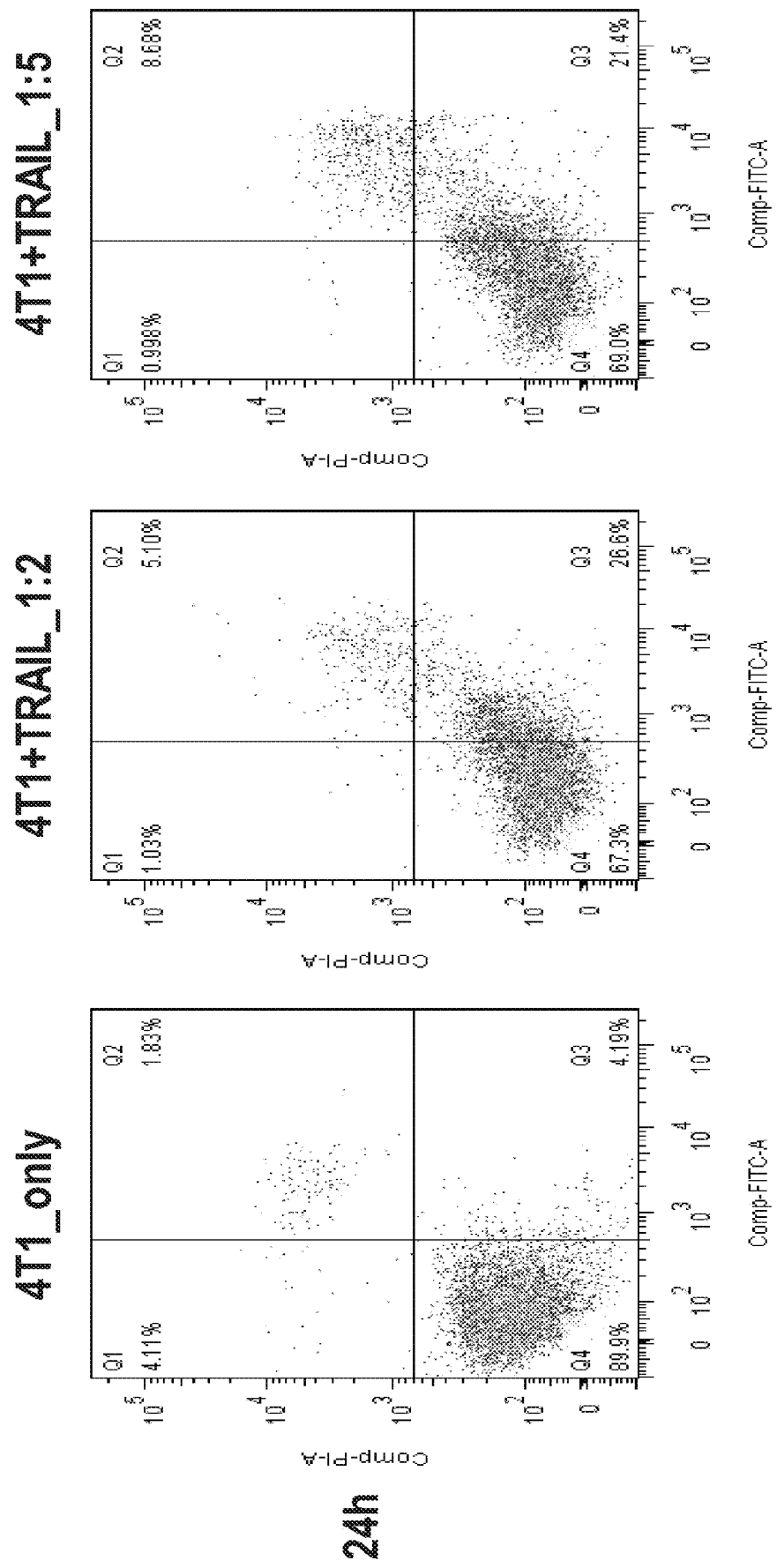
FIG. 4B-(c)

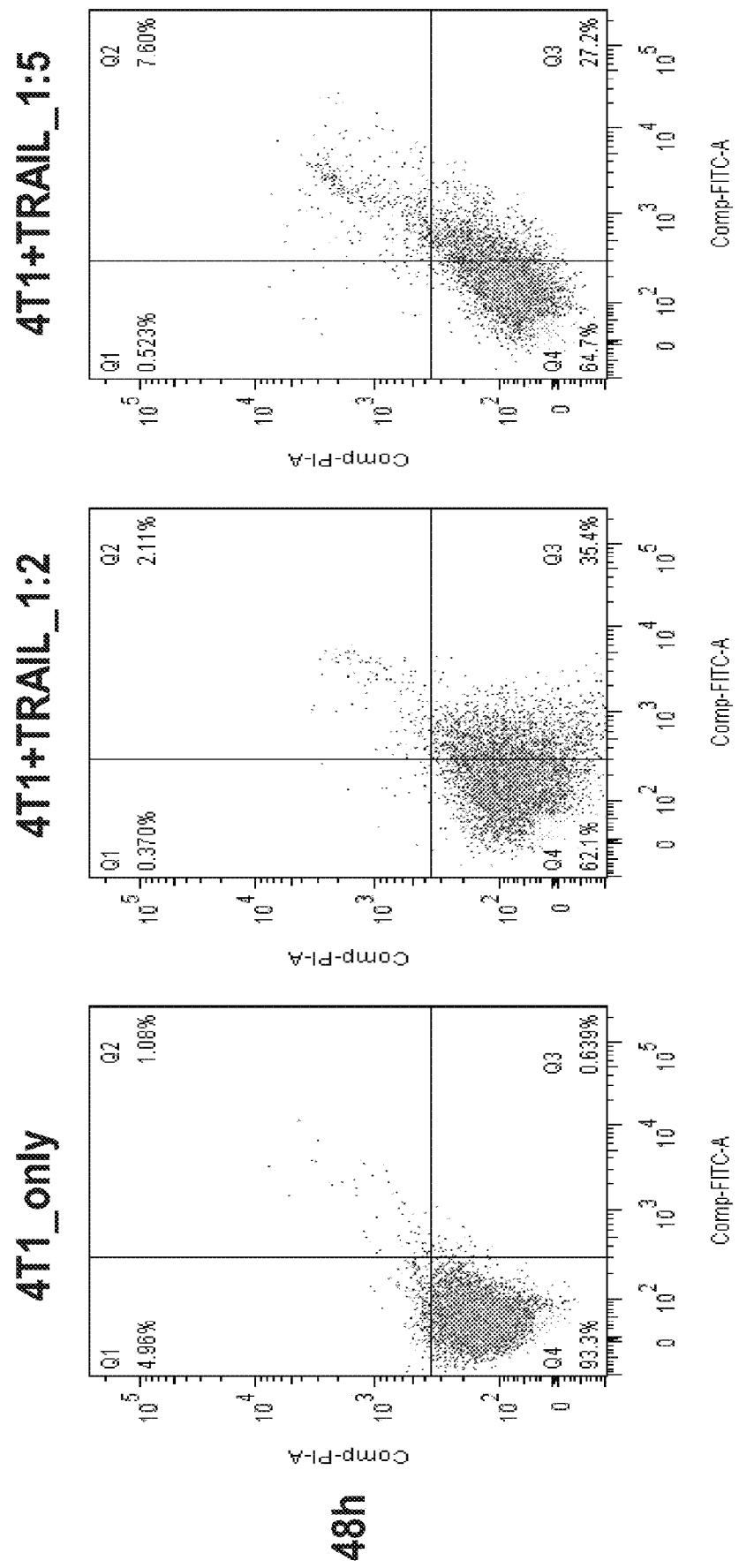
FIG. 4B-(c) (Continued-1)

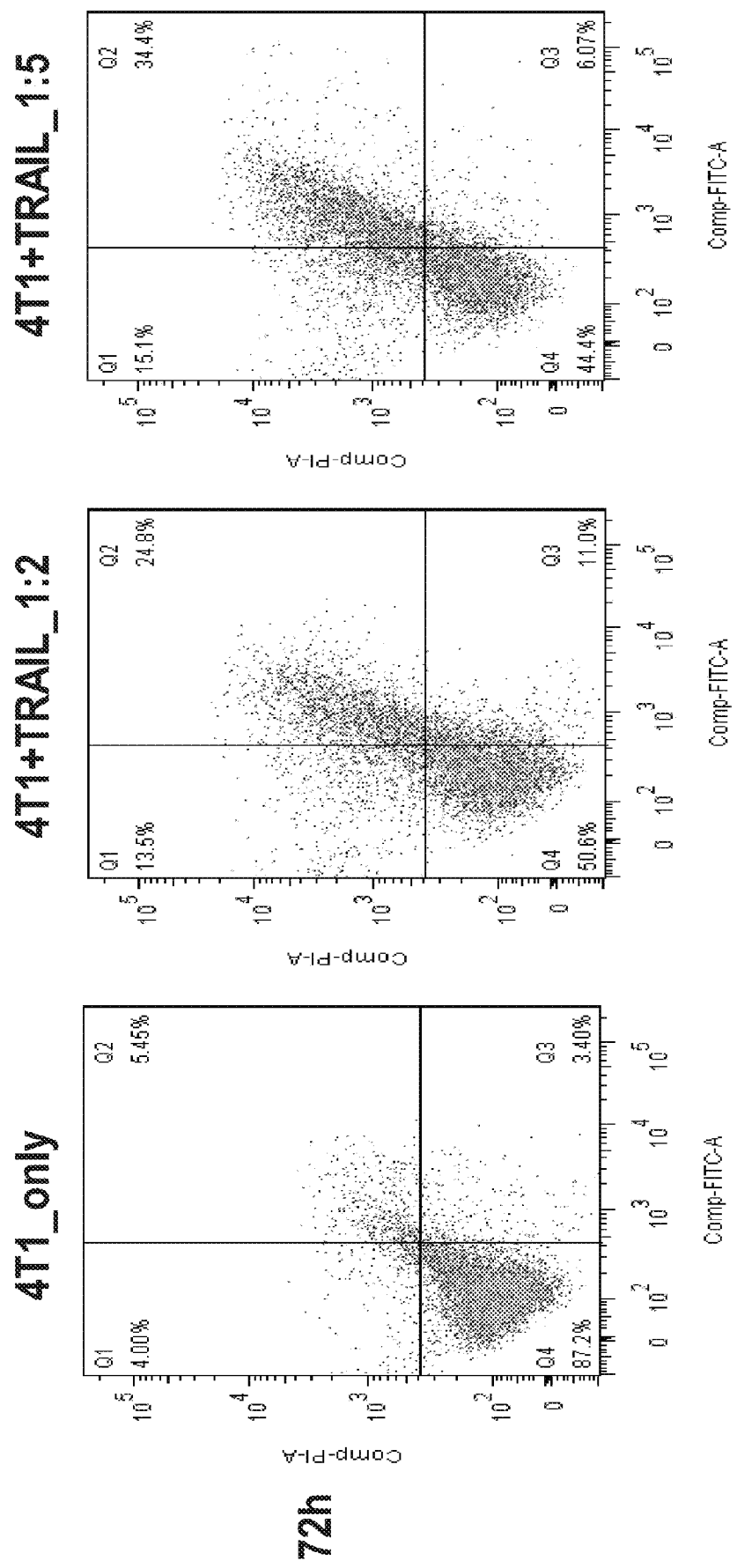
FIG. 4B-(e) (Continued-2)

FIG. 4C-(a)
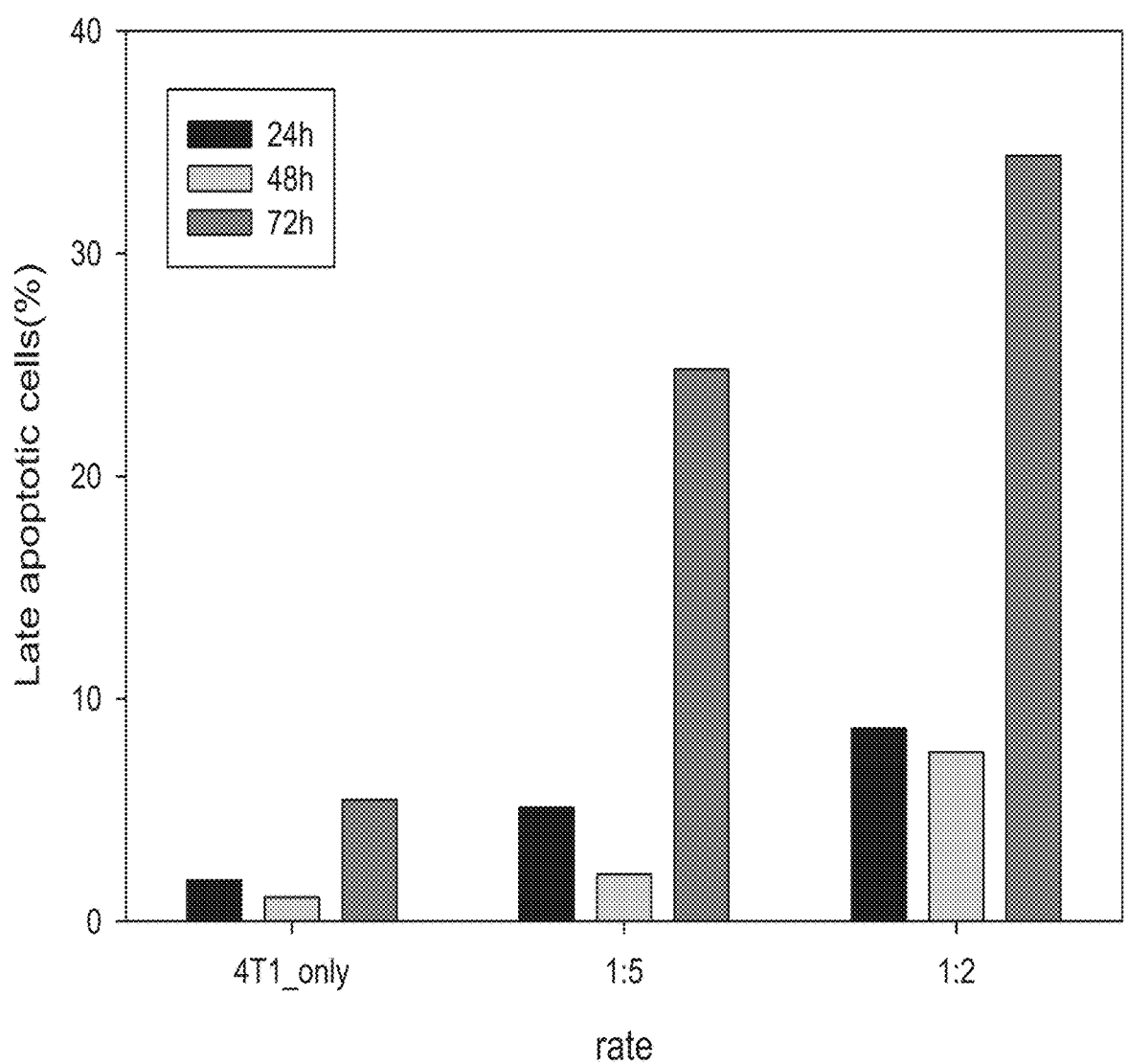

FIG. 4C-(a) (Continued)
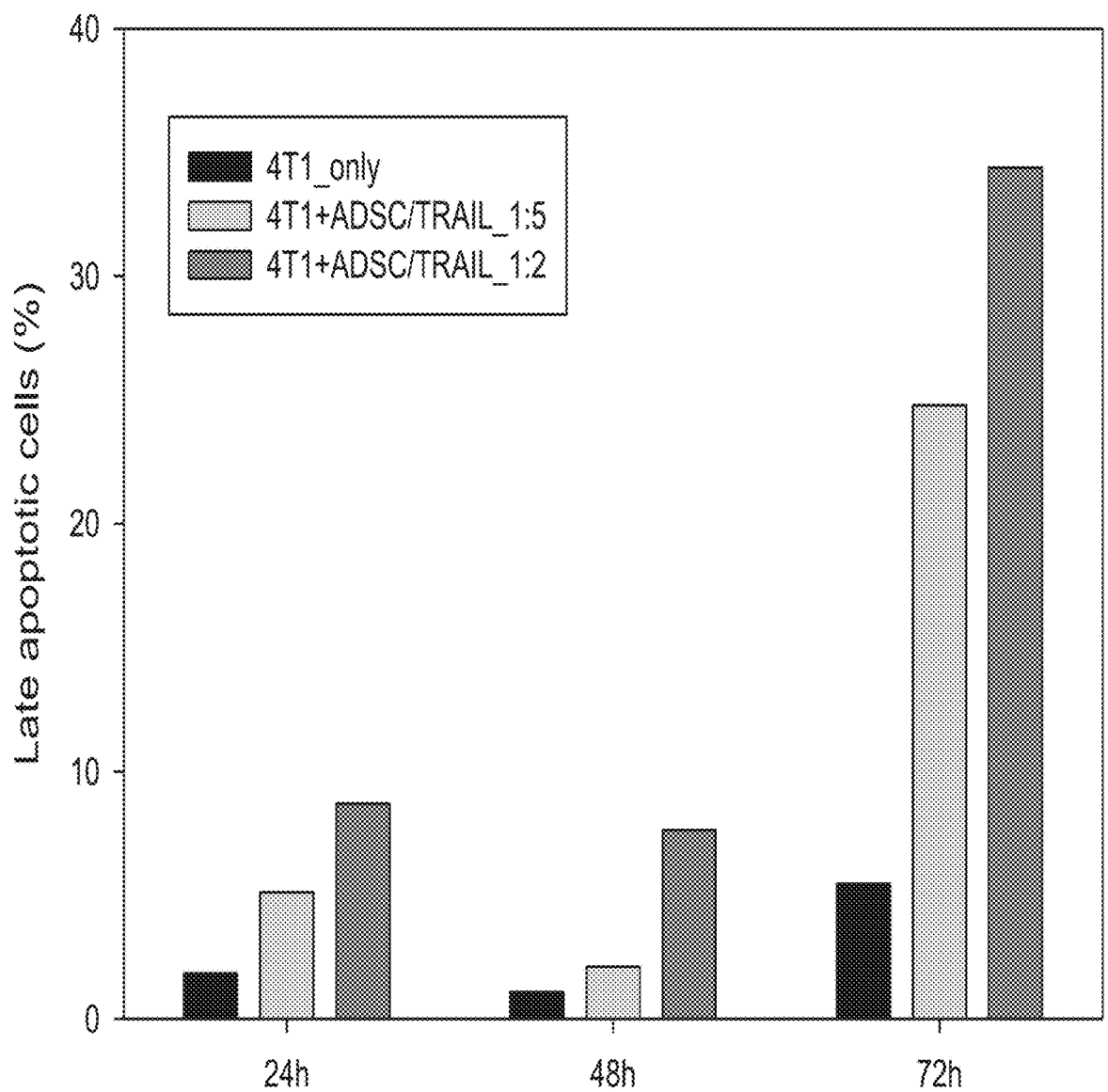

FIG. 4C-(b)
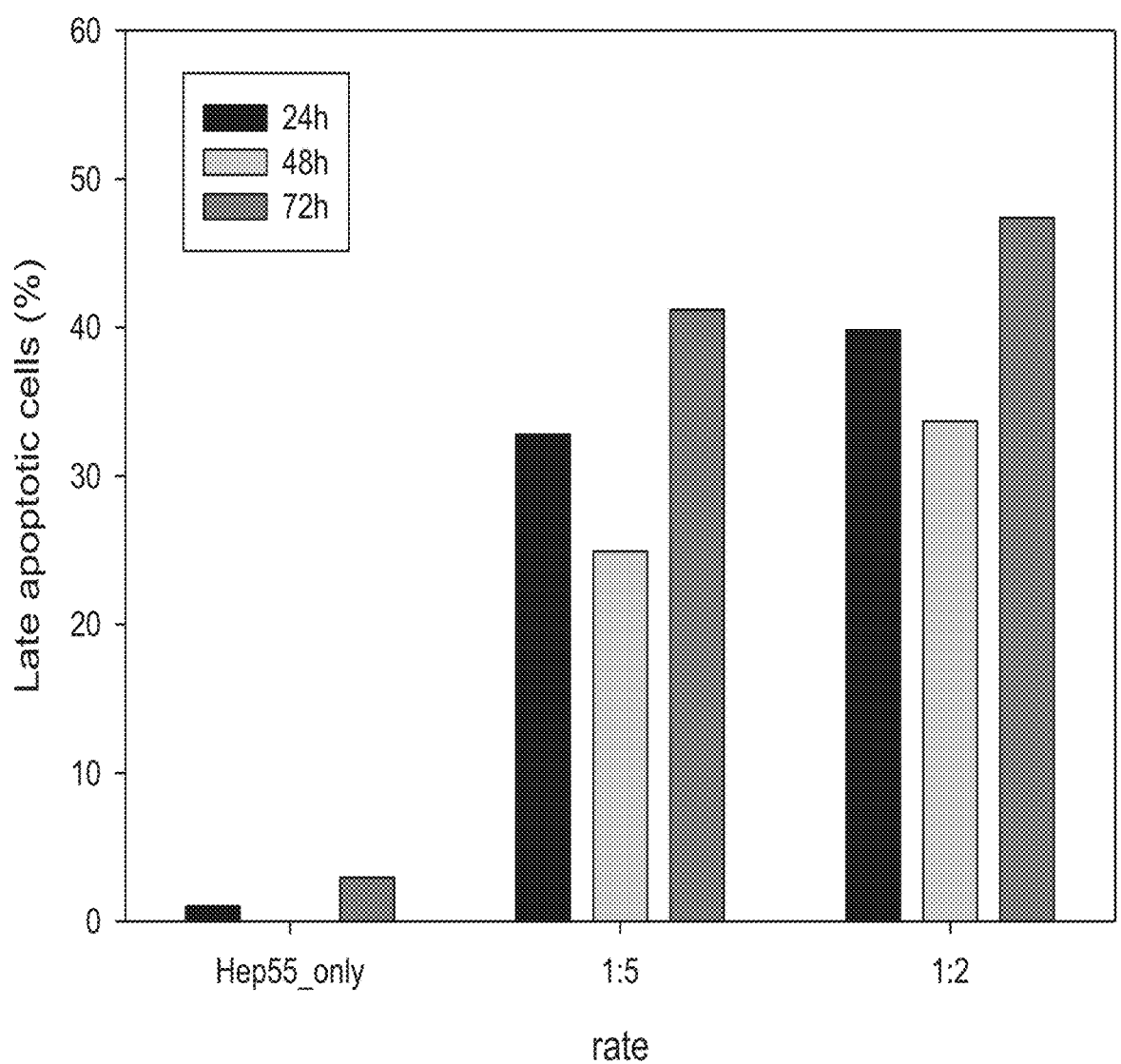

FIG. 4C-(b) (Continued)
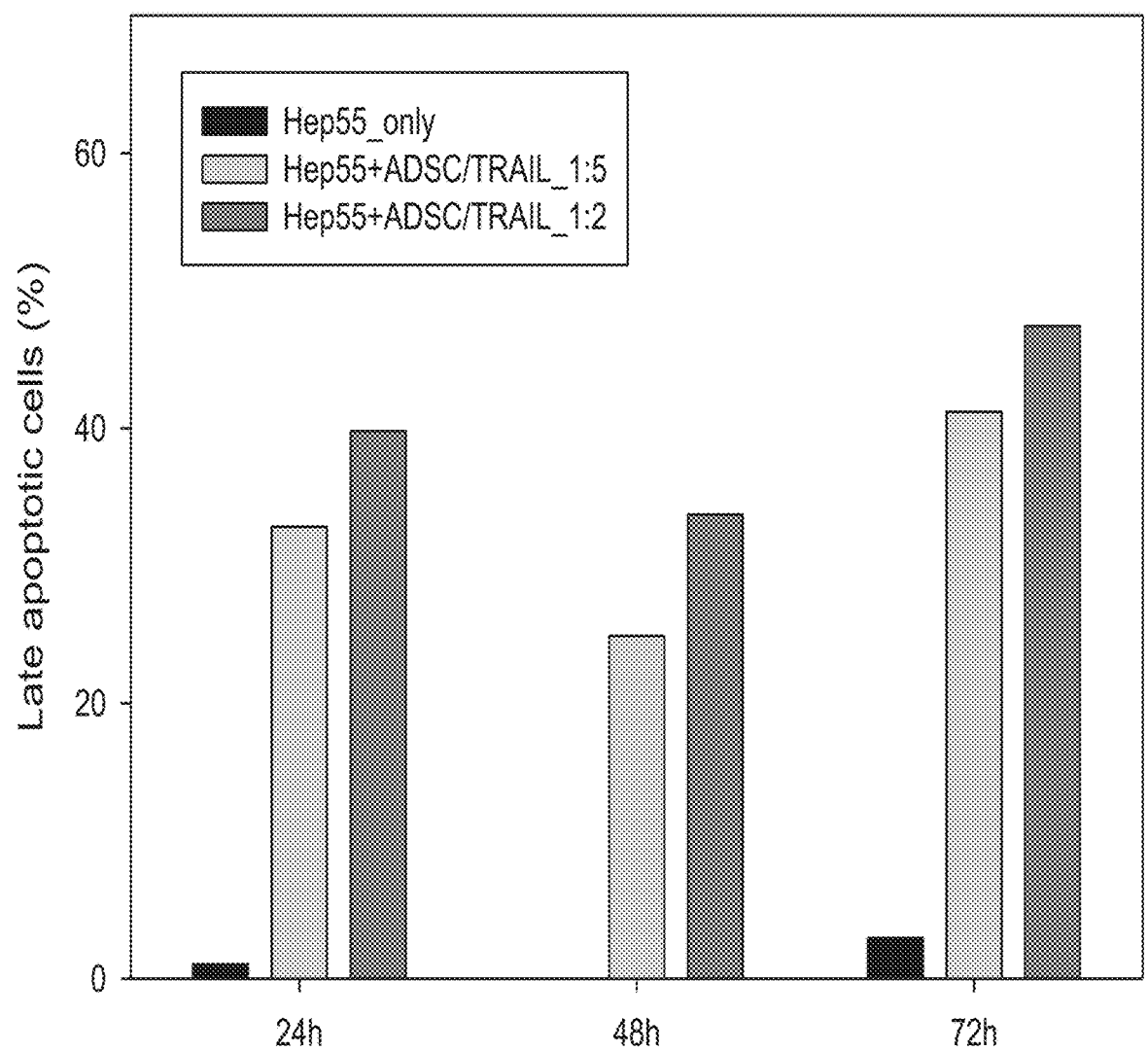

FIG. 6D-(a)

FIG. 6D-(b)
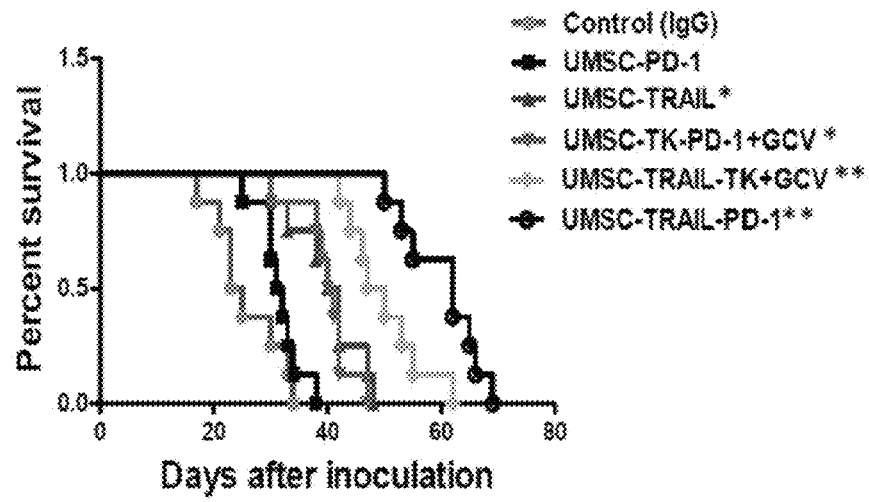
FIG. 6D-(c)
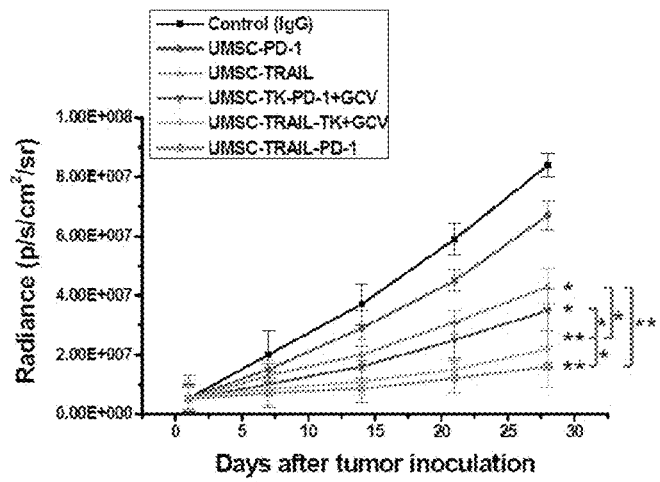
FIG. 6D-(d)
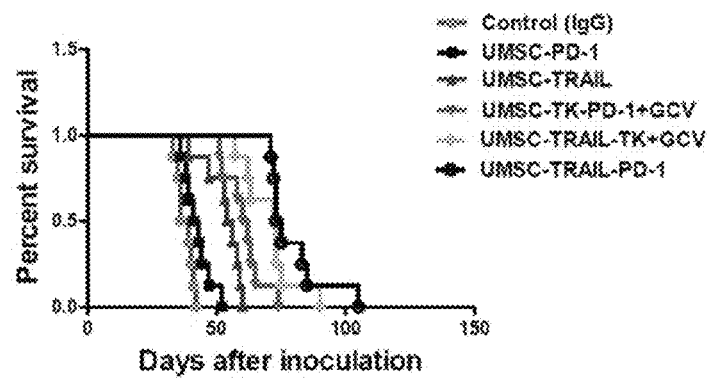

FIG. 6F-(c)
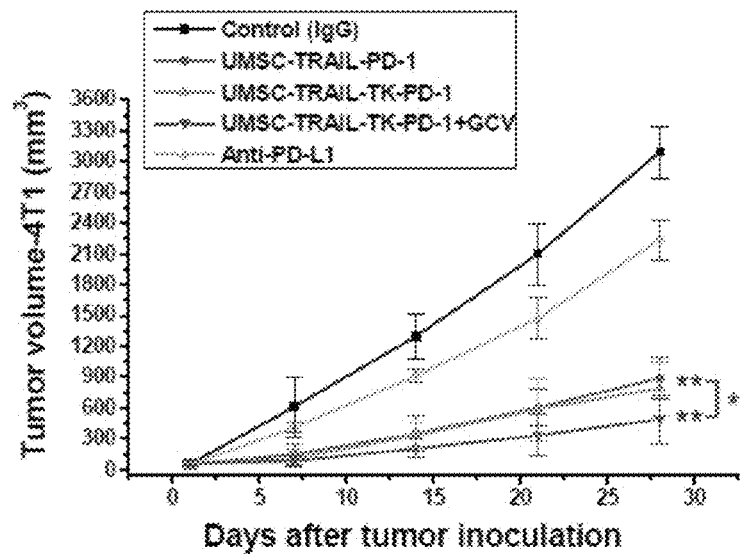
FIG. 6F-(d)
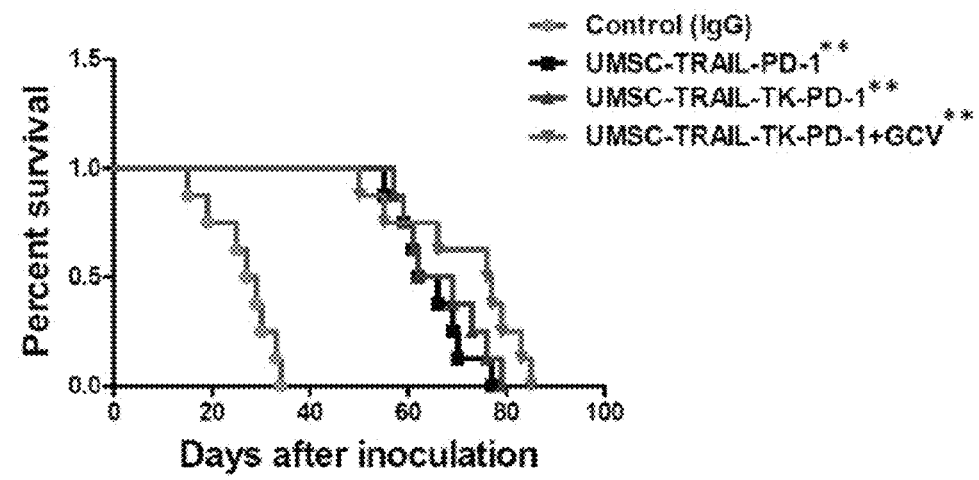
FIG. 6G-(a)
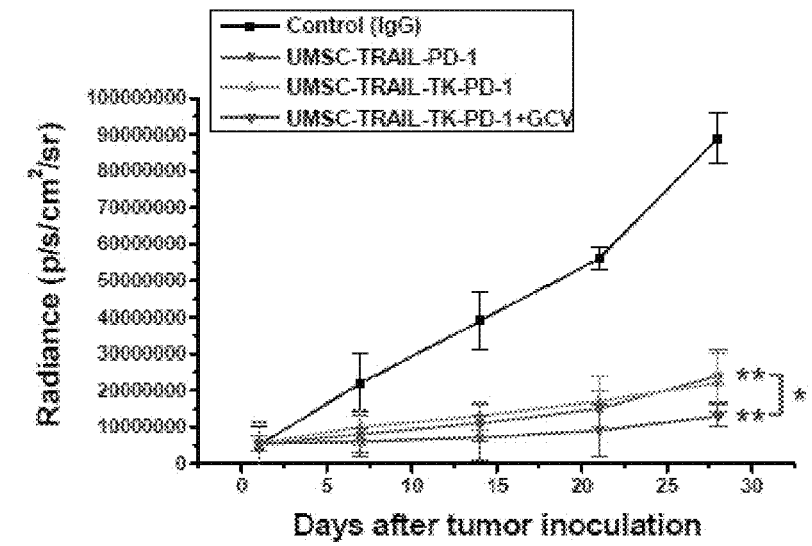

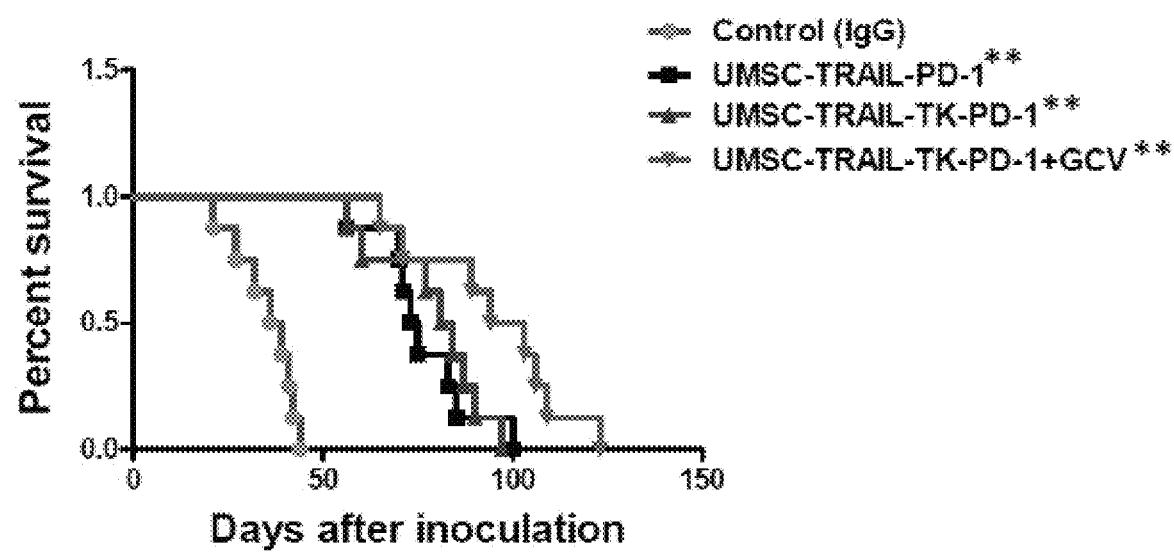
FIG. 6G-(b)

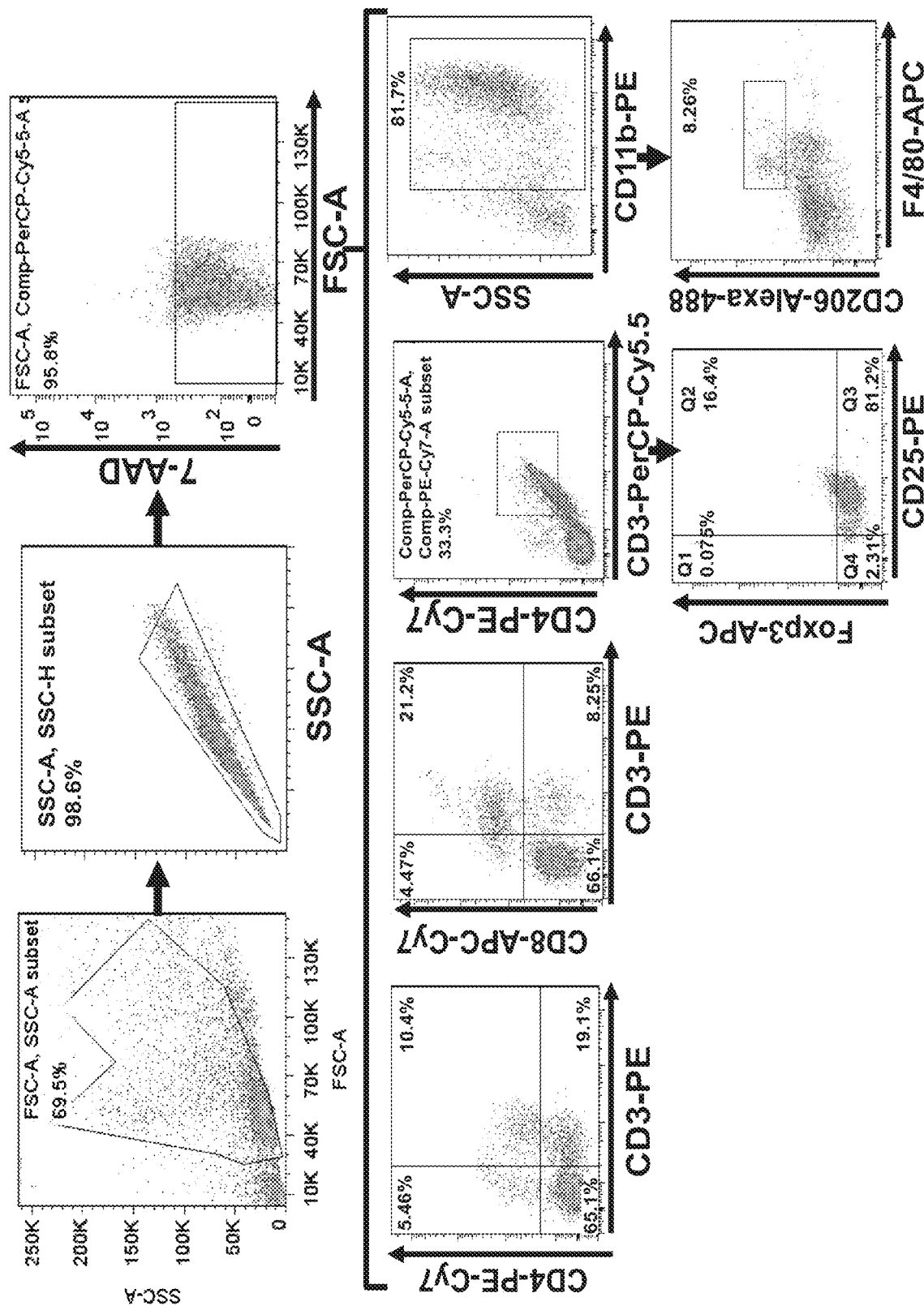
FIG. 7A-(a)

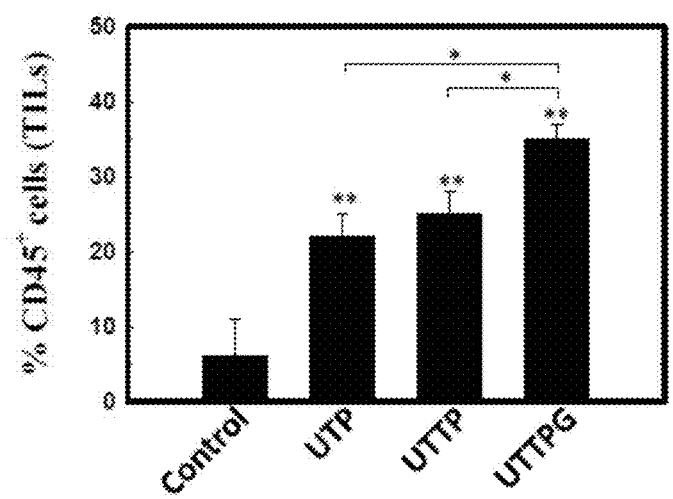
FIG. 7A-(b)

FIG. 7A-(c)
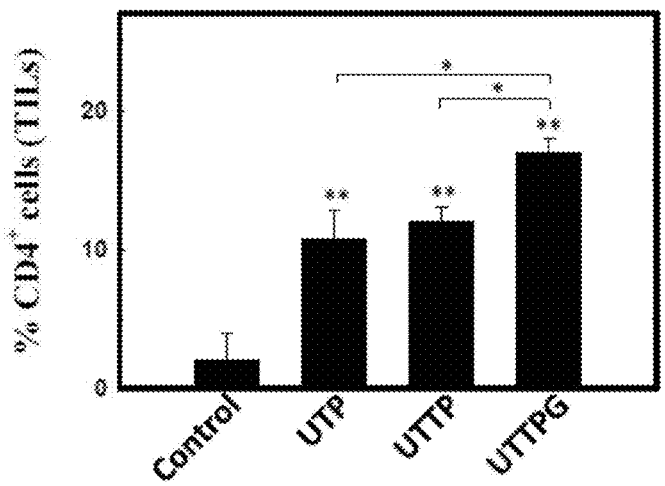
FIG. 7A-(d)
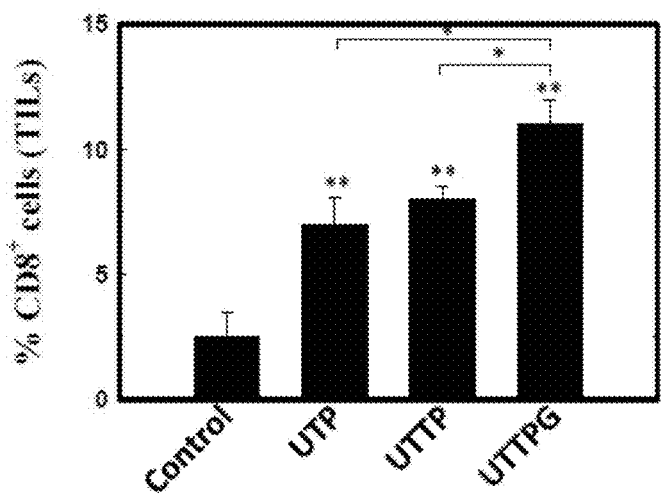
FIG. 7B-(a)
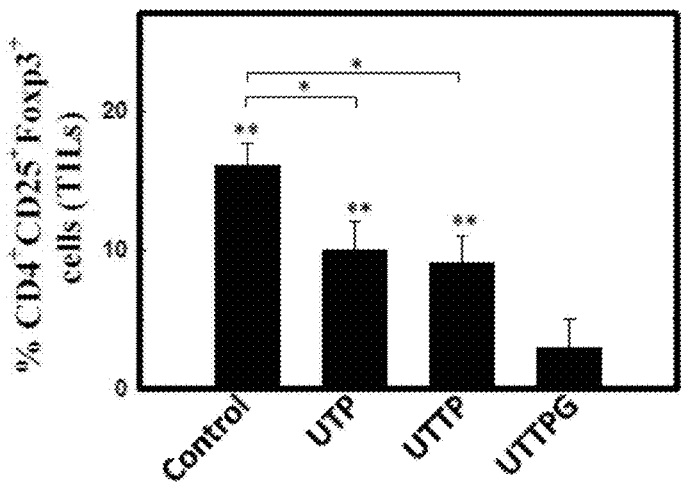

FIG. 7B-(b)
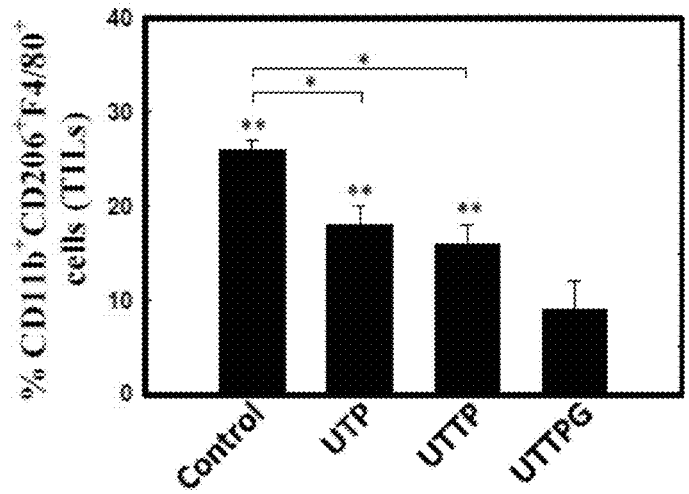
FIG. 7C-(a)
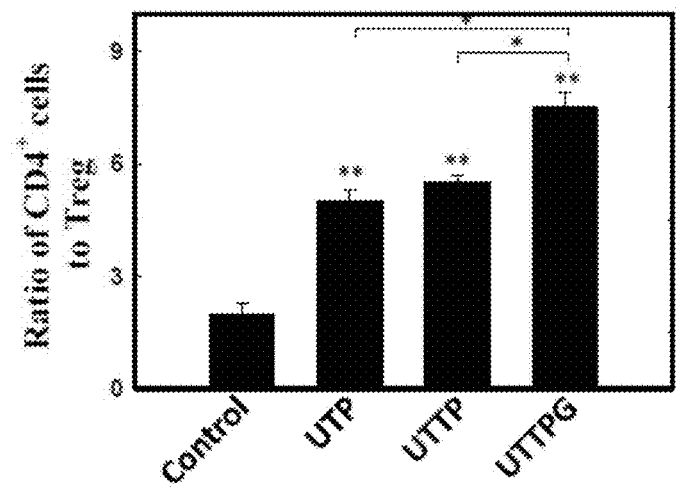
FIG. 7C-(b)
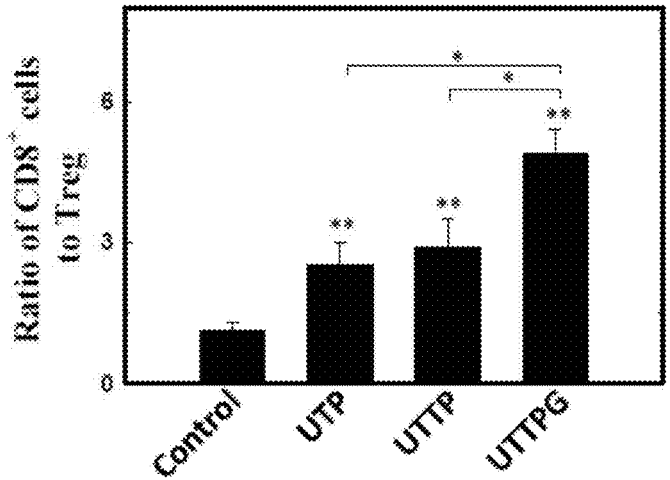

FIG. 7C-(c)
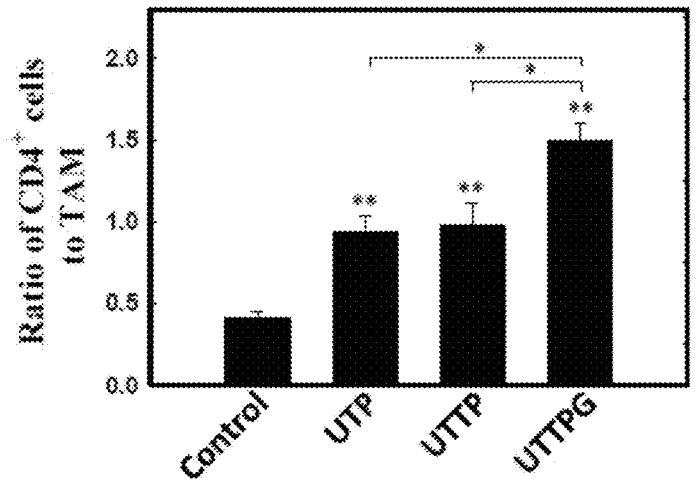
FIG. 7C-(d)
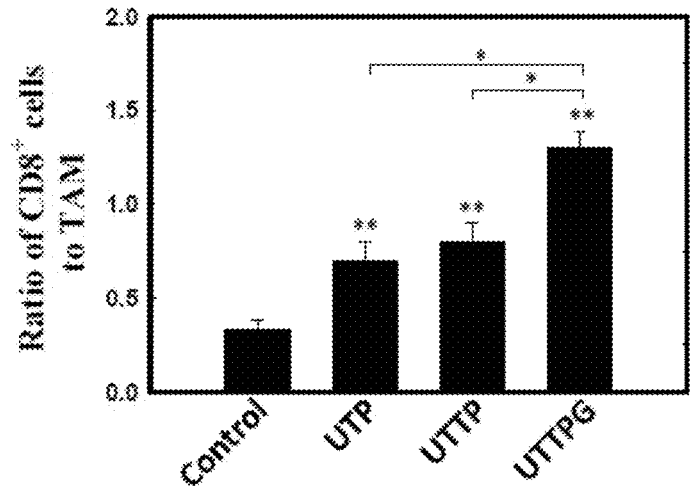
FIG. 7D-(a)
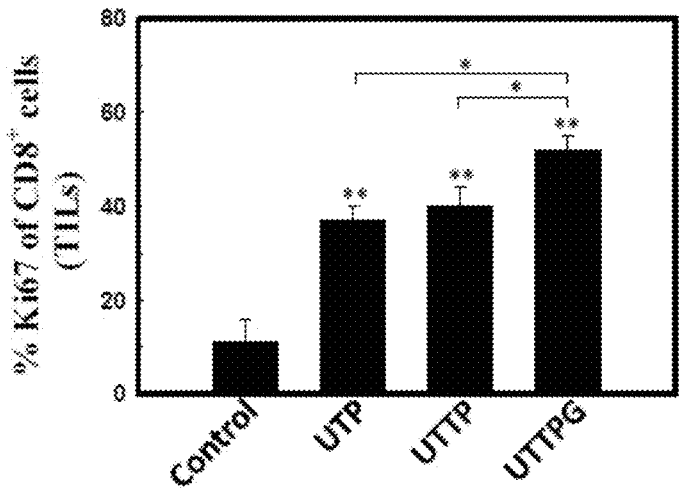

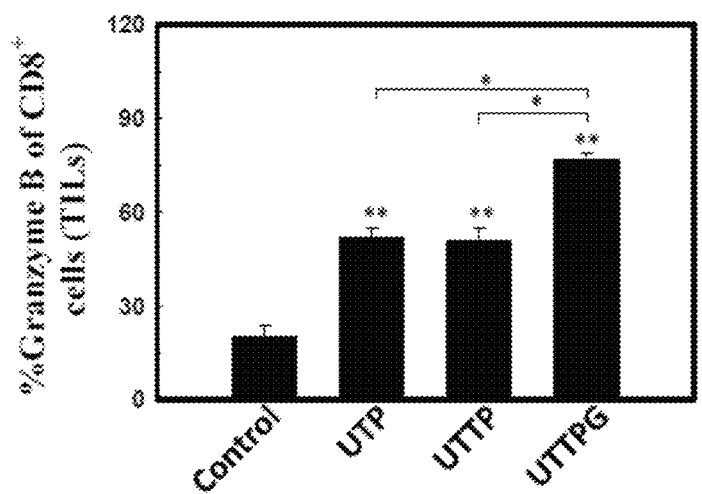
FIG. 7D-(b)

SEQUENCE LISTING

<160> NUMBER OF SEQ ID NOS: 5

<210> SEQ ID NO 1
<211> LENGTH: 1131
<212> TYPE: DNA
<213> ORGANISM: herpes simplex virus

<400> SEQUENCE: 1

```
atggcctcgt acccccggcca tcaacacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg gccctgggtt cgcgcgacga tatcgtctac     240
gtacccgagc cgatgactta ctggcgggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg ggggggaggc tgggagctca catgccccgc cccggccct caccctcatc     480 ttcgaccgcc atcccatcgc cgccctcctg tgctaccggc ccgcgcggta ccttatgggc     540
agcatgaccc cccaggccgt gctggcgttc gtggccctca tcccgccgac cttgcccggc     600
accaacatcg tgcttgggc ccttccggag gacagacaca tcgaccgcct ggccaaacgc     660
cagcgccccg gcgagcggct ggacctggct atgctggctg cgattcgccg cgtttacggg     720
ctacttgcca atacggtgcg gtatctgcag tgcgcgggt cgtggcggga ggactgggga     780
cagctttcgg ggacggccgt gccgccccag ggtgccgagc ccagagcaa cgcgggccca     840
```

| | |
|---|---|
| cgaccccata tcggggacac gttatttacc ctgtttcggg ccccgagtt gctggccccc | 900 |
| aacggcgacc tgtataacgt gtttgcctgg gccttggacg tcttggccaa acgcctccgt | 960 |
| tccatgcacg tctttatcct ggattacgac caatcgcccg ccggctgccg ggacgccctg | 1020 |
| ctgcaactta cctccgggat ggtccagacc cacgtcacca ccccggctc ataccgacg | 1080 |
| atatgcgacc tggcgcgcac gtttgcccgg gagatggggg aggctaactg a | 1131 |

<210> SEQ ID NO 2
<211> LENGTH: 1131
<212> TYPE: DNA
<213> ORGANISM: herpes simplex virus

<400> SEQUENCE: 2

| | |
|---|---|
| atggcttctt accctggaca ccagcatgct tctgcctttg accaggctgc cagatccagg | 60 |
| ggccactcca acaggagaac tgccctaaga cccagaagac agcaggaagc cactgaggtg | 120 |
| aggcctgagc agaagatgcc aaccctgctg agggtgtaca ttgatggacc tcatggcatg | 180 |
| ggcaagacca ccaccactca actgctggtg gcactgggct ccaggatga cattgtgtat | 240 |
| gtgcctgagc caatgaccta ctggagagtg ctaggagcct ctgagaccat tgccaacatc | 300 |
| tacaccaccc agcacaggct ggaccaggga gaaatctctg ctggagatgc tgctgtggtg | 360 |
| atgacctctg cccagatcac aatgggaatg ccctatgctg tgactgatgc tgttctggct | 420 |
| cctcacattg gaggagaggc tggctcttct catgcccctc cacctgccct gaccctgatc | 480 |
| tttgacagac accccattgc agccctgctg tgctacccag cagcaaggta cctcatgggc | 540 |
| tccatgaccc cacaggctgt gctggctttt gtggccctga tccctccaac cctccctggc | 600 |
| accaacattg ttctgggagc actgcctgaa acagacaca ttgacaggct ggcaaagagg | 660 |
| cagagacctg gagagagact ggacctggcc atgctggctg caatcagaag ggtgtatgga | 720 |
| ctgctggcaa acactgtgag atacctccag tgtggaggct cttggagaga ggactgggga | 780 |
| cagctctctg gaacagcagt gccccctcaa ggagctgagc ccagtccaa tgctggtcca | 840 |
| agaccccaca ttggggacac cctgttcacc ctgttcagag cccctgagct gctggctccc | 900 |
| aatggagacc tgtacaatgt gtttgcctgg gctctggatg ttctagccaa gaggctgagg | 960 |
| tccatgcatg tgttcatcct ggactatgac cagtcccctg ctggatgcag agatgctctg | 1020 |
| ctgcaactaa cctctggcat ggtgcagacc catgtgacca cccctggcag catccccacc | 1080 |
| atctgtgacc tagccagaac cttttgccagg gagatgggag aggccaacta a | 1131 |

<210> SEQ ID NO 3
<211> LENGTH: 864
<212> TYPE: DNA
<213> ORGANISM: Homo sapiens

<400> SEQUENCE: 3

| | |
|---|---|
| atgcagatcc cacaggcgcc ctggccagtc gtctgggcgg tgctacaact gggctggcgg | 60 |
| ccaggatggt tcttagactc cccagacagg ccctggaacc ccccaccctt ctccccagcc | 120 |
| ctgctcgtgg tgaccgaagg ggacaacgcc accttcacct gcagcttctc caacacatcg | 180 |
| gagagcttcg tgctaaactg gtaccgcatg agccccagca accagacgga caagctggcc | 240 |
| gctttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aaggcgcaga tcaaagagag cctgcgggca | 420 |
| gagctcaggg tgacagagag aagggcagaa gtgcccacag cccaccccag cccctcaccc | 480 |

| | |
|---|---|
| aggccagccg gccagttcca aaccctggtg gttggtgtcg tgggcggcct gctgggcagc | 540 |
| ctggtgctgc tagtctgggt cctggccgtc atctgctccc gggccgcacg agggacaata | 600 |
| ggagccaggc gcaccggcca gcccctgaag gaggacccct cagccgtgcc tgtgttctct | 660 |
| gtggactatg gggagctgga tttccagtgg cgagagaaga ccccggagcc ccccgtgccc | 720 |
| tgtgtccctg agcagacgga gtatgccacc attgtctttc ctagcggaat gggcacctca | 780 |
| tcccccgccc gcaggggctc agccgacggc cctcggagtg cccagccact gaggcctgag | 840 |
| gatggacact gctcttggcc cctc | 864 |

<210> SEQ ID NO 4
<211> LENGTH: 603
<212> TYPE: DNA
<213> ORGANISM: Homo sapiens

<400> SEQUENCE: 4

| | |
|---|---|
| atggcctgga tgctgttgct catcttgatc atggtccatc caggatcctg tgctctctgg | 60 |
| gtgtcccagc cccctgagat tcgtaccctg aaggatcct ctgccttcct gccctgctcc | 120 |
| ttcaatgcca gccaagggag actggccatt ggctccgtca cgtggttccg agatgaggtg | 180 |
| gttccaggga aggaggtgag gaatggaacc ccagagttca ggggccgcct ggccccactt | 240 |
| gcttcttccc gtttcctcca tgaccaccag gctgagctgc acatccggga cgtgcgaggc | 300 |
| catgacgcca gcatctacgt gtgcagagtg gaggtgctgg gccttggtgt cgggacaggg | 360 |
| aatgggactc ggctggtggt ggagaaagaa catcctcagc taggggctgg tacagtcctc | 420 |
| ctccttcggg ctggattcta tgctgtcagc tttctctctg tggccgtggg cagcaccgtc | 480 |
| tattaccagg gcaaatgtct gacctggaaa ggtccaagaa ggcagctgcc ggctgtggtc | 540 |
| ccagcgcccc tcccaccacc atgtgggagc tcagcacatc tgcttccccc agtcccagga | 600 |
| ggc | 603 |

<210> SEQ ID NO 5
<211> LENGTH: 843
<212> TYPE: DNA
<213> ORGANISM: Homo sapiens

<400> SEQUENCE: 5

| | |
|---|---|
| atggctatga tggaggtcca ggggggaccc agcctgggac agacctgcgt gctgatcgtg | 60 |
| atcttcacag tgctcctgca gtctctctgt gtggctgtaa cttacgtgta ctttaccaac | 120 |
| gagctgaagc agatgcagga caagtactcc aaaagtggca ttgcttgttt cttaaaagaa | 180 |
| gatgacagtt attgggaccc caatgacgaa gagagtatga acagcccctg ctggcaagtc | 240 |
| aagtggcaac tccgtcagct cgttagaaag atgattttga gaacctctga ggaaccatt | 300 |
| tctacagttc aagaaaagca acaaaatatt ctcccctag tgagagaaag aggtcctcag | 360 |
| agagtagcag ctcacataac tgggaccaga ggaagaagca cacattgtc ttctccaaac | 420 |
| tccaagaatg aaaaggctct gggccgcaaa ataaactcct gggaatcatc aaggagtggg | 480 |
| cattcattcc tgagcaactt gcacttgagg aatggtgaac tggtcatcca tgaaaaggg | 540 |
| ttttactaca tctattccca acatacttt cgatttcagg aggaaataaa agaaacaca | 600 |
| aagaacgaca acaaatggt ccaatatatt tacaaataca caagttatcc tgaccctata | 660 |
| ttgttgatga aaagtgctag aaatagttgt tggtctaaag atgcagaata tggactctat | 720 |
| tccatctatc aagggggaat atttgagctt aaggaaaatg acagaatttt tgtttctgta | 780 |

```
acaaatgagc acttgataga catggaccat gaagccagtt ttttcggggc cttttagtt    840 ggc                                                                 843
```

US 11,458,171 B2

ENGINEERING STEM CELLS FOR CANCER THERAPY

This application claims priority to U.S. Provisional Application No. 62/646,014, filed Mar. 21, 2018 entitled "ENGINEERING MESENCHYMAL STEM CELLS FOR CANCER THERAPY", which is incorporated by reference in its entirety.

The instant application contains a Sequence Listing which has been submitted electronically in ASCII format and is hereby incorporated by reference in its entirety. Said ASCII copy, created on DATE, is named G4590-04700 SL.txt and is 7 KB in size.

FIELD OF THE INVENTION

The present invention relates to engineered stem cells for the treatment of cancer. Particularly, the engineered stem cells comprise at least a suicide gene and an immune checkpoint gene.

BACKGROUND OF THE INVENTION

Checkpoint immunotherapy by interacting with PD-1/PD-L1 pathway is at the cutting age of cancer treatment, and giving hope for a cure of cancer. The protein encoded by this gene is a natural cytotoxicity receptor (NCR3) that may aid NK cells in the lysis of tumor cells. However, up to 70% of patients do not respond to the treatment, which even causes severe complications in some clinical cases (The Journal of Clinical Endocrinology & Metabolism 2013, 98(4): 1361-1375). There is urgent need for improvement such that the inhibitors are able to selectively accumulate within tumors and not cause autoimmune responses in the peripheral normal tissue.

US20180214544 provides a combination of immune checkpoint blockade and hematopoietic stem cell transplantation and/or hematopoietic stem cell mobilization yielding synergistic effects in disease therapy. However, a need continues to exist for improving the effect of immune checkpoint inhibitors.

SUMMARY OF THE INVENTION

The present disclosure provides an engineered stem cell, comprising a vector comprising a polynucleotide comprising a nucleic acid sequence of suicide gene, a nucleic acid sequence of immune checkpoint gene and a natural cytotoxicity triggering receptor or a TNF-related apoptosis-inducing ligand, wherein the stem cell is a tumor-targeting cell.

Certain embodiments of the engineered stem cell include embryonic stem cell, marrow stromal cell, hematopoietic stem cell and neural stem cell. A particular embodiment of the engineered stem cell is MSC. A further particular embodiment of the engineered stem cell is umbilical cord mesenchymal stem cell (UMSC).

Certain embodiments of the suicide gene include cytosine deaminase gene, varicella-zoster virus thymidine kinase gene, nitroreductase gene, *Escherichia coli* gpt gene, *E. coli* Deo gene, thymidine kinase gene (TK), caspase 1, caspase 3, caspase 6, caspase 7, caspase 8, caspase 9 and Fas or cytosine deaminse (CD).

Certain embodiments of the immune checkpoint gene include the E3 ubiquitin ligase Cbl-b. CTLA-4. PD-1, TIM-3, killer inhibitory receptor (KIR), LAG-3, CD73, Fas, the aryl hydrocarbon receptor, Smad2, Smad4, TGF-beta receptor, ILT-3, IDO, KIR, and LAG3.

Certain embodiments of the natural cytotoxicity triggering receptor include NCR1, NCR2 and NCR3.

A certain embodiment of the TRAIL gene includes TIC10.

The present disclosure provides a kit or combination comprising the vector or engineered cell of the present disclosure and optionally an additional active agent.

The present disclosure also provides a method for treating a cancer or enhancing intratumor immunity in a subject, comprising administering an effective amount of the engineered stem cell of the present disclosure to the subject. In one embodiment, the effective amount ranges from 100,000 ($1\times10^5$) 2,000,000 ($2\times10^6$) cells. In one embodiment, the cancer is a metastatic cancer.

BRIEF DESCRIPTION OF THE DRAWING

The patent of application file contains at least one drawing executed in color. Copies of this patent or patent application publication with color drawing(s) will be provided by the Office upon request and payment of the necessary fees.
FIGS. 1A to G show in vitro characterization of UMSCs and UMSC-TRAIL-TK-PD-1. FIG. 1A. The cell morphology and biological properties of umbilical cord mesenchymal stem cells (UMSCs) from Wharton's jelly (WJ). FIG. 1B. The flow cytometry plots show the cells are negative for CD1q, CD3, CD10, CD14, CD31, CD34, CD45, CD49d, CD56, CD117 and HLA-DR, but positive for CD13, CD29, CD44, CD73, CD90, CD105, CD166, CD49b and HLA-ABC. FIG. 1C. The results of RFP and PD-1 flowcytometry and transduction with the transgenes (UMSC-PD-1 and UMSC-TRAIL-TK-PD-1). FIG. 1D. UMSC-TRAIL-TK-PD-1-Luc retains luciferase expression more than 100 days and FIG. 1E cell proliferation assay by BrdU incorporation and migration by transwell assay reveal that genetic modification does not affect the UMSC-TRAIL-TK-PD-1 cellular viability (FIG. 1E-(a)), cell proliferation (FIG. 1E-(b)) or migration (FIG. 1E-(c)) in vitro compared to unlabeled UMSCs after 14 h of incubation. FIG. 1F. The UMSC-TRAIL-TK-PD-1 displays similar behavior to the plain UMSCs without plasmids labeling. FIG. 1G. The UMSC-TRAIL-TK-PD-1's neuroglial cell differentiation was identified by immunofluorescence with MAP-2, Tuj-1 and GFAP; the results exhibited refractile cell body morphology with extended neurite-like structures arranged into a network as the plain UMSCs.

FIGS. 2A to D show immunological assessment of UMSC-TRAIL-TK-PD-1 in vitro. FIG. 2A. The binding affinity of HRP-conjugated PD-1 protein is increased significantly in a dose-dependent manner. FIG. 2B. The gating strategy is based on the justification of first gate, exclusion of doublets by FSC-A and FSC-H, exclusion of dead cells by selection of 7-AAD$^+$ (R&D systems)/CD45$^+$ or FSC-A (FIG. 2B-(a) and FIG. 2B-(b)). FIG. 2C. UMSCs (at a ratio of 1:1) significantly suppress both CD4$^+$ and CD8$^+$ T-cell proliferation (FIG. 2C-(a) and FIG. 2C-(b)). However, at a ratio of either 1:1 or 1:10, UMSC-TRAIL-TK-PD-1 significantly increased both CD4$^+$ and CD8$^+$ T-cell proliferation (FIG. 2C-(a) and FIG. 2C-(b)). FIG. 2D. UMSC-TRAIL-TK-PD-1 stimulated with CD3-CD28 exhibits significant increase level of CD4$^+$INF-$\gamma^+$ (FIG. 2D-(a)) and reduction of CD8$^+$CD122$^+$ (FIG. 2D-(b)) compared to that of UMSCs.

FIGS. 3A to E show suicide and bystander effect of UMSC-TRAIL-TK-PD-1-GFP in vitro. FIG. 3A. Increased level of TK is found in the UMSC-TRAIL-TK-PD-1 compared to UMSC-Akt and UMSCs by Western blot. FIG. 3B.

GCV itself does not affect cell proliferation of UMSCs. Phosphorylated GCV induces apoptotic-like cell injury in UMSC-TRAIL-TK-PD-1-GFP at 24 h and 48 h after GCV treatment by immunohistochemistry (white arrow) (FIG. 3B-(b)). Cell proliferation of UMSC-TRAIL-TK-PD-1-GFP is inhibited in a dose-dependent manner (FIG. 3B-(a)). FIG. 3C. UMSC-TRAIL-TK-PD-1-GFP significantly attenuates the growth of 4T1-Luc cells ((FIG. 3C-(a), FIG. 3C-(b)) (Hep55.1C (FIG. 3C-(c) and FIG. 3C-(d)), Pan18-Luc (FIG. 3C-(e) and FIG. 3C-(f)), CT26-Luc (FIG. 3C-(g) and FIG. 3C-(h)) and GL261-Luc (FIG. 3C-(i) and FIG. 3C-(j)) with the presence of 0, 1, 10, 100 μg/mL GCV after co-culture for 24 h, 48 h and 72 h. FIG. 3D-E. Cell mortality rate by suicide effect in this co-culture system slowly reaches about one-third of the whole system during the first two days, and then subsequently accelerates from day 3 to day 6. The same findings show that most 4T1-Luc cells are killed from day 3 to day 5. Furthermore, quantitative assessment of apoptotic cells under this bystander effect by PI/annexin-V staining using flowcytometry shows significant cytotoxicity in a GCV dose-dependent and time-dependent manner FIG. 3 (E-(a) to FIG. 3E-(d)). FIGS. 4A to C show UMSC-TRAIL-TK-PD-1 expressing TRAIL display in vitro antitumor activity in 4T1-luc and Hep55.1C-Luc cell. FIG. 4A. Genetically modified UMSC-TRAIL-TK-PD-1 allows a relevant TRAIL protein expression (90%) on the cell surface of UMSCs as measured by FACS analysis. FIG. 4B. UMSC-TRAIL-TK-PD-1 expressing TRAIL induces cell apoptosis (4T1-Luc, Hep55.1C-Luc), represented by cell shrinkage, reduction of adherent 4T1-Luc cells (FIG. 4B-(a)) and Hep55.1C-Luc (FIG. 4B-(b)) with the appearance of cellular debris, which were demonstrated by the propidium iodine staining (PI staining) (FIG. 4B-(c)), especially at 72 hours after coculture. FIG. 4C. Quantitatively, cell death occurred at 24, 48 and 72 hours (FIG. 4C-(a) and FIG. 4C-(b)), a large amount of Annexin-$V^+PI^+$ dead cells (≥70%) were detected in coculture where UMSC-TRAIL-TK-PD-1 is present in a dose-dependent manner as measured by FACS analysis.

FIG. 5A. Bioilluminance intensity increased in a UMSC-TRAIL-TK-PD-1-Luc cell dose-dependent manner as measured by IVIS in vitro. FIG. 5B. UMSC-TRAIL-TK-PD-1-Luc survives and relocates to the subcutaneous 4T1 tumors. The bioluminescent signal of the subcutaneous tumor area in IVIS image was observed initially at five days after intravenous UMSC-TRAIL-TK-PD-1-Luc injection, gradually increased intensity afterward, and peaked at day 14. FIG. 5C-E. Intraarterial UMSC-TRAIL-TK-PD-1-Luc transplantation is directly recruited to the orthotopic 4T1 tumor region (FIG. 5C) (also for Hep55.1C (FIG. 5D) and pan18 tumor region (FIG. 5E) at two hours after intra-femoral artery injection without lung entrapment. Subsequently, UMSC-TRAIL-TK-PD-1-Luc survives and relocates to the tumors sites. FIG. 5F. Metastatic tumor from original 4T1-tumor model significantly recruits the UMSC-TRAIL-TK-PD-1-Luc to increase the bioilluminance intensity as measured by IVIS in the multiple metastatic sites. FIG. 5G. By immunohistochemical analysis, numerous $GFP^+$ Luciferase$^+$ cells was found in the 4T1 tumor at one day after treatment, which indicated UMSC-TRAIL-TK-PD-1-GFP were recruited into tumor microenvironment.

FIGS. 6A to G show the therapeutic effect of UMSC-TRAIL-TK-PD-1 in 4T1-Luc model. FIG. 6A. The tumoricidal effects in luciferase-expressing 4T1-Luc- and Hep55.1C-Luc-tumor-bearing mice treated with various strategies of gene modified UMSCs are assessed by IVIS, tumor volume and survival time following the q4dx3 course of treatment protocol. FIG. 6B. Prior to treatment, every group of tested cells is subjected to hypoxia preconditioning culture in 3% $O_2$, which induced CXCR4 overexpression by Western blot for enhancing stem cell homing in a time-dependent manner. FIG. 6C. UMSC-PD-1 (UP) group and UMSC-TRAIL (UT) group exhibit a therapeutic effect, reducing tumor volumes compared to those in the IgG control group as measured by IVIS. Moreover, the UMSC-TK-PD-1+GCV (UTPG) group, UMSC-TRAIL-TK+GCV (UTTG) group, and UMSC-TRAIL-PD-1 (UTP) group showed stronger antitumoral effects and exhibited inhibition of tumor growth respectively. FIG. 6D. Intravenous UTP significantly extends survival time on both 4T1 and Hempa55.1C model compared to the other groups FIG. 6 (D-(a) to FIG. 6D-(d)). FIG. 6E. Fewer than 5 nodules of lung metastasis were discovered in UTP-treated mice compared to over 20 metastases in lungs of the control mice. However, UMSC-TK (UT), UP and UTP did not show a significant decrease in metastasis compared to the control group. FIG. 6F-G. Next, to verify whether intra-arterial injection of UMSC-TRAIL-TK-PD-1 displayed a significant robust therapeutic effect in 4T1-Luc and Hep55.1C-Luc model following the q7dx2 course of treatment protocol, four groups (UMSC-TK-PD-1+GCV (UTPG) group, UMSC-TRAIL-TK-PD-1 (UTTP) group, and UMSC-TRAIL-TK-PD-1+GCV (UTTPG) group) were divided to examine the tumor growth and median survival time (FIG. 6F-(a)). Before the analysis of intra-arterial injection, intravenous administration of UMSC-TRAIL-TK-PD-1+GCV (UTTPG) group showed stronger antitumoral effects (FIG. 6F-(b)) than the other groups of IgG control, UTPG and UTTP, respectively. Importantly, intra-arterial implantation revealed a robustly superior therapeutic effect to the intravenous ones. Moreover, the UTTPG group significantly inhibit tumor growth and enhance the median survival times of the mice than the other groups of IgG control, UTPG and UTTP in 4T1-Luc (FIG. 6F-(c-d)) and Hep55.1C-Luc (FIG. 6G-(a-b)) model, respectively. Unfortunately, administration anti-PD-L1 did not show any significantly therapeutic effect in 4T1-Luc model (FIG. 6F-(c)).

FIGS. 7A to D how UTTPG treatment enhances immunity in the tumor microenvironment (TME). A. The gating strategy is based on the justification of first gate, exclusion of doublets by FSC-A and FSC-H, exclusion of dead cells by selection of 7-AAD$^+$ (R&D systems)/CD45$^+$ or FSC-A (FIG. 7A-(a)). There was an overall increase in the percentage of tumor-infiltrating CD45$^+$ leukocytes across the therapeutic groups of UTTPG and the other therapeutic groups (FIG. 7A-(b)). The frequencies for both CD3$^+$CD8$^+$ and CD3$^+$CD4$^-$ T cells are significantly enhanced in UTTPG treatment compared to the other groups (FIG. 7A-(c) and FIG. 7A-(d)). B-C. UTTPG induces a significant reduction in Tregs and TAMs (FIG. 7B-(a) and FIG. 7B-(b)), and thereby reverses the ratio of CD8$^+$ (FIG. 7C-(b)) and CD4$^+$ (FIG. 7C-(a)) T cells to Tregs within the tumors. Additionally, the number of TAMs dramatically decrease in response to UTTPG treatment, which increases the ratio of CD8$^+$ (FIG. 7C-(d)) and CD4$^+$ (FIG. 7C-(c)) T cells to TAMs in the TME. D. The marked upregulation in intracellular granzyme B (Grb$^+$) (FIG. 7D-(b)) and Ki67$^+$ (FIG. 7D-(a)) cells indicates that UTTPG treatment not only increases the antitumor immune population but also effectively achieves activation and proliferation of TILs.

DETAILED DESCRIPTION OF THE INVENTION

Figure 1A:
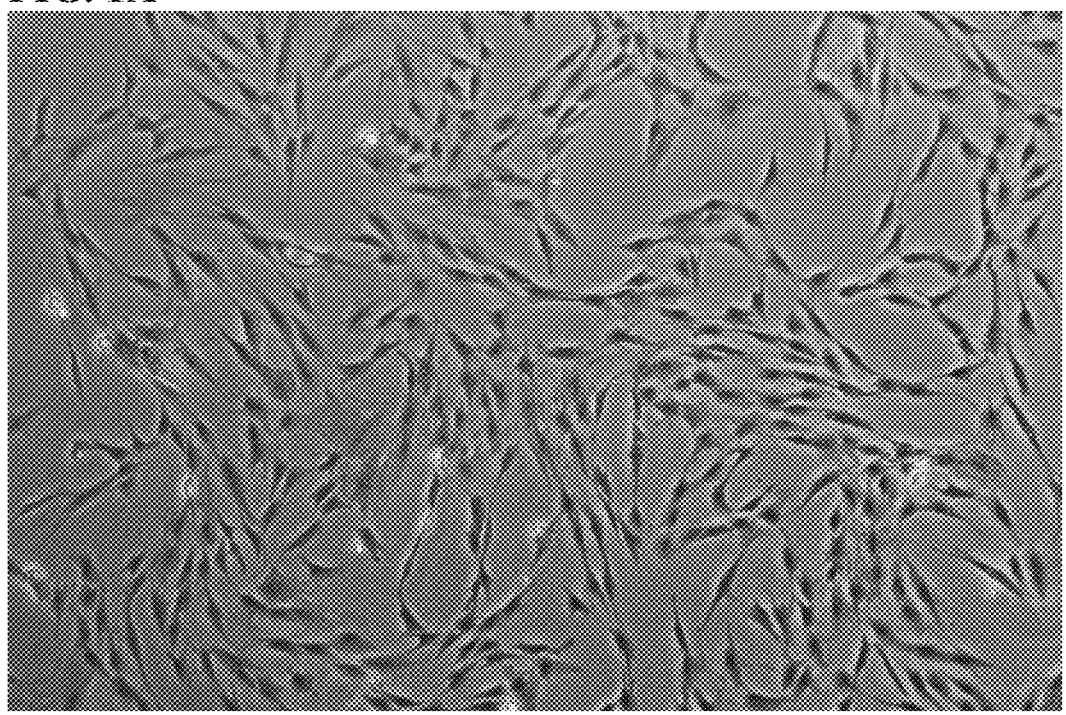

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

As used herein, the terms "a," "an," "the" and similar references can be construed to cover both the singular and the plural.

As used herein, the term "genetically modified cells," "redirected cells," "genetically engineered cells" or "modified cells" refer to cells that express the recombinant polynucleotide of the invention.

The terms "polynucleotide," "nucleic acid" and "oligonucleotide" are used interchangeably herein to refer to a polymeric form of nucleotides of any length, either deoxyribonucleotides or ribonucleotides or analogs thereof.

As used herein, the term "gene" refers to a polynucleotide containing at least one open reading frame (ORF) that is capable of encoding a particular polypeptide or protein after being transcribed and translated.

As used herein, the term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

As used herein, the term "expression" refers to the process by which polynucleotides are transcribed into mRNA and/or the process by which the transcribed mRNA is subsequently translated into peptides, polypeptides, or proteins.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or be in an in vitro expression system.

As used herein, the term "thymidine kinase" or "TK" means the thymidine kinase suicide gene "TK" that is known in the art to provide biosafety to recombinant vectors. Unless specified otherwise, the term "TK" means wild-type (WT) and/or mutant forms of the gene known in the art.

As used herein, the term "marrow stromal cell," also referred to as "mesenchymal stem cells," or MSC, is a multipotent stem cell that can differentiate into a variety of cell types.

As used herein, the term "subject," "individual" or "patient" is used interchangeably, and refers to a vertebrate, preferably a mammal, more preferably a human.

As used herein, the term "treatment" or "treating" should be understood to include any indicia of success in the treatment, alleviation or amelioration of an injury, pathology or condition. This may include parameters such as abatement, remission, diminishment of symptoms, slowing in the rate of degeneration or decline, making the final point of degeneration less debilitating; improving a patient's physical or mental well-being; or preventing the onset of disease.

As used herein, the term "therapeutically effective amount" when used in reference to symptoms of a disease/condition refers to the amount and/or concentration of a compound that ameliorates, attenuates, or eliminates one or more symptoms of a disease/condition or prevents or delays the onset of a symptom(s).

Mesenchymal stem cells (MSCs) are regarded as a cellular vehicle for the expression of therapeutic proteins by gene transfer and show a unique tumor-homing tropism for targeted delivery of anticancer substances to animal models of various tumors, including melanoma, glioblastoma, and breast cancer. There are several advantages, such as easy isolation and expansion, immunotolerant property, and systemic or local delivery. Although current genetic engineering methods by viral transduction of DNA to MSCs can be applied as diagnostic and therapeutic strategies for cancer treatment, they might induce detrimental transformation to increase secondary malignancy risk.

It is imperative to test whether MSC could represent an efficient vehicle to deliver genetic material for anti-cancer function. Tumor necrosis factor (TNF)-related apoptosis-inducing ligand (TRAIL), which is a promising anticancer death ligand with a sequence homology to TNF and FasL, could mediate the apoptotic effect by binding to its death receptors (DR), as homotrimer, particularly on TRAIL-R1/DR4 and TRAIL-R2/DR5 activation, a protein complex, causes caspase-8 activation, triggering apoptosis (Nat Rev Cancer 2008; 8:782-98; Science 1998; 281:1305-8; Eur J Cancer 2006; 42:2233-40). Furthermore, suicide gene therapy is based on transferring a gene encoding a suicide protein of herpes simplex virus thymidine kinase (HSV-TK), which selectively sensitizes it to the prodrug ganciclovir (GCV) by preferential monophosphorylation of nontoxic GCV into a toxic compound through the viral TK enzyme (Mol Biol Cell 2002; 13:4279-95). Chimeric antigen receptor-T cell (CAR-T) immunotherapy combined with suicide gene modification has been demonstrated to not only inhibit tumor outgrowth but improve the safety profile to facilitate clinical development (Journal of Cancer 2011; 2:378-382).

It has not been verified whether PD-1- or NCR3-overexpressed MSCs will enhance migration into tumors and immune sensitization, induce tumor death as well as reduce inflammation. The present disclosure develops a natural nanoparticle harboring inherent anti-tumor ability to play an important task in therapeutic gene engineering.

In one aspect, the present disclosure provides an engineered stem cell, comprising a vector comprising a polynucleotide comprising a nucleic acid sequence of suicide gene, a nucleic acid sequence of immune checkpoint gene and a natural cytotoxicity triggering receptor or a TNF-related apoptosis-inducing ligand; wherein the stem cell is a tumor-targeting cell.

In one embodiment, the tumor-targeting cell is a stem cell selected from the group consisting of: embryonic stem cell, marrow stromal cell, hematopoietic stem cell and neural stem cell.

In one embodiment, the stem cell is MSC. In one embodiment the MSC has the phenotype $CD34^-/CD45^-/CD105^+/CD90^+/CD73^+$. MSCs have been shown differentiation in vitro or in vivo, including osteoblasts, chondrocytes, myocytes, and adipocytes. Mesenchyme is embryonic connective tissue that is derived from the mesoderm and that differentiates into hematopoietic and connective tissue, whereas MSCs do not differentiate into hematopoietic cells.

Stromal cells are connective tissue cells that form the supportive structure in which the functional cells of the tissue reside.

A suicide gene, in genetics, will cause a cell to kill itself through apoptosis. In some embodiments, the suicide gene is cytosine deaminase gene, varicella-zoster virus thymidine kinase gene, nitroreductase gene, *Escherichia coli* gpt gene, *E. coli* Deo gene, thymidine kinase gene (TK), caspase 1, caspase 3, caspase 6, caspase 7, caspase 8, caspase 9, Fas or cytosine deaminse (CD). In a certain embodiment, the suicide gene is thymidine kinase gene. In one embodiment, the TK gene is a wild-type TK gene. In another embodiment, the TK gene is a mutated form of the gene. In some embodiments, the thymidine kinase sequence includes, but is not limited to, the following sequences.

```
HSV1-TK sequence
                                            (SEQ ID NO: 1)
ATGGCCTCGTACCCCGGCCATCAACACGCGTCTGCGTTCGACCAGGCTGC

GCGTTCTCGCGGCCATAGCAACCGACGTACGGCGTTGCGCCCTCGCCGGC

AGCAAGAAGCCACGGAAGTCCGCCCGGAGCAGAAAATGCCCACGCTACTG

CGGGTTTATATAGACGGTCCCCACGGGATGGGGAAAACCACCACCACGCA

ACTGCTGGTGGCCCTGGGTTCGCGCGACGATATCGTCTACGTACCCGAGC

CGATGACTTACTGGCGGGTGCTGGGGCTTCCGAGACAATCGCGAACATC

TACACCACACAACACCGCCTCGACCAGGGTGAGATATCGGCCGGGGACGC

GGCGGTGGTAATGACAAGCGCCCAGATAACAATGGGCATGCCTTATGCCG

TGACCGACGCCGTTCTGGCTCCTCATATCGGGGGGAGGCTGGGAGCTCA

CATGCCCGCCCCGGCCCTCACCCTCATCTTCGACCGCCATCCCATCGC

CGCCCTCCTGTGCTACCCGGCCGCGCGGTACCTTATGGGCAGCATGACCC

CCCAGGCCGTGCTGGCGTTCGTGGCCCTCATCCCGCCGACCTTGCCCGGC

ACCAACATCGTGCTTGGGGCCCTTCCGGAGGACAGACACATCGACCGCCT

GGCCAAACGCCAGCGCCCCGGCGAGCGGCTGGACCTGGCTATGCTGGCTG

CGATTCGCCGCGTTTACGGGCTACTTGCCAATACGGTGCGGTATCTGCAG

TGCGGCGGGTCGTGGCGGGAGGACTGGGGACAGCTTTCGGGGACGGCCGT

GCCGCCCCAGGGTGCCGAGCCCCAGAGCAACGCGGGCCCACGACCCCATA

TCGGGGACACGTTATTTACCCTGTTTCGGGCCCCCGAGTTGCTGGCCCCC

AACGGCGACCTGTATAACGTGTTTGCCTGGGCCTTGGACGTCTTGGCCAA

ACGCCTCCGTTCCATGCACGTCTTTATCCTGGATTACGACCAATCGCCCG

CCGGCTGCCGGGACGCCCTGCTGCAACTTACCTCCGGGATGGTCCAGACC

CACGTCACCACCCCCGGCTCCATACCGACGATATGCGACCTGGCGCGCAC

GTTTGCCCGGGAGATGGGGGAGGCTAACTGA

CpG free HSV1-TK sequence
                                            (SEQ ID NO: 2)
ATGGCTTCTTACCCTGGACACCAGCATGCTTCTGCCTTTGACCAGGCTGC

CAGATCCAGGGGCCACTCCAACAGGAGAACTGCCCTAAGACCCAGAAGAC

AGCAGGAAGCCACTGAGGTGAGGCCTGAGCAGAAGATGCCAACCCTGCTG

AGGGTGTACATTGATGGACCTCATGGCATGGGCAAGACCACCACCACTCA

ACTGCTGGTGGCACTGGGCTCCAGGGATGACATTGTGTATGTGCCTGAGC

CAATGACCTACTGGAGAGTGCTAGGAGCCTCTGAGACCATTGCCAACATC

TACACCACCCAGCACAGGCTGGACCAGGGAGAAATCTCTGCTGGAGATGC

TGCTGTGGTGATGACCTCTGCCCAGATCACAATGGGAATGCCCTATGCTG

TGACTGATGCTGTTCTGGCTCCTCACATTGGAGGAGAGGCTGGCTCTTCT

CATGCCCCTCCACCTGCCCTGACCCTGATCTTTGACAGACACCCCATTGC

AGCCCTGCTGTGCTACCCAGCAGCAAGGTACCTCATGGGCTCCATGACCC

CACAGGCTGTGCTGGCTTTTGTGGCCCTGATCCCTCCAACCCTCCCTGGC

ACCAACATTGTTCTGGGAGCACTGCCTGAAGACAGACACATTGACAGGCT

GGCAAAGAGGCAGAGACCTGGAGAGAGACTGGACCTGGCCATGCTGGCTG

CAATCAGAAGGGTGTATGGACTGCTGGCAAACACTGTGAGATACCTCCAG

TGTGGAGGCTCTTGGAGAGAGGACTGGGGACAGCTCTCTGGAACAGCAGT

GCCCCCTCAAGGAGCTGAGCCCCAGTCCAATGCTGGTCCAAGACCCCACA

TTGGGGACACCCTGTTCACCCTGTTCAGAGCCCCTGAGCTGCTGGCTCCC

AATGGAGACCTGTACAATGTGTTTGCCTGGGCTCTGGATGTTCTAGCCAA

GAGGCTGAGGTCCATGCATGTGTTCATCCTGGACTATGACCAGTCCCCTG

CTGGATGCAGAGATGCTCTGCTGCAACTAACCTCTGGCATGGTGCAGACC

CATGTGACCACCCCTGGCAGCATCCCACCATCTGTGACCTAGCCAGAAC

CTTTGCCAGGGAGATGGGAGAGGCCAACTAA
```

Immune checkpoints are regulators of the immune system. Immune checkpoint molecules have been considered as targets for cancer immunotherapy due to their potential for use in multiple types of cancers. Examples of the immune checkpoint gene include, but are not limited to, the E3 ubiquitin ligase Cbl-b. CTLA-4. PD-1, TIM-3, killer inhibitory receptor (KIR), LAG-3, CD73, Fas, the aryl hydrocarbon receptor, Smad2, Smad4, TGF-beta receptor, ILT-3, IDO, KIR, and LAG3. In a certain embodiment, the immune checkpoint gene is PD-1. In some embodiments, the PD-1 sequence includes, but is not limited to, the following sequence.

```
PD-1 sequence
                                            (SEQ ID NO: 3)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCTTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCTGCTCCCGGGCCGCACGAGGGACAATA

GGAGCCAGGCGCACCGGCCAGCCCCTGAAGGAGGACCCCTCAGCCGTGCC

TGTGTTCTCTGTGGACTATGGGGAGCTGGATTTCCAGTGGCGAGAGAAGA
```

CCCCGGAGCCCCCCGTGCCCTGTGTCCCTGAGCAGACGGAGTATGCCACC

ATTGTCTTTCCTAGCGGAATGGGCACCTCATCCCCCGCCCGCAGGGGCTC

AGCCGACGGCCCTCGGAGTGCCCAGCCACTGAGGCCTGAGGATGGACACT

GCTCTTGGCCCCTC

Natural cytotoxicity triggering receptors also can be used in the vector of the present disclosure. Examples of the natural cytotoxicity triggering receptor include, but are not limited to, NCR1, NCR2 and NCR3. In a certain embodiment, the natural cytotoxicity triggering receptor is NCR3. In some embodiments, the NCR3 sequence includes, but is not limited to, the following sequence.

NCR3 sequence
(SEQ ID NO: 4)
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTGGTACAGTCCTCCTCCTTCGGGCTGGATTCTATGCTGTCAGC

TTTCTCTCTGTGGCCGTGGGCAGCACCGTCTATTACCAGGGCAAATGTCT

GACCTGGAAAGGTCCAAGAAGGCAGCTGCCGGCTGTGGTCCCAGCGCCCC

TCCCACCACCATGTGGGAGCTCAGCACATCTGCTTCCCCCAGTCCCAGGA

GGC

TNF-related apoptosis-inducing ligand (TRAIL) is a protein functioning as a ligand that induces the process of cell death. Examples of the TRAIL gene include, but are not limited to, TIC10. In some embodiments, the TIC10 sequence includes, but is not limited to, the following sequence.

TRAIL sequence
(SEQ ID NO: 5)
ATGGCTATGATGGAGGTCCAGGGGGGACCCAGCCTGGGACAGACCTGCGT

GCTGATCGTGATCTTCACAGTGCTCCTGCAGTCTCTCTGTGTGGCTGTAA

CTTACGTGTACTTTACCAACGAGCTGAAGCAGATGCAGGACAAGTACTCC

AAAAGTGGCATTGCTTGTTTCTTAAAAGAAGATGACAGTTATTGGGACCC

CAATGACGAAGAGAGTATGAACAGCCCCTGCTGGCAAGTCAAGTGGCAAC

TCCGTCAGCTCGTTAGAAAGATGATTTTGAGAACCTCTGAGGAAACCATT

TCTACAGTTCAAGAAAAGCAACAAAATATTTCTCCCCTAGTGAGAGAAAG

AGGTCCTCAGAGAGTAGCAGCTCACATAACTGGGACCAGAGGAAGAAGCA

ACACATTGTCTTCTCCAAACTCCAAGAATGAAAAGGCTCTGGGCCGCAAA

ATAAACTCCTGGGAATCATCAAGGAGTGGGCATTCATTCCTGAGCAACTT

GCACTTGAGGAATGGTGAACTGGTCATCCATGAAAAGGGTTTTACTACA

TCTATTCCCAAACATACTTTCGATTTCAGGAGGAAATAAAAGAAAACACA

AAGAACGACAAACAAATGGTCCAATATATTTACAAATACACAAGTTATCC

TGACCCTATATTGTTGATGAAAAGTGCTAGAAATAGTTGTTGGTCTAAAG

ATGCAGAATATGGACTCTATTCCATCTATCAAGGGGAATATTTGAGCTT

AAGGAAAATGACAGAATTTTTGTTTCTGTAACAAATGAGCACTTGATAGA

CATGGACCATGAAGCCAGTTTTTTCGGGGCCTTTTTAGTTGGC

The vector of the present disclosures comprises one or more control sequences to regulate the expression of the polynucleotide of the present disclosure. Manipulation of the isolated polynucleotide prior to its insertion into a vector may be desirable or necessary depending on the expression vector utilized. Techniques for modifying polynucleotides and nucleic acid sequences utilizing recombinant DNA methods are well known in the art. In some embodiments, the control sequences include, among others, promoters, leader sequences, polyadenylation sequences, propeptide sequences, signal peptide sequences, and transcription terminators. In some embodiments, suitable promoters are selected based on the host cells selection.

A recombinant expression vector comprising the polynucleotide of the present disclosure is disclosed along with one or more expression regulating regions such as a promoter and a terminator, a replication origin, etc., depending on the type of hosts into which they are to be introduced. Non-limiting examples of constitutive promoters include SFFV, CMV, PKG, MDNU3, SV40, Ef1a, UBC, and CAGG.

In some embodiments, the various nucleic acid and control sequences described herein are joined together to produce recombinant expression vectors which include one or more convenient restriction sites to allow for insertion or substitution of the polynucleotide of the present disclosure at such sites. Alternatively, in some embodiments, the polynucleotide of the present disclosure is expressed by inserting the polynucleotide or a nucleic acid construct comprising the sequence into an appropriate vector for expression. In some embodiments involving the creation of the expression vector, the coding sequence is located in the vector so that the coding sequence is operably linked with the appropriate control sequences for expression. The recombinant expression vector may be any suitable vector (e.g., a plasmid or virus) that can be conveniently subjected to recombinant DNA procedures and bring about the expression of the polynucleotide of the present disclosures. The choice of the vector typically depends on the compatibility of the vector with the host cell into which the vector is to be introduced. The vector may be a linear or closed circular plasmid. In one embodiment, the vector is a viral vector. Examples of viral vectors include retroviral vectors, lentiviral vectors, adenovirus vectors, adeno-associated virus vectors, alphavirus vectors and the like. In a certain embodiment, the viral vector is lentiviral vector. Lentiviral vectors are based on or derived from oncoretroviruses (the sub-group of retroviruses containing MLV), and lentiviruses (the sub-group of retroviruses containing HIV). Examples of such include, without limitation, human immunodeficiency virus (HIV), equine infectious anaemia virus (EIAV), simian immunodeficiency virus (SIV) and feline immunodeficiency virus (Hy). Alternatively, it is contemplated that other retroviruses can be used as a basis for a vector backbone such as murine leukemia virus (MLV).

In some embodiments, the vector used in the present disclosure is pLAS3w, pLAS3w.Ppuro, pLAS3w.Pneo, pLAS3w.Phyg and pLAS3w.Pbsd, pCMV-ΔR8.91 or pMD.G.

In another aspect, the present invention provides a kit or combination comprising the vector or engineered cell of the present disclosures and optionally an additional active agent. In one embodiment, the additional active agent is GCV.

The vector or engineered cell of the present disclosure is typically in combination with another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers). Exemplary protein excipients include serum albumin such as human serum albumin (HSA), recombinant human albumin (rHA), gelatin, casein, and the like. The carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Any of the compositions described herein may be comprised in a kit. In a non-limiting example, cells for cell therapy or one or more reagents to produce the cells may be comprised in a kit. The kits may also comprise a second container means for containing a sterile, pharmaceutically acceptable buffer and/or other diluent. Where there is more than one component in the kit, the kit also will generally contain a second, third or other additional container into which the additional component(s) may be separately placed. However, various combinations of components may be comprised in a vial. The kit may have a single container means, and/or it may have distinct container means for each compound. The kits of the present invention also will typically include a means for containing any container(s) in close confinement for commercial sale. Such containers may include injection or blow-molded plastic containers in which the desired vials are retained.

In a further aspect, the present invention provides a method for treating a cancer or enhancing intratumor immunity in a subject, comprising administering an effective amount of the engineered stem cell of the present disclosure to the subject. In one embodiment, the effective amount ranges from 100,000 ($1\times10^5$) ~2,000,000 ($2\times10^6$) cells. In some embodiment, the effective amount ranges from $1\times10^5$ to $1\times10^6$ cells.

In one embodiment, the cancer is a metastatic cancer.

In one embodiment, the method enhances immunity in the tumor microenvironment through an increase in tumor-specific CD8$^+$IFN-γ$^+$CD44$^+$ T cells with central memory potential. In one embodiment, the method induces a significant reduction in Tregs, and thereby reverses the ratio of CD8$^+$ and CD4$^+$ T cells to Tregs within the tumors. The method also decreases the number of TAMs, which increases the ratio of CD8$^+$ and CD4$^+$ T cells to TAMs in the TME. In one embodiment, the effective amount ranges from 100,000 ($1\times10^5$) ~2,000,000 ($2\times10^6$) cells. In some embodiment, the effective amount ranges from $1\times10^5$ to $1\times10^6$ cells.

Exemplary cancers treated using methods and compositions as described herein are breast cancer, colon cancer, rectal cancer, lung cancer, ovarian cancer, prostate cancer, skin cancer, brain cancer, bladder cancer, endometrial cancer, kidney cancer, pancreatic cancer, thyroid cancer, or melanoma or metastatic cancers thereof. Exemplary cancer cells include, but are not limited to, carcinoma, melanoma, leukemia, fibrosarcoma, sarcoma, adenocarcinoma, and glioma.

Methods of delivery include but are not limited to intra-arterial, intra-muscular, and intravenous. In a specific embodiment, it may be desirable to administer the pharmaceutical compositions and/or cells of the disclosure locally to the area in need of treatment; this may be achieved by, for example, and not by way of limitation, local infusion during surgery, by injection or by means of a catheter. In some embodiments, the compositions or cells are administered by intravenous injection. In a further embodiment, the compositions or cells are administered by intramuscular injection. The compositions may be administered in one injection or in multiple injections. Solutions containing the cells can be prepared in suitable diluents such as water, ethanol, glycerol, liquid polyethylene glycol(s), various oils, and/or mixtures thereof, and others known to those skilled in the art. In some embodiments, the engineered stem cell of the present disclosure can be intravenously or intra-arterially administered to the subject. The present disclosure unexpectedly found that the above administrations of the engineered stem cell of the present disclosure have advantageous efficacy in treating a cancer, enhancing intratumor immunity or enhancing immunity in the tumor microenvironment. Particularly, the intra-arterial administration exhibits better efficacy than the intravenous administration.

In one embodiment, the engineered stem cell of the present disclosure can be administered with an additional active agent. In some embodiments, the engineered stem cell and the additional active agent can be administered concurrently, separately or simultaneously. In one embodiment, the engineered stem cell and the additional active agent can be administrated periodically. In a further embodiment, the additional active agent is GCV.

It is to be understood that if any prior art publication is referred to herein, such reference does not constitute an admission that the publication forms a part of the common general knowledge in the art.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

EXAMPLES

Methods and Materials:
Preparation, Isolation and Characterization of UMSCs and Other Stem Cells Collected human umbilical cord tissues approved by the Institutional Review Board (IRB) of the China Medical University Hospital, Taichung were washed three times with Ca$^{2+}$ and Mg$^{2+}$-free PBS (DPBS, Life Technology). They were mechanically cut by scissors in a midline direction and the vessels of the umbilical artery, vein and outlining membrane were dissociated from the Wharton's jelly (WJ). The jelly content was then extensively cut into pieces smaller than 0.5 cm$^3$, treated with collagenase type 1 (Sigma, St Louis, USA) and incubated for 3 h at 37° C. in a 95% air/5% $CO_2$ humidified atmosphere. The explants then were cultured in DMEM containing 10% fetal calf serum (FCS) and antibiotics at 37° C. in a 95% air/5% $CO_2$ humidified atmosphere. They were left undisturbed for 5-7 days to allow for migration of the cells from the explants. The cellular morphology of umbilical cord-derived mesenchymal stem cells (UMSCs) became homogenously spindle shaped in cultures after 4-8 passages, and the specific surface molecules of cells from the WJ were characterized by flow cytometric analysis. The cells were detached with 2 mM EDTA in PBS, washed with PBS containing 2% BSA and 0.1% sodium azide (Sigma, USA) and incubated with the respective antibody conjugated with fluorescein isothiocyanate (FITC) or phycoerythrin (PE) including CD13, CD29, CD44, CD73, CD90, CD105, CD166, CD49b, CD1q, CD3, CD10, CD14, CD31, CD34, CD45, CD49d, CD56, CD117, HLA-ABC, and HLA-DR (BD, PharMingen). Thereafter, the cells were analyzed using a Becton Dickinson flow cytometer (Becton Dickinson, San Jose, Calif.).

Other types of stem cells can be obtained and cultured according to procedures known in the art.

Plasmid Construction:

TK, NCR3, TRAIL, PD-1 and GFP cDNA from plasmids of TK (0.1 μg) (pUNO1-HSV1tk, InvivoGen), NCR3 (0.1 μg) (pLenti-C-mGFP-NCR3, Origene), TRAIL (0.1 μg) (pCMV6-myc-DDK-TRAIL, Origene), or PDCD-1 (0.1 μg) (pLenti-C-Myc-DDK-PDCD1, Origene) were transferred into pIRES (Clontech) or pSF-CMV-CMV-Sbf1 (Oxford Genetics) by specific restriction enzyme linker (EcoR1 and Nhe1 in TK, BamH1 and Not1 in PD-1) to build as the construct of pIRES-TK-PD-1, pIRES-TK-GFP, pIRES-PD-1-GFP, etc. which was transfected into UMSCs by XtremeGene HP DNA (Roche) per manufacturer's instruction to engineer as the UMSC-TK-PD-1, UMSC-TK-GFP, and UMSC-PD-1-GFP. The above constructs can be transfected into other types of stem cells.

Lenti-Viral Plasmids:

Lentivector (pLAS3w), and packaging (psPAX2)/envelope plasmids (pMD2.G) were obtained from Academia Sinica, Taiwan. The cDNA encoding full-length human TK, NCR3, TRAIL, PD-1 and control GFP was recombinant from the cDNA (pUNO1-HSV1tk, InvivoGen; pLenti-C-mGFP-NCR3, Origene; pCMV6-myc-DDK-TRAIL, Origene pLenti-C-Myc-DDK-PDCD1, Origene) was transferred into pUltra (Addgene) and pSF-CMV-CMV-Sbf1 (Oxford Genetics) by specific restriction enzyme linker (EcoR1 and Nhe1 in TK, BamH1 and Not1 in PD-1) to build as the construct of pUltra-TRAIL-TK-PD-1, pUltra-TK-PD-1, pUltra-TK-GFP, pUltra-PD-1-GFP and pUltra-TRAIL-GFP. Subsequently, these templates were amplified by PCR using specific primers, and digested with restriction enzymes sub-cloned to lentiviral vector backbone plasmid pLAS2w and pLAS3w (Academia Sinica, Taiwan) (Lenti-TK-GFP, Lenti-PD-1-GFP, Lenti-TRAIL-GFP, Lenti-TK-PD-1-GFP, Lenti-TRAIL-PD-1-GFP and Lenti-TRAIL-TK-PD-1-GFP). To produce the recombinant lentivirus carrying TK, PD-1, TRAIL and control GFP, the recombinant plasmid and vector were co-transfected with packaging and enveloping plasmids into 293T cells at a ratio of 3:3:1 by XtremeGene HP DNA (Roche) transfection. The culture supernatant containing the virus particles was collected after 36 hours and again after another 24 hours at half the volume, and was then centrifuged at 15,000 rpm/min for 10 min to remove debris, and then transferred into a 36-mL ultracentrifuge tube for ultra-centrifugation at 25,000 rpm/min for 3 h. The pellet containing lentivirus was resuspended. Viruses were thawed immediately before titer and cell transduction. UMSCs were infected with the appropriate lentivirus where gene transfer efficiency reached at least 80%.

Lenti-Virus Transduction

Lenti-viral plasmid transductions were done in six-well plates. Unless otherwise specified, UMSCs were seeded at $1 \times 10^5$ cells per well in triplicate at a final volume of 1 ml per well with a multiplicity of infection (MOI) of 5. Protamine sulfate (Sigma-Aldrich) from an 8 mg/ml stock solution (in DMEM-LG, sterile filtered) was added to obtain the desired final concentration. Cells were transduced for 24 hours before being replaced with 1.5 ml per well to build as UMSC-TRAIL-TK-PD-1, UMSC-TK-PD-1, UMSC-TRAIL-PD-1, UMSC-TRAIL, UMSC-TK, and UMSC-PD-1. Overgrown cells were inoculated onto a six-well plate for drug screening using 1.0 mg/ml G418 or puromycin solutions (Sigma). The medium was replaced every 2 days. The expression of green fluorescent protein (GFP) was observed using inverted fluorescence microscopy based on the color of the medium and the cell state. Following 7 days of screening, the complete medium without G418 was replaced and cultivation was continued.

Construction of the piggyBac Transposon System for Stable Cell Lines

PiggyBac vector pPB-CMV-MCS-EF1α-RedPuro, which contains the multiple cloning sites (MCS), piggyBac terminal repeats (PB-TRs), core insulators (CIs) and puromycin selection maker (BSD) fused with RFP driven by the human EF1α, was used as the base vector (System Bioscience). A DNA fragment containing TRAIL-TK-PD-1, TK-PD-1, TRAIL-PD-1, TRAIL, TK, and PD-1 (from pUltra-TRAIL-TK-PD-1, pUltra-TK-PD-1, pUltra-TRAIL-PD-1, pUltra-TRAIL, pUltra-TK, and pUltra-PD-1) was PCR amplified and subcloned into the pPB-CMV-MCS-EF1α-RedPuro vector, in front of the coding region of EF1α. Detailed information regarding vector constructions is available upon request. To generate UMSC stable cells, the above plasmids were co-transfected with a piggyBac transposase expression vector (System Biosciences) into UMSC cells by an electroporation method using Amaxa Nucleofector II (Lonza). Stably cells (UMSC-TRAIL-TK-PD-1, UMSC-TK-PD-1, UMSC-TRAIL-PD-1, UMSC-TRAIL, UMSC-TK, and UMSC-PD-1) were selected in the presence of puromycin.

In Vitro Proliferation, Migration and Differentiation Assays

For examining cellular proliferation and migration, bromodeoxyuridine (BrdU) incorporation and transwell migration assays were performed for comparison of UMSC-TRAIL-TK-PD-1 or UMSCs. Proliferation of UMSC-TRAIL-TK-PD-1 or UMSCs was tested by measuring BrdU incorporation (10 μM) using a BrdU chemiluminescence immunoassay kit (Roche) and further confirmed by counting Trypan blue cells. After a 4-6 h starvation (incubation in medium lacking serum), UMSCs were incubated in medium for 2 days and pulse loaded with 10 μM BrdU for 12 h as previously described (J Clin Invest 2009; 119:1997). UMSCs were then incubated with anti-BrdU-peroxidase for 90 min and staining was developed by incubating with substrate solution for 3 min. Plates were read with an Lmax microplate luminometer (Molecular Devices). Results were analyzed and presented as percent (%) increase over control.

Cell migration assay was assessed as described previously with modifications (EMBO Mol Med 2013; 5:1227-1246). In brief, UMSC-TK-PD-1 or UMSCs were placed in 100 μL in the upper chamber (transwell: 6.5-mm diameter, 5.0-mm pore size) according to manufacturer's instructions (Costar, #3421). We used SDF-1α (100 ng/mL, R&D System, positive control) in the lower chambers. The assays were conducted over a 4-h incubation period at 37° C. in a 5% $CO_2$ incubator. Because almost all cells stay at the lower side of the membrane after migration, quantification can be performed by simply counting these cells. Adhered cells at the lower side of the membranes were counted under the microscopy as previously described.

Adipogenic differentiation was induced according to the method described previously (J Orthop Res 2002; 20:1060). In brief, confluent monolayer cultures of UMSC-TK-PD-1 or UMSCs were grown in adipogenic differentiation medium, consisting of DMEM-high glucose (DMEM-HG, Sigma), 100 U/mL penicillin, 100 mg/mL streptomycin, 100 mM insulin (Sigma), 500 mM 3-isobutyl-1-methylxanthine (Sigma), 1 mM dexamethasone (Sigma), 100 mM indomethacin (Sigma) and 10% FCS. Cells maintained in ordinary UMSCs medium served as a negative control. The adipogenic differentiation was changed three times per week. To assess adipogenic differentiation, cells were stained with 0.3% oil red O (Sigma) for 10 min at room temperature, (to label intracellular lipid accumulation), and counterstained with haematoxylin.

To induce osteogenic differentiation, confluent monolayer UMSC-TK-PD-1 or UMSCs cultures were grown in DMEM-high glucose (DMEM-HG, Sigma) containing 100 U/mL penicillin (Sigma), 100 mg/mL streptomycin (Sigma), 50 mg/mL L-ascorbic acid 2-phosphate (Sigma), 10 mM b-glycerophosphate (Sigma), 100 nM dexamethasone (Sigma) and 10% FCS. Cells maintained in ordinary UMSC medium served as negative controls. The osteogenic differentiation medium was changed three times per week. Levels of osteogenesis were determined using Alizarin red S staining (1%, Sigma) to detect calcium mineralization (J Biomed Mater Res 1998, 42, 433).

Chondrogenic differentiation of UMSC-TK-PD-1 or UMSCs was induced using a high-density pellet cell culture system (J Biomed Mater Res 1998, 42, 433). Cells were washed in serum-free chondrogenic differentiation medium consisting of DMEM-HG, 100 U/mL penicillin, 100 mg/mL streptomycin, 50 mg/mL L-ascorbic acid 2-phosphate, 40 mg/mL proline (Sigma), 100 mg/mL sodium pyruvate (Sigma), 100 nM dexamethasone, and ITS-plus (10 mg/ml bovine insulin, 5.5 mg/ml transferrin, 5 mg/ml sodium selenite, 4.7 mg/ml linoleic acid, and 0.5 mg/ml bovine serum albumin, Sigma). Aliquots of 250,000 cells were resuspended in chondrogenic differentiation medium and centrifuged at 250×g, and then 10 ng/mL TGF-β1 (R&D Systems) was added. Pellets maintained in chondrogenic differentiation medium without TGF-β1 served as negative controls. Medium was changed twice per week. Chondrogenic differentiation of pellet cultures was confirmed histologically using Alcian blue staining (Sigma) of sulfated proteoglycans. In addition, endothelial cells were induced to differentiate to vascular tubes formation by culturing UMSC-TK-PD-1 or UMSCs for 2-3 days in EBM (Cambrex) on 24-well plates precoated with Matrigel (300 μL/well; Becton Dickinson) and vascular endothelial growth factor (VEGF, 10 ng/ml, Sigma) as described previously (Nat Rev Cancer 2002, 2, 826).

To induce neural cell differentiation, UMSC-TK-PD-1 or UMSCs were incubated with DMEM using a three-step method with modification (Stem Cells Transl Med. 2015; 4:775-88). Briefly, in the neural induction step, cells were plated at low density on 6-well plates containing fibronectin (Sigma), and then exposed sequentially to (1) DMEM-HG (Sigma), containing 10% FCS, and 10 ng/mL bFGF (R&D System) for 24 h, (2) in the neural commitment step, DMEM-HG containing, 1 mM β-mercaptoethanol (βME, Sigma), and 10 ng/mL NT-3 (R&D Systems) for 2 days, and (3) in the neural differentiation step, DMEM-HG containing NT-3 (10 ng/mL, R&D Systems), NGF (10 ng/mL, R&D Systems) and BDNF (50 ng/mL, R&D Systems) for 3 to 7 days. Following cell differentiation, the cells were left for immunohistochemical analysis.

Flow-Cytometry

For the analysis of the cell surface-marker expression, cells were detached with 2 mM EDTA in PBS, washed with PBS containing BSA (2%) and sodium azide (0.1%), and then incubated with the respective antibody conjugated with fluorescein isothiocyanate (FITC) or phycoerythrin (PE) until analysis. The gating was performed based on the justification of first gate, exclusion of doublets by FSC-A and FSC-H, exclusion of dead cells by selection of 7-AAD$^+$ (R&D systems)/CD45$^+$ or FSC-A according to the previous literature (Mucosal Immunol 2013, 6(3): 498-510). As a control, cells were stained with mouse IgG1 isotype-control antibodies. The antibodies to PD-1, PD-L1, CD3, CD8, CD4, CD25, Foxp3, CD44, CD45, CD11b, F4/80, IFN-γ, CD206, TRAIL and GFP for flow cytometry were purchased from BD Biosciences. Cells were analyzed using a FACScan (BD) with CellQuest Analysis (BD Biosciences) and FlowJo software v.8.8 (TreeStar Inc.). Results are expressed by the percentage of positively stained cells relative to total cell number. For quantitative comparison of surface protein expression, the fluorescence intensity of each sample is presented as median fluorescence intensity (MFI). For intracellular staining of Ki-67 and granzyme B, TILs were cultured in the presence of 1 μg/ml of anti-CD3 for 48 h. Cells were then incubated with anti-CD8 before permeabilization with Triton x100 and then stained with antibody against Ki-67 (Millipore) and Granzyme B. Data were analyzed using a FACScan (BD) with CellQuest Analysis (BD Biosciences) and FlowJo v.8.8 (TreeStar).

In Vitro Analysis of Antigen-Specific T-Cell Responses

Splenocytes ($2 \times 10^6$) from BALB/c mice were cultured on 24-well plates in RPMI-1640 media (Gibco) supplemented with 10% FBS (Sigma), 1% penicillin/streptomycin (Gibco). Then, splenocytes cocultured with UMSC-TRAIL-TK-PD-1 ($2 \times 10^5$) were either left unstimulated or incubated with CD3-CD28 beads (Dynabeads, Thermo). For proliferation assays, splenocytes were stained with Carboxyfluorescein succinimidyl ester (CFSE) (Invitrogen) as previously described (Nat Protoc 2007; 2:2049-56). We estimated the proliferation/division of cells using the Proliferation Index (PI), which can be calculated by the formula: PI=total number posterior to proliferation/total number prior to proliferation. After a 6-day-culture cells were harvested and stained to analyze proliferation of Treg, CD4- and CD8-T cell subsets. Alternatively, to analyze proliferation after a 6-day culture in longitudinal samples for which cell numbers were limited, non-CF SE stained splenocytes were cultured as previously described, and stained with Ki67 or isotype control antibodies. Fold change in proliferation (FC proliferation) was calculated as a ratio of proliferation under UMSC-TRAIL-TK-PD-1 condition divided by proliferation under control condition.

Moreover, mixed lymphocyte response (MLR) assays were performed by co-culturing $1 \times 10^5$ cells responder CD4$^+$ T cells from mice spleen enriched by nylon wood column (Polysciences) with allogeneic dendritic cells (DC) at a ratio of 10:1 (T:DC) in flat-bottom 96-well microtiter plates. CD4$^+$ T cells and allogeneic DC were incubated for 6 days in the absence or presence of UMSC-TK-PD-1 ($10^2$, $10^3$ and $10^4$). The effector T cells were serially stimulated a total of three times. Culture supernatants were harvested on day 5 for ELISA analysis of IFN-γ and IL-12 secretion (R&D).

Suicide Effect in UMSC-TK-PD-1 with Ganciclovir (GCV) in Vitro

To investigate the biological effect in vitro, the suicide ability of UMSC-TK-PD-1 combined with GCV was analyzed. After incubation at 37° C. in 5% $CO_2$ for 24 h, various dosages of GCV (0.1, 1, 10 and 100 μg/mL) were added in each well every day for 7 consecutive days. Cell viability was evaluated by MTT assay (Invitrogen) and GFP fluorescent intensity by luminometer (Promega).

In Vitro Bystander Effect Assay

4T1-Luc (BCRC, Taiwan), CT26-Luc (BCRC, Taiwan) or Hep-55.1C-Luc (BCRC, Taiwan) cells ($1\times10^4$ cells) and various numbers of UMSC-TRAIL-TK-PD-1 cells (UMSC-TRAIL-TK-PD-1: tumor cells ratios=1:1, 1:4, 1:16, 1:32, and 1:64) co-incubated at 37° C. in 5% $CO_2$ in DMEM with 10% FBS were seeded on a 24 well-plate. The medium was replaced every day with fresh medium containing 100 μg/mL GCV for 7 consecutive days. UMSC-TRAIL-TK-PD-1 and 4T1-Luc cells were also seeded in DMEM medium with 10% FBS without GCV as the corresponding control group. After 8 days, luciferase fluorescent intensity by luminometer (Promega) was acquired from 5 random fields to determine cell density. Further investigation on the time course of bystander effect of the above co-culture system was performed in the same number of UMSC-TRAIL-TK-PD-1 and 4T1-Luc cells seeded in the 12-well culture plates with GCV (100 μg/mL) daily. Cell mortality ratio was measured as percentage of the fluorescence intensity of GFP and luciferase through a luminometer (Promega).

In Vitro Apoptosis Assay

To investigate the pro-apoptogen potential toward various tumor cells, we carried out cocultures at 1:2 ratio and evaluated the cytotoxicity at 24 h by Annexin-V-FITC/propidium iodide (PI) staining (eBioscience) using the FACScanto II. The tumor cell population was gated based on forward scatter (FSC) and side scatter (SSC) parameters.

Mice Model and Tumor Inoculation

All animal experiments were carried out in accordance with Institutional Guidelines on Animal Research of China Medical University. Six to eight week-old female BALB/c (National Animal Center of Taiwan) mice were utilized for building the mouse cancer model using 4T1, CT26, Hep-55.1C, CT26-Luc, 4T1-Luc or Hep-55.1C-Luc. In brief, 4T1 cells ($1\times10^6$) were implanted in the $4^{th}$ mouse mammary fat pad of female BALB/c mice at the right side of the abdomen, and the treatments were started on day 8 after tumor implantation.

In Vivo UMSCs Migration Assay

To examine the biodistribution of intravenously or intra-arterially injected stem cells, luciferase gene (pHAGE PGK-GFP-IRES-LUC-W, Addgene) was subcloned into pUltra-TRAIL-TK-PD-1 and then pLAS3w to construct Lenti-TRAIL-TK-PD-1-Luc. UMSCs engineered by Lenti-TRAIL-TK-PD-1-Luc (UMSC-TRAIL-TK-PD-1-Luc) ($2\times10^6$ cells) were injected days into the femoral vein or femoral artery of 4T1 tumor-bearing mice at 7 days after tumor inoculation. Ex vivo imaging was performed by placing whole animal in the IVIS Lumina Imaging System (Xenogen) at indicated time points after UMSC-TRAIL-TK-PD-1-Luc injection (6 h, 1 d, 3 d, 6 d, 9 d and 14 d) and analyzing fluorescence based on the manufacturer's recommendations. Fluorescence intensity was quantified as photons/sec/$cm^2$ by Living Image software (Xenogen). Mice were sacrificed at 24 hours after UMSC injection, and then various organs (lung, liver, spleen, heart, kidney, and brain) were isolated. Each organ was minced, treated with collagenase, and prepared for flow-cytometric analysis.

Bioluminescent Imaging (BLI)

Animals were imaged with the IVIS Imaging System 200 Series (Xenogen) to record bioluminescent signal emitted from the 4T1-Luc, CT26-Luc, Hep-55.1C-Luc (luciferase expression). Animals were anesthetized with isoflurane and received intra-peritoneal injection of D-luciferin (Caliper) at a dose of 270 mg/g body weight. Imaging acquisition was performed at 15 min after intraperitoneal injection of luciferin. For BLI analysis, regions of interest encompassing the intracranial area of signal were defined using an IVIS System (Xenogen), and the total photon flux was recorded. To facilitate comparison of cellular engrafted rates, each animal's luminescence scores were normalized against its own luminescence reading at Day 14, thereby allowing each mouse to serve as its own control.

In Vivo Therapeutic Effect of UMSC-TRAIL-TK-PD-1 on Tumor-Bearing Mice

In 4T1-Luc and Hep55.1C-Luc mice model, we first examined whether the intravenous injection of UMSC-TRAIL-TK-PD-1 could significantly induce the tumoricidal effect compared to the anti-PD-1 (Roche) or IgG-control. Then, the treatment groups were subdivided into six groups (FIG. 6A): IgG-control group; UMSC-PD-1 (UP) group; UMSC-TRAIL (UT) group; UMSC-TRAIL-PD-1 (UTP) group; UMSC-TRAIL-TK+GCV (UTTG) group; and UMSC-TK-PD-1+GCV (UTPG) group. Before each treatment, cells were subjected to hypoxia preconditioning protocol with incubation in 3% $O_2$ level for 24 hours to induce CXCR4 (Millipore) upregulation to enhance the tumor homing effect (Cancer Research 2012; 73:2333-2344). Antitumor effects of sequential therapy were evaluated by repeating second and third injections of $5\times10^5$ cells in each group at 10-day interval. GCV (50 mg/kg) was administered intraperitoneally for 7 consecutive days starting on day 2 after each treatment administration.

Next, to further demonstrate whether the intra-arterial injection of UMSC-TRAIL-TK-PD-1 through femoral artery could significantly induce the tumoricidal effect compared to the UMSC-TK-PD-1, the treatment groups were again subdivided into six groups (FIG. 6F): IgG-control group; UMSC-TK-PD-1+GCV (UTPG) group; UMSC-TRAIL-TK-PD-1 (UTTP) group; and UMSC-TRAIL-TK-PD-1+GCV (UTTPG) group.

Survival Study

To determine the therapeutic effect of UMSC-TRAIL-TK-PD-1 on the survival of 4T1-Luc and Hep55.1C-Luc tumor-bearing mice in vivo, the mice were treated with six different therapeutic targets via the right femoral vein every 4 days three consecutive times (q4dx3) within 10 days after tumor inoculation (n=8). The tumor volumes were monitored using a digital caliper (Mitutoyo) every 2-3 d using the following equation:

$$\text{Tumor volume (min}^2) = \frac{W^2 \times L}{2}, \quad \text{(Equation 1)}$$

where W is the width of the tumor and L is the length of the tumor (W<L). Animals were euthanized when the volume was over 3,000 $mm^3$ for ethical reasons. Mice were sacrificed when tumor size reached 2 cm at the largest diameter, or when their body weight decreased to less than 80%. The survival rate using Kaplan-Meier survival analysis was reported as the median and mean survival times with a 95% confidence interval. The statistical difference between these different conditions was determined by log-rank analysis (n=8).

Isolation of infiltrating leukocytes (TILs), splenic cells and peripheral blood mononuclear cells (PBMCs)

Four weeks after the final treatment, leukocytes in the tumors, spleens or peripheral blood were harvested from the freshly euthanized mice. Tumor-infiltrating lymphocytes (TILs) were prepared for single cell suspensions using the method previously described (Blood 2005; 06:2339). In brief, TILs were isolated by digesting tumor tissue with collagenase type IV (2.5 mg ml$^{-1}$, Gibco) for 20 min and concentrated by centrifugation in a discontinuous percoll gradient (GE Healthcare). The CD8$^+$ T cells in TIL suspensions were separated by mixing with αCD8 microbeads (Miltenyi Biotec) on a MACS column or staining with anti-CD8 antibody on a FACSAria (BD Biosciences) sorter (purity>95%). The total number of infiltrating CD8$^+$ T cells/gram of tumor was obtained by multiplying the percentage of CD8$^+$ T cells by the total number of lymphocytes obtained from percoll gradient and dividing that number by 100 and by the weight of the tumors. Tumor associated macrophage (TAM, CD11b$^+$CD206$^+$F4/80$^+$ cells) in TIL suspension was examined on a FACSAria (BD Biosciences) after staining with anti-CD11b, anti-CD206, or anti-F4/80 antibodies (purity>95%). Regulatory T lymphocytes (Treg, CD4+CD25+) were purified using an isolation kit (Miltenyi Biotec) (purity>90%). Regulatory T lymphocytes (CD4$^+$CD25$^+$Foxp3$^+$ cells) were assayed on a FACSAria (BD Biosciences) after staining with anti-CD4, anti-CD25 and anti-Foxp3 antibodies (purity>95%). We teased the spleens apart and filtered them with nylon mesh screen to obtain single cell suspensions. To further produce single cell splenocyte suspensions, we removed red blood cells by using RBC lysis buffer. The splenic CD8$^+$ T cells were separated by mixing the cells with αCD8 microbeads (Miltenyi Biotec) on a MACS column or staining with anti-CD8 antibody on a FACSAria (BD Biosciences) sorter (purity>95%).

Peripheral blood mononuclear cells (PBMCs) were isolated from each mouse (Blood. 2001; 98: 3520-6). The cells were collected using the Ficoll-Histopaque (Sigma Aldrich) centrifugation method (Science. 1997; 275: 964-7), and washed twice with 1 mM EDTA in PBS for further experimentation.

Flow Cytometry

TILs suspension were washed with PBS containing BSA (2%) and sodium azide (0.1%). Cell were stained with the respective fluorochrome-conjugated monoclonal antibodies to the cell surface markers as follows: anti-PD-L1 (MIH5), anti-CD3 (145-2C11), anti-CD8 (53-6.7), anti-CD11b (M1/70), anti-CD45 (30-F11), anti-IFN-γ (XMG1.2), anti-CD44 (IM7.8.1R), anti-CD4 (GK1.5), anti-CD25 (PC61.5), anti-Foxp3 (MF23), anti-F4/80 (BM8) and anti-CD206 (MR5D3). As a control, cells were stained with mouse IgG1 isotype-control or IgG2 isotype-control antibodies. Cells were analyzed using a FACScan (BD) with CellQuest Analysis (BD Biosciences) and FlowJo software v.8.8 (TreeStar Inc.).

The gating was performed based on the right justification of first gate, exclusion of doublets by FSC-A and FSC-H, exclusion of dead cells and further selected as being 7AAD$^+$/CD45$^+$ (or FSC-A) according to previous literature (*Mucosal Immunol.* 2013; 6:498-510). Then, CD8$^+$ T cells, CD4$^+$ T cells, Treg and TAM from TIL or splenocyte suspensions were analyzed using a FACScan (BD) with the CellQuest Analysis (BD Biosciences) and FlowJo software v.8.8 (TreeStar Inc.). Results were expressed by the percentage of positively stained cells relative to total cell number. Differences between groups were evaluated by two-way ANOVA with Newman-Keuls post hoc test. A P value<0.05 was considered significant.

Isolation of CD8$^+$CD44$^+$IFN-γ$^+$ T Cells from TILs

The CD8$^+$ T cells in TILs suspension were separated by mixing with αCD8 microbeads (Miltenyi Biotec) on a MACS column. To examine the expression of IFN-γ and CD44, the separated CD8$^+$ T cells were treated using anti-mouse CD28 mAb (0.5 μg), Monensin, and brefeldin A for 3 hours. In the meantime, they were co-cultured with 1×10$^6$ irradiated 4T1-Luc cells (at a rate of 84 cGy min$^{-1}$ with a 0.5-mm Cu filter, Philips x-ray unit) at 37° C. for 24 h. Flow cytometric analysis of IFN-γ and CD44 expression was then performed using BD Cytofix/Cytoperm Plus Kit following the manufacturer's instructions.

Evaluation of Ki-67 and Granzyme B Expression in CD8$^+$ T Cells

For intracellular staining of Ki-67 and granzyme B, TILs were cultured in the presence of anti-CD3 (1 μg ml$^{-1}$ for 48 h. The cells were then incubated with anti-CD8 before permeabilization with Tritonx100, and stained with antibody against Ki-67 and Granzyme B (Millipore).

CFSE Test

Tregs isolated from tumor were co-cultured with carboxyfluorescein diacetate succinimidyl ester (CFSE)-treated spleen CD8$^+$ T cells in the presence of CD3 antibodies, and the proliferation of CD8$^-$ T cells was monitored using the fluorescent intensity of CF SE. The CFSE$^{low}$ cells are defined as the cells with lower fluorescent intensity than the original population, which represented the proliferated CD8$^+$ T cells.

Cytokine Measurement

TILs from mice treated with different protocols were cultured directly at a density of 2×10$^5$ cells/mL in 6-well plates in PRMI-1640 (Invitrogen) medium with 2 mM L-glutamine (Sigma-Aldrich) for 48 h. The level of TNF-α, VEGF, IL-10 and TGF-β was measured with Quantikine ELISA kit (R&D Systems). Semi-quantitative analysis of TNF-α, VEGF, IL-10 and TGF-β levels in culture supernatants and serum was performed. Optical density was measured using a spectrophotometer (Molecular Devices) and standard curves were generated with the program SOFTmax (Molecular Devices).

Evaluation of Anti-Metastasis Ability

The mice was tumor-challenged mice by 4T1-Luc, CT26-Luc or Hep-55.1C-Luc were examined for lung metastasis by direct visual counting of the metastatic nodules. Lungs were then excised and washed once in water and fixed further by immersion in 4% PFA, and dehydrated in 30% sucrose at room temperature. Surface metastases subsequently appeared as white nodules and were counted under a microscope.

Immunohistochemical Assessment

Animals were anesthetized with chloral hydrate (0.4 g/kg, ip) and their abdominal skin tissues were fixed by transcardial perfusion with saline followed by immersion in 4% paraformaldehyde. Tissue samples were dehydrated in 30% sucrose, frozen on dry ice, and then cut in a series of adjacent 6-μm-thick coronal sections using a cryostat. Sections were stained with H&E and Prussian blue (for identifying the iron) for observation by light microscopy (Nikon, E600). Each section was immunostained with antibodies against CD4 (1:100; BD), CD8 (1:400; BD), using secondary antibodies conjugated with FITC or Cy-3 (1:500; Jackson Immunoresearch) and then analyzed in three-dimensional images using a Carl Zeiss LSM510 laser-scanning confocal microscope. The total number of cells co-stained with a cell type-specific marker was measured as previously described (*J. Cereb. Blood Flow Metab.* 2008; 28, 1804-1810).

TUNEL Assay

Cellular apoptosis was assayed by immuno-histochemistry using a commercial TUNEL staining kit (DeadEnd Fluorimetric TUNEL system; Promega) as previously described (*Proceedings of the National Academy of Sciences* 2009; 106, 9391-9396. The percentage of TUNEL labeling was expressed as the number of TUNEL-positive nuclei divided by the total number of nuclei stained with DAPI (*Nat. Protocols* 2016; 11:688-713; *PLoS Genet.* 2009; 5:e1000379). The apoptotic index expressed as the percentage of TUNEL-positive apoptotic nuclei divided by the total number of nuclei visualized by counterstaining with DAPI obtained from counts of randomly chosen microscopic fields.

Assessment of Immune-Related Adverse Events (irAEs)

We evaluated irAEs including: (1) weight monitoring, (2) histology, (3) immune cell infiltration, and (4) liver and kidney function after the treatment of each group. The body weight of the mice was monitored during the treatment. In addition, H&E staining of livers, lungs, spleens, kidneys, and colons sections of the mice treated with each group were evaluated at 4 weeks after tumor inoculation (n=6) for histology analysis. The $CD8^+$ and $CD4^+$ T cell infiltration (Cancer Res 2016; 76:5288-5301) to liver, colon, kidney, and lung were examined by IHC and scored by counting the number of positive cells in ten high power field per $mm^2$. Furthermore, biochemical profiles of the ALT, AST, creatinine and glucose were measured using mouse serum from sequential time points (0, 5 10, 15, 20, 25 and 30 d) of each group (n=6) by a Beckman Unicell DxC800 analyzer.

Statistical Analysis

All measurements in this study were performed in a blinded design. Results were expressed as mean±SEM. Two-tailed Student's t tests was used to evaluate significance of mean differences between the control and the treated group. Differences between groups were evaluated by two-way ANOVA with the Newman-Keuls post hoc test. A P value<0.05 was considered significant.

Example 1

In Vitro Characterization of UMSCs and UMSC-TK-PD-1

Figure 1B:
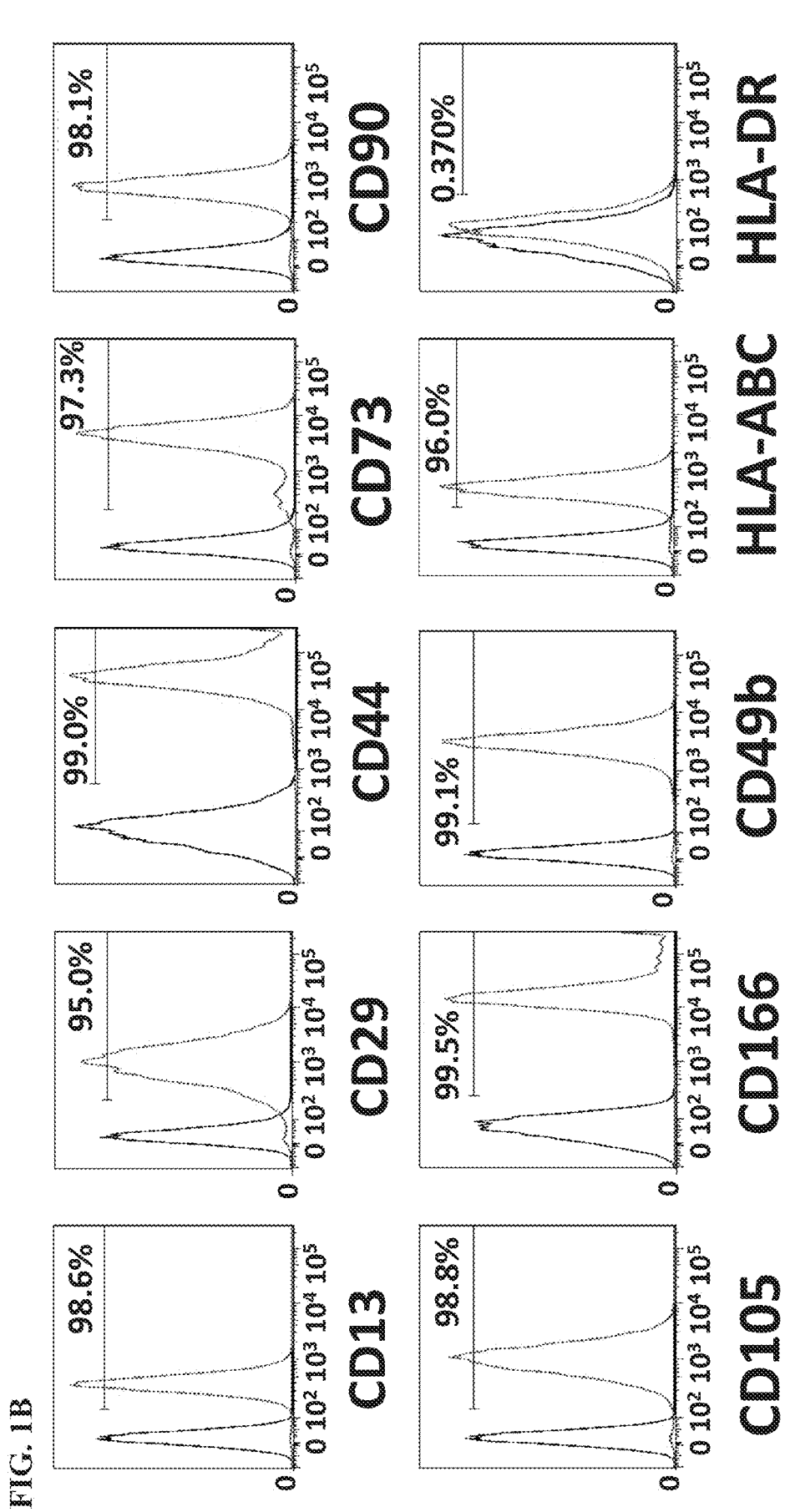
Figure 1B:
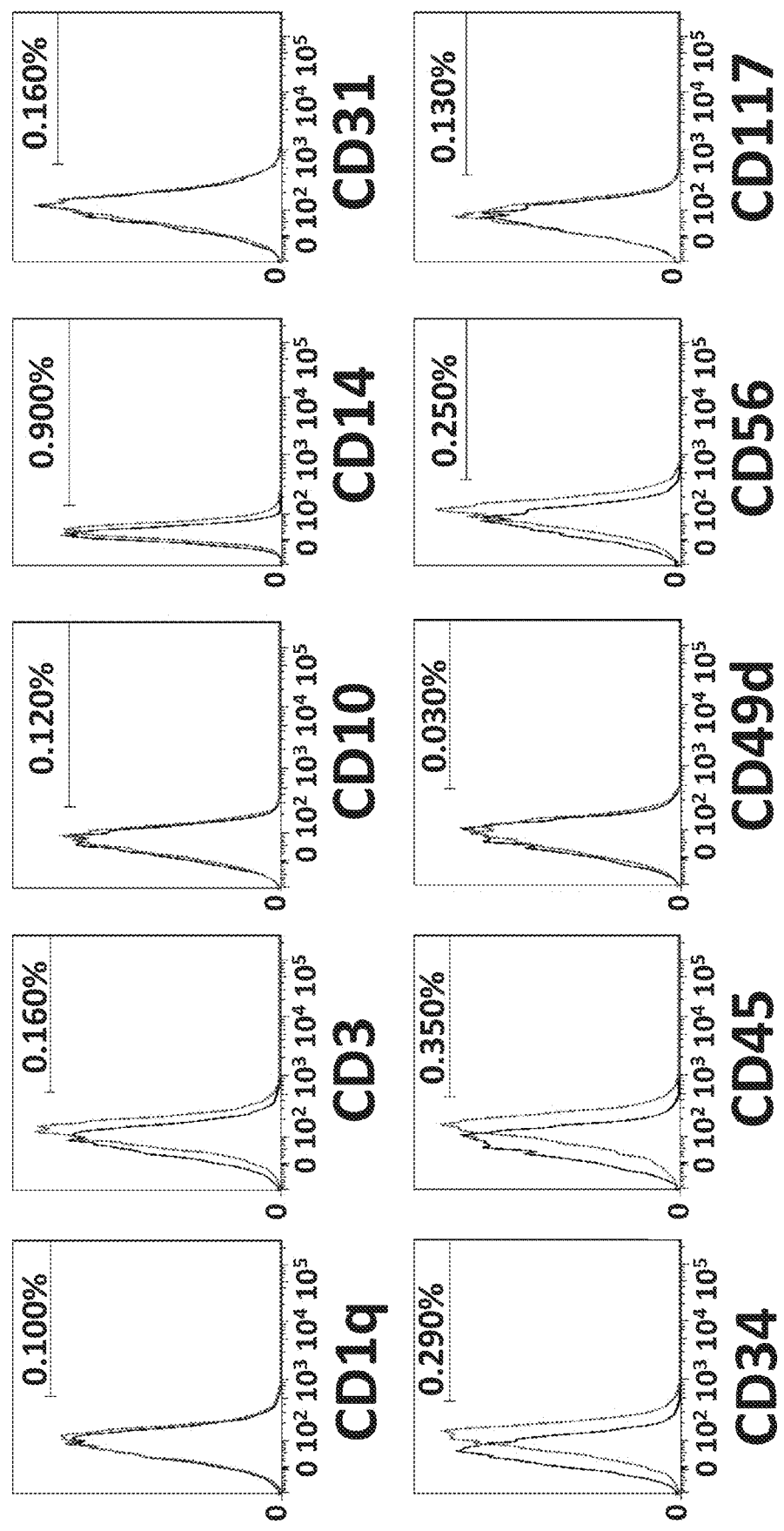

We prepared the primary cultures of umbilical cord mesenchymal stem cells (UMSCs) from Wharton's jelly (WJ) and analyzed the cell morphology and biological properties (FIG. 1A). The flow cytometry revealed that the cells were negative for CD1q, CD3, CD10, CD14, CD31, CD34, CD45, CD49d, CD56, CD117 and HLA-DR, but positive for CD13, CD29, CD44, CD73, CD90, CD105, CD166, CD49b and HLA-ABC (FIG. 1B). These observations indicate that UMSCs have the same surface markers as those of mesenchymal stem cells (MSCs), consistent with observations of bone marrow MSCs (J Cell Sci 2004, 117, 2971).

Figure 1C:
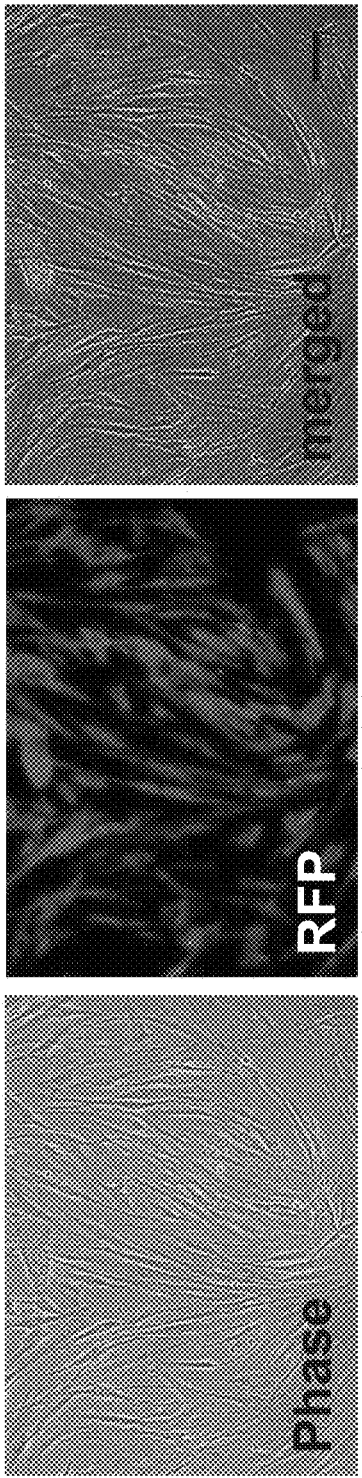
Figure 1C:
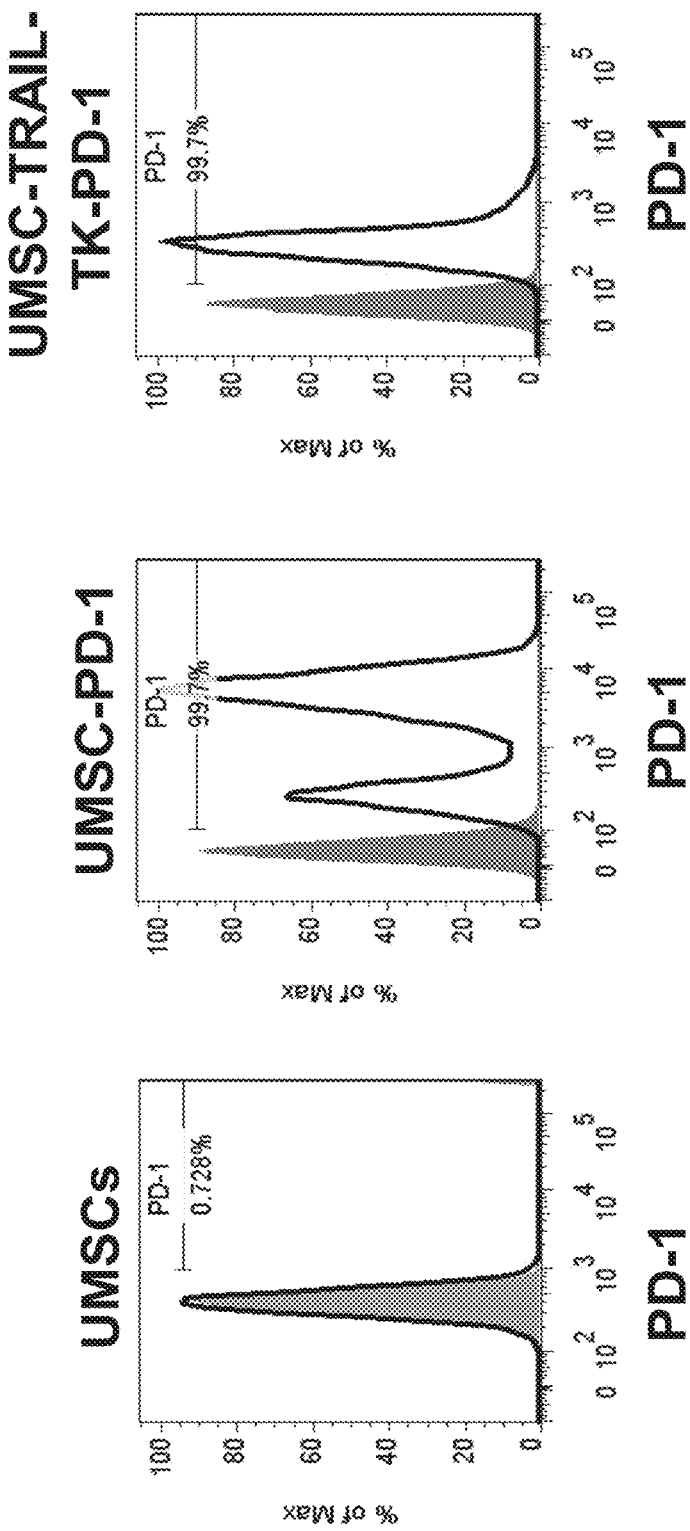

To evaluate the UMSCs transfection efficacy, the RFP fluorescence and PD-1 expression level of UMSC-TRAIL-TK-PD-1 were analyzed by flowcytometry study. At 36 h to 48 h after transfection, it demonstrated that the uptake efficacy was on average 55-65% via the results of RFP and PD-1 flowcytometry (FIG. 1C). Subsequently, after 3-5 days puromycin or G418 screening, over 90% of cells were fully transduced with the transgenes (FIG. 1C).

Figure 1D:
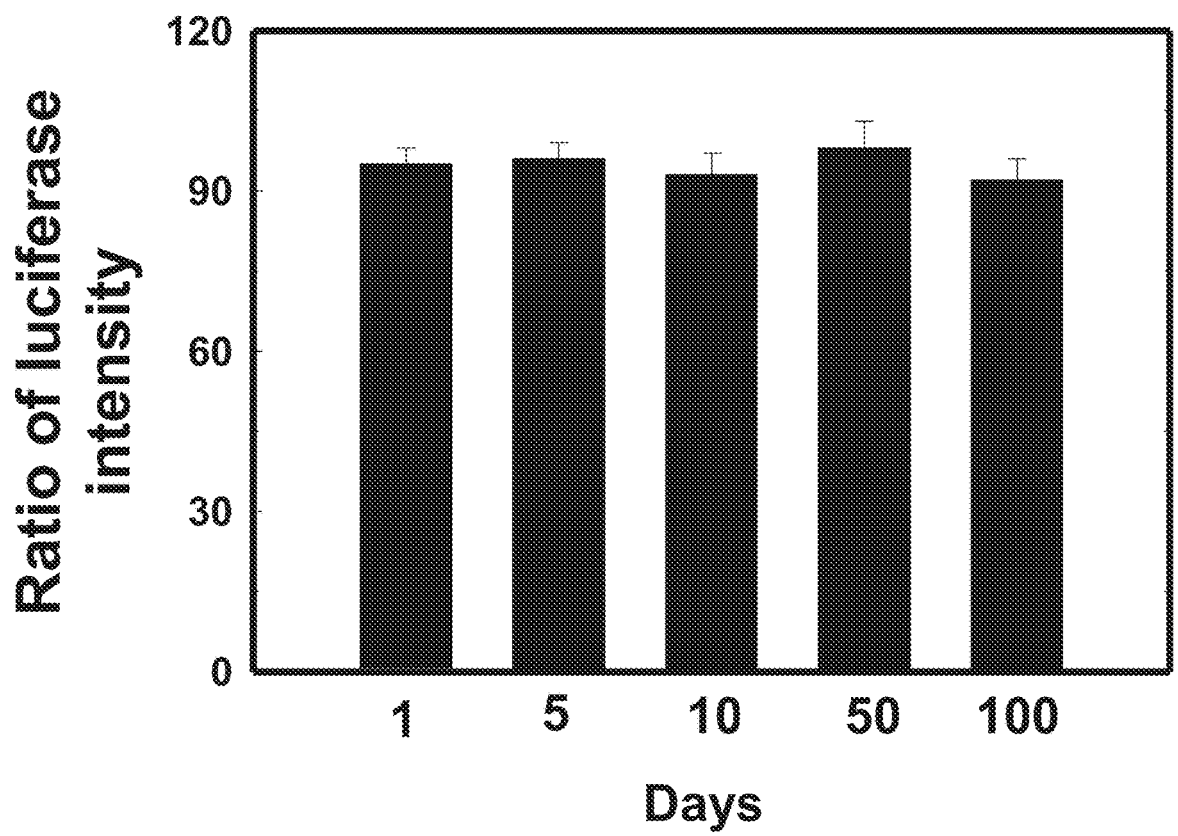

UMSC-TRAIL-TK-PD-1-Luc retained luciferase expression for over 100 days (FIG. 1D) and the cell viability by MTT assay, cell proliferation assay by BrdU incorporation and migration by transwell assay (FIG. 1E) revealed that pLAS3w-TRAIL-TK-PD-1 labeling did not affect the UMSC-TRAIL-TK-PD-1 cellular viability, cell proliferation or migration in vitro compared to unlabeled UMSCs after 14 h of incubation.

Figure 1F:
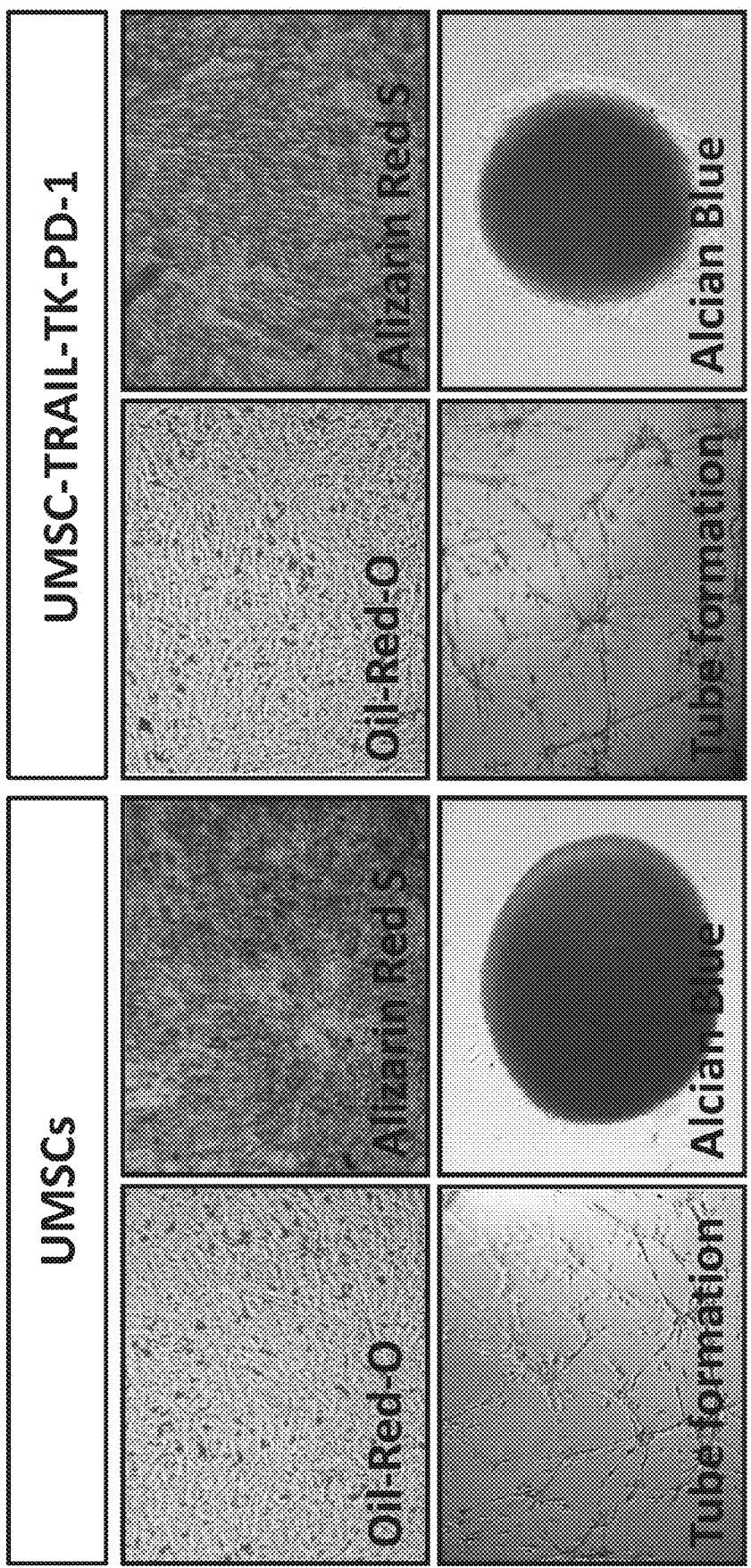
Figure 1G:
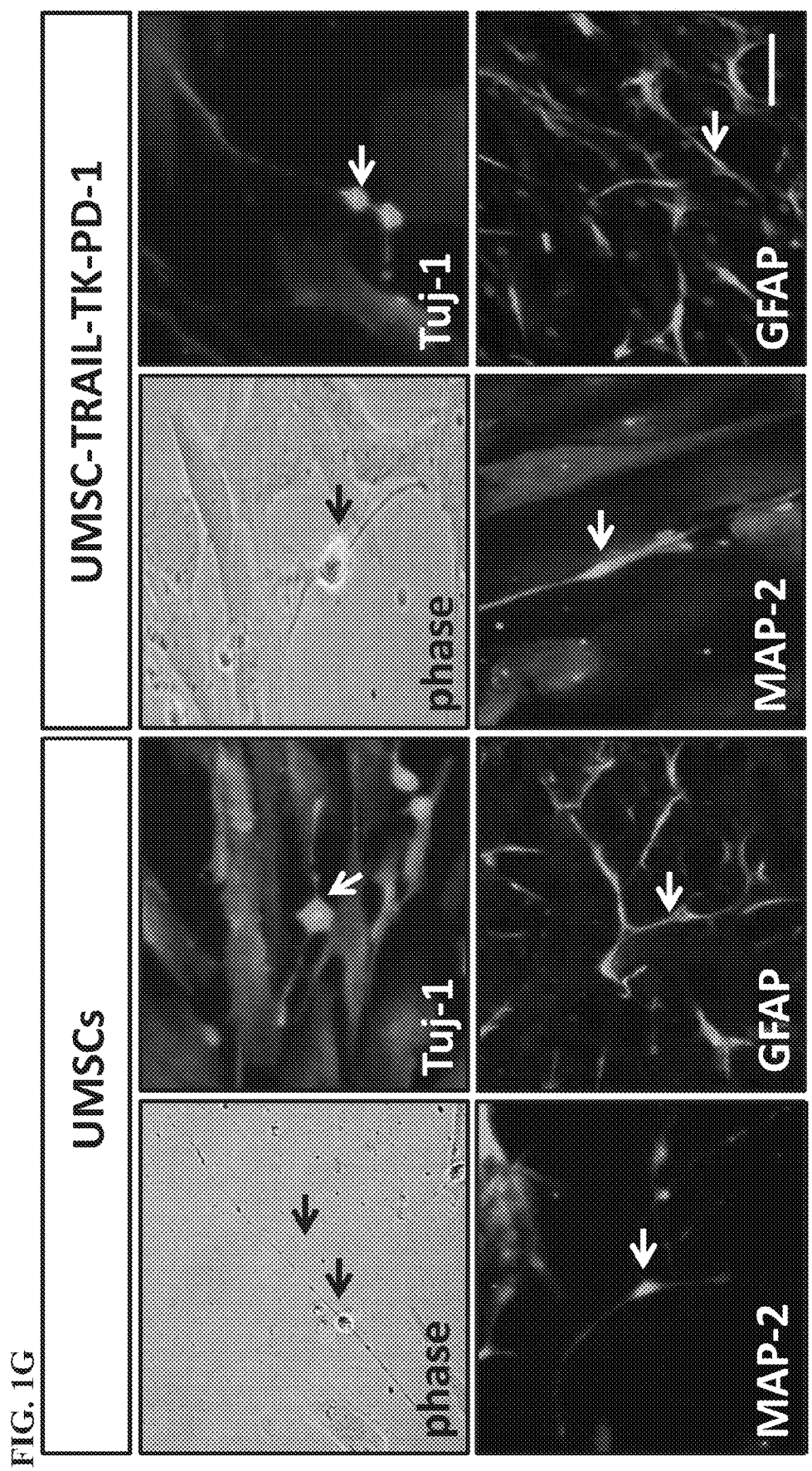

To demonstrate whether UMSC-TRAIL-TK-PD-1 still possessed multipotent differentiation potential, we analyzed the adipogenic, chondrogenic, osteogenic and vascular tube formation, which demonstrated that the UMSC-TRAIL-TK-PD-1 displayed similar behavior to the plain UMSCs without plasmid labeling (FIG. 1F). The UMSC-TRAIL-TK-PD-1's neuroglial cell differentiation was identified by immunofluorescence with MAP-2, Tuj-1 and GFAP and exhibited refractile cell body morphology with extended neurite-like structures arranged into a network as the plain UMSCs (FIG. 1G). Therefore, UMSC-TRAIL-TK-PD-1 did not lose cell differentiation potential in vitro.

Example 2

Specific Protein Binding of PD-L1 with UMSC-TRAIL-TK-PD-1 in Vitro

Figure 2A:
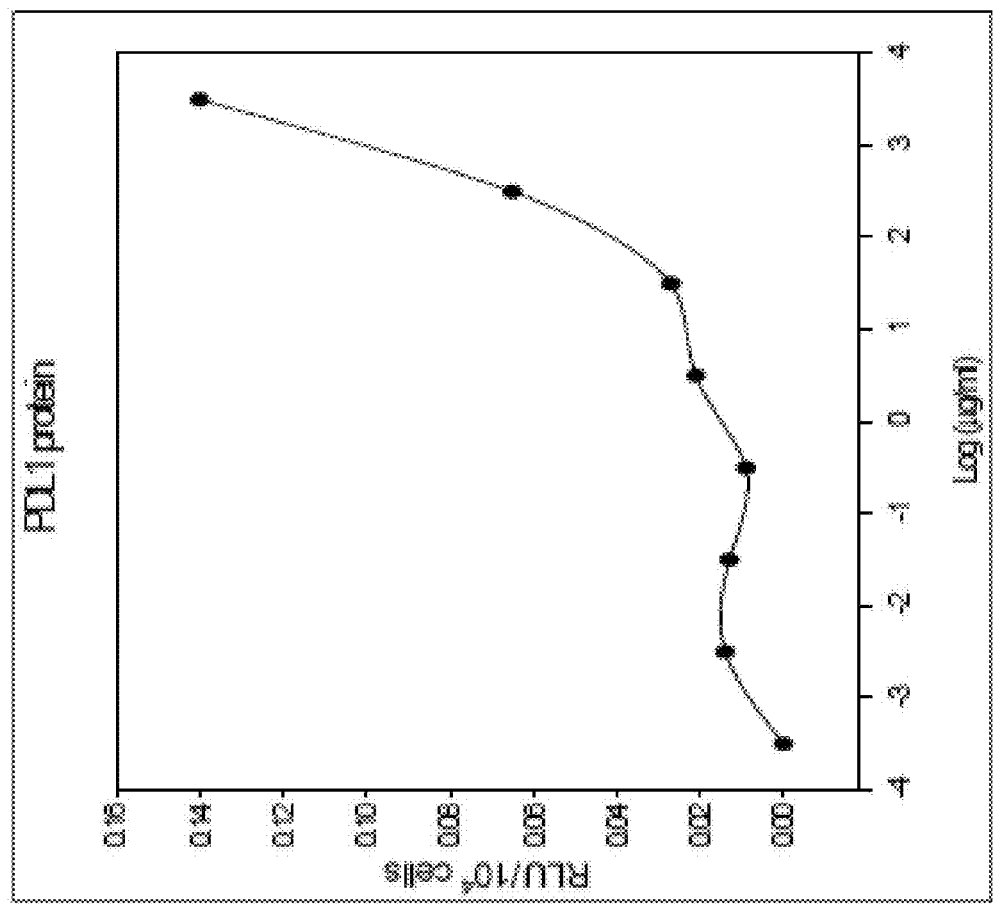

Since tumor cells express PD-L1 for the purpose of immune escape (Trends Immunol. 2006; 27:195-201), we established a gene-modified UMSCs of UMSC-TRAIL-TK-PD-1 in which presenting PD-1 could catch tumor cells by PD-1/PD-L1 interaction. To illustrate the protein-ligand binding affinity of UMSC-TRAIL-TK-PD-1, we analyzed the RLU of HRP-conjugated PD-1 protein at various concentrations by ELISA. The UMSC-TRAIL-TK-PD-1 was incubated with HRP-conjugated PD-L1 protein at 37° C. for 2 hours. The binding affinity of HRP-conjugated PD-1 protein increased significantly in a dose-dependent manner (FIG. 2A). The result indicates that UMSC-TRAIL-TK-PD-1 have high binding efficiency to PD-L1.

Example 3

In Vitro Activity of UMSC-TRAIL-TK-PD-1 in Human T Cells

To determine if the stimulatory effect was direct interaction between T cell and MSCs, splenocyte T cells were stimulated with CD3-CD28 beads. The gating strategy was based on the justification of first gate, exclusion of doublets by FSC-A and FSC-H, exclusion of dead cells by selection of $7-AAD^+$ (R&D systems)/$CD45^+$ or FSC-A depicted in FIG. 2B. T cells were labeled with CFSE and then co-cultured with either UMSCs or UMSC-TRAIL-TK-PD-1 stimulated with CD3-CD28 beads for 6 days. UMSCs (at a ratio of 1:1) significantly suppressed both $CD4^+$ and $CD8^+$ T-cell proliferation (FIG. 2C), but not at a ratio of 1:10. However, at either ratio of 1:1 or 1:10, UMSC-TRAIL-TK-PD-1 significantly increased both $CD4^+$ and $CD8^+$ T-cell proliferation (FIG. 2C). Moreover, UMSC-TRAIL-TK-PD-1 stimulated with CD3-CD28 beads significantly increased level of $CD4^+INF\text{-}\gamma^+$ and reduced $CD8^+CD122^+$ compared to UMSCs (FIG. 2D). These results suggest that either ratio of UMSC-TRAIL-TK-PD-1 can support T-cell proliferation, whereas higher ratios are inhibitory.

Example 4

Suicide Effect of UMSC-TRAIL-TK-PD-1 in Vitro

To investigate the thymidine kinase (TK)-induced cell killing effect in UMSC-TRAIL-TK-PD-1, suicide effect tested by evaluating the cell viability of UMSC-TRAIL-TK-PD-1 in the presence of various concentrations of GCV was performed. First, significantly increased level of TK was found in the UMSC-TRAIL-TK-PD-1 in a time- and dose-dependent manner (FIG. 3A). GCV itself did not affect cell proliferation of UMSCs (FIG. 3B). Phosphorylated GCV induced apoptotic-like cell injury in UMSC-TRAIL-TK-PD-1 after GCV treatment (FIG. 3B). The cell proliferation of UMSC-TRAIL-TK-PD-1 was inhibited in a dose-dependent manner (FIG. 3B). It indicates that the UMSC-TRAIL-TK-PD-1 could express TK after transfecting plasmid of TRAIL-TK-PD-1 and could activate GCV to its toxic form by inducing cytotoxicity on the UMSCs themselves.

Figure 3D:
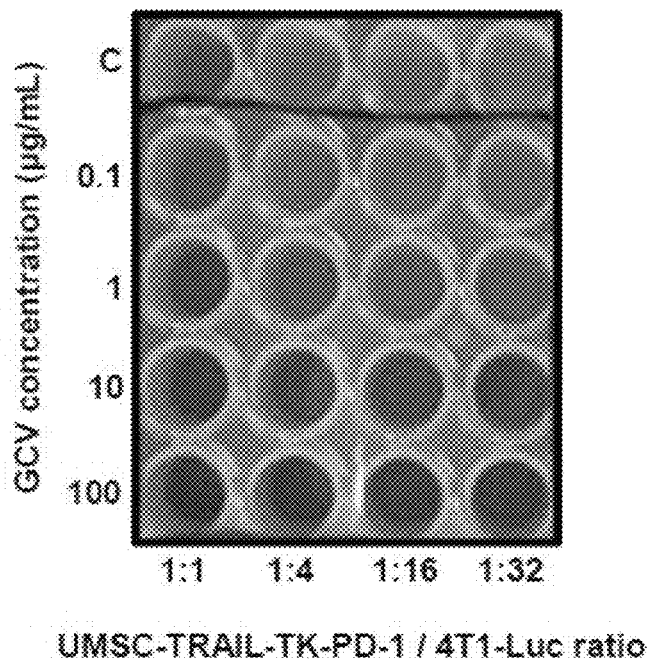
Figure 3D:
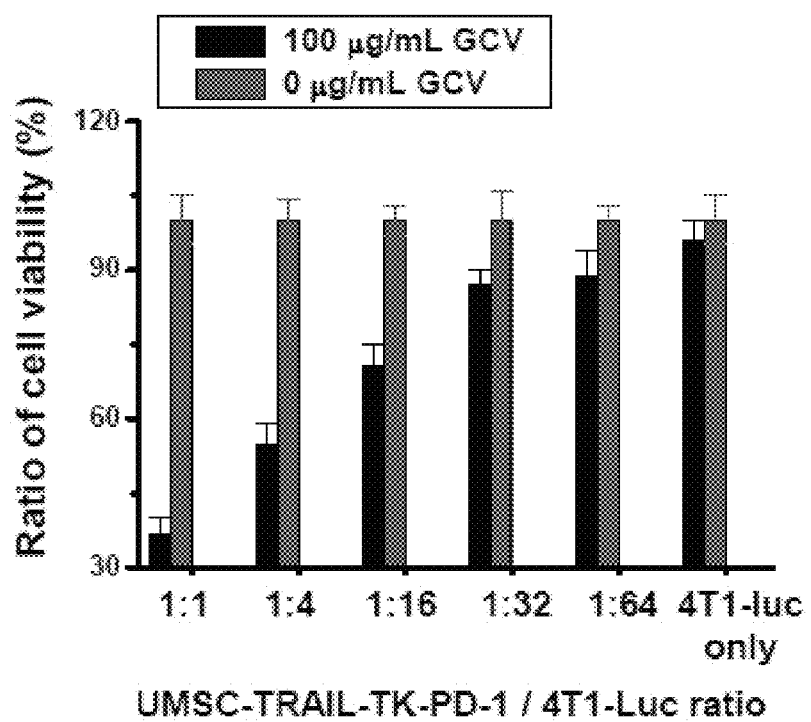

Sensitivity of tumor cells to the bystander effect of UMSC-TRAIL-TK-PD-1 in vitro To examine the bystander effect through UMSC-TRAIL-TK-PD-1, both 4T1 (Hep55.1C, Pan18, CT26) and UMSC-TRAIL-TK-PD-1 cell viability were evaluated by direct co-culture with different ratios of each cell in various concentrations of GCV (FIG. 3C). UMSC-TRAIL-TK-PD-1 could significantly attenuate the growth of 4T1-Luc cells (Hep55.1C, Pan18-Luc, CT26-Luc and GL261-Luc) (n=3) when the ratio was maximal on 1:32 and minimal on 1:1 with the presence of 100 μg/mL GCV after co-culturing for 7 days. Moreover, it demonstrated the best inhibition efficiency was at the ratio of 1:1 (FIG. 3D-E).

To further confirm the bystander effect of UMSC-TRAIL-TK-PD-1, the time course (before 7 days) of both the suicide effect and bystander effect of UMSC-TRAIL-TK-PD-1 were investigated. Cell mortality rate by suicide effect in this co-culture system slowly reached about one-third of the whole system during the first two days, and then subsequently accelerated from day 3 to day 6. In the bystander effect experiments, the same findings showed that most of 4T1-Luc cells were killed from day 3 to day 5 (FIG. 3C-E). Moreover, flowcytometric study also demonstrated that UMSC-TRAIL-TK-PD-1 cocultured with 4T1 cells significantly increased apoptotic cells ($PI^+Annexin-V^+$ cells) in a GCV dose-dependent manner (FIG. 3C). Therefore, the suicide effect of UMSC-TRAIL-TK-PD-1 and bystander effect on 4T1-Luc cells (Hep55.1C, Pan18-Luc, CT26-Luc and GL261-Luc) occurred from day 3 to day 5 in the co-culture system.

UMSC-TRAIL-TK-PD-1 expressing TRAIL displays an in vitro antitumor activity in 4T1-luc cell.

Figure 4A:
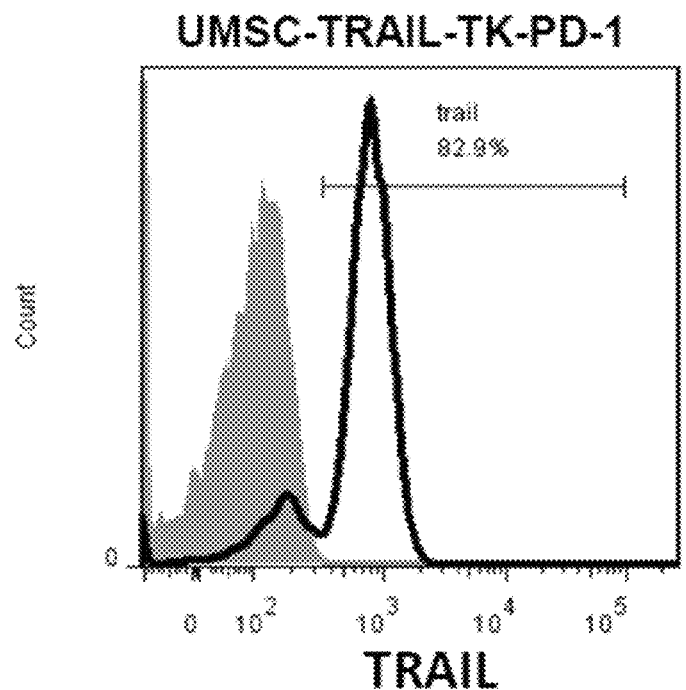
Figure 4A:
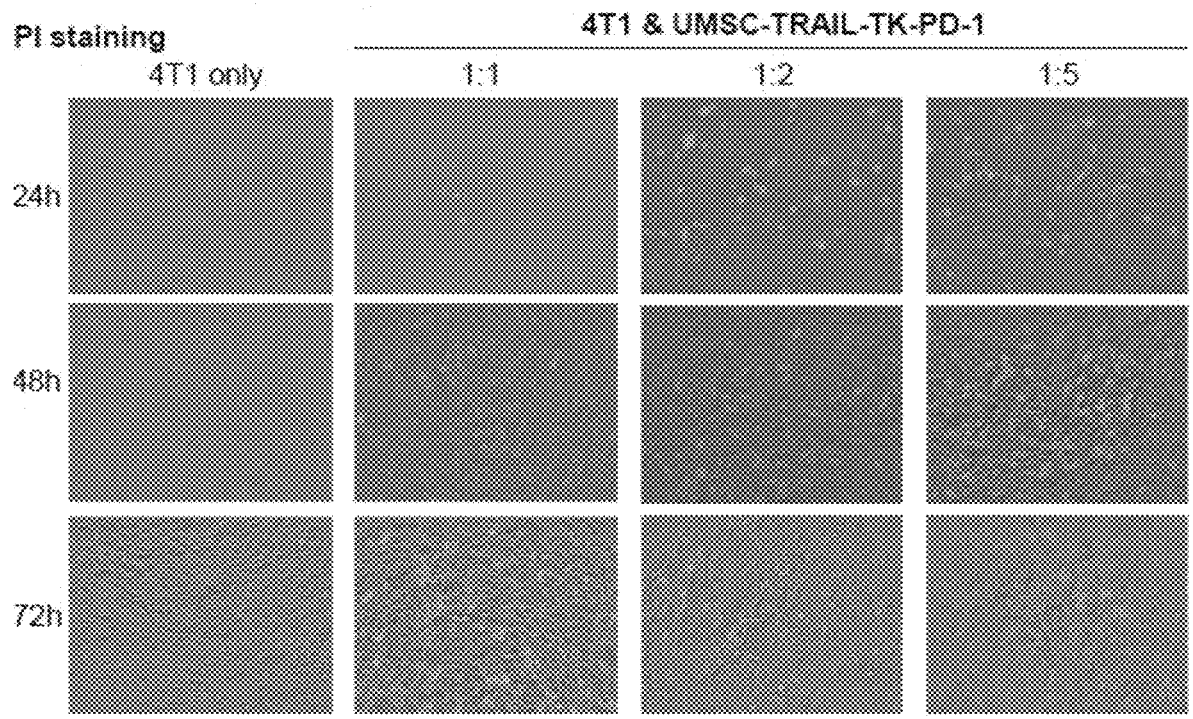

UMSC-TRAIL-TK-PD-1 can be genetically modified to express high levels of TRAIL. UMSC-TRAIL-TK-PD-1 was transduced by vector encoding for full-length human TRAIL. FACS analysis shows a relevant TRAIL protein expression (90%) on the cell surface of UMSCs (FIG. 4A).

To demonstrate whether the UMSC-TRAIL-TK-PD-1 could exert a tumoricidal effect on cancer cells, coculture experiments between tumor cells and UMSC-TRAIL-TK-PD-1 were then performed. UMSC-TRAIL-TK-PD-1 expressing TRAIL induces cells apoptosis (4T1-Luc, Hep55.1C-Luc), which was represented by cell shrinkage, reduction of adherent 4T1-Luc cells and Hep55.1C-Luc with the appearance of cellular debris, which were demonstrated by propidium iodine staining (PI staining), especially at 48 hours after coculture (FIG. 4B). To quantify cell death at 24, 48 and 72 hours, a large amount of Annexin-$V^+PI^+$ dead cells (≥70%) was detected in coculture where UMSC-TRAIL-TK-PD-1 are present in a dose-dependent manner as measured by FACS analysis (FIG. 4C).

Example 5

Tumor Targeting of UMSC-TRAIL-TK-PD-1-Luc in the 4T1 Tumor Model

Figure 5A:
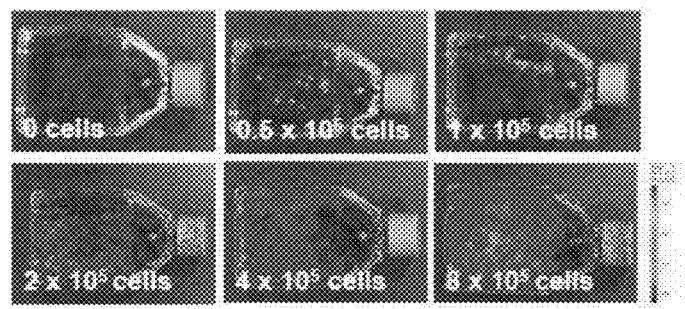
FIGS. 5A to G show tumor targeting of UMSC-TRAIL-TK-PD-1-Luc in the some tumors model.
Figure 5B:
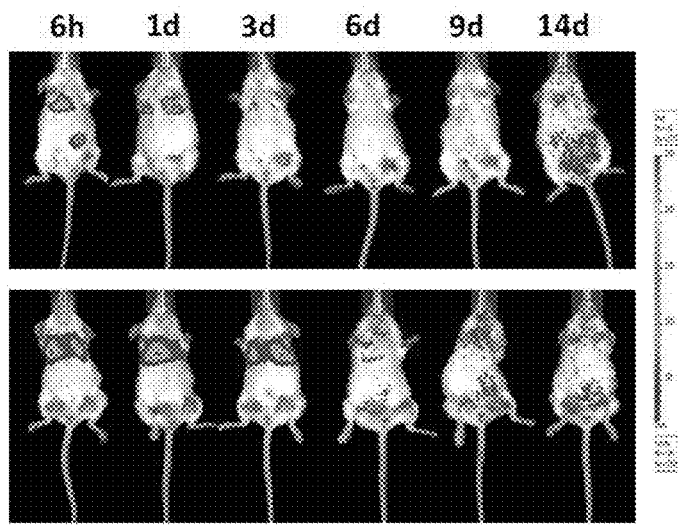

To demonstrate the UMSC-TRAIL-TK-PD-1 homing effect, biodistribution of UMSC-TRAIL-TK-PD-1-Luc after intravenous or intra-arterial implantation was performed using IVIS. First, bioilluminance intensity increased in a cell dose-dependent manner as measured by IVIS in vitro (FIG. 5A). In healthy mice, intravenous UMSC-TRAIL-TK-PD-1-Luc transplantation was initially entrapped in the lung capillary from one day after injection, which showed enhanced bioluminescent image of IVIS in lung (FIG. 5B). Homing of UMSC-TRAIL-TK-PD-1-Luc makes the UMSC-TRAIL-TK-PD-1-Luc survive and relocate to the subcutaneous 4T1 tumors. The bioluminescent signal of the subcutaneous tumor area in IVIS image was observed initially at five days after UMSC-TRAIL-TK-PD-1-Luc injection, gradually increased in intensity afterward, and peaked at day 14 (FIG. 5B).

Figure 5C:
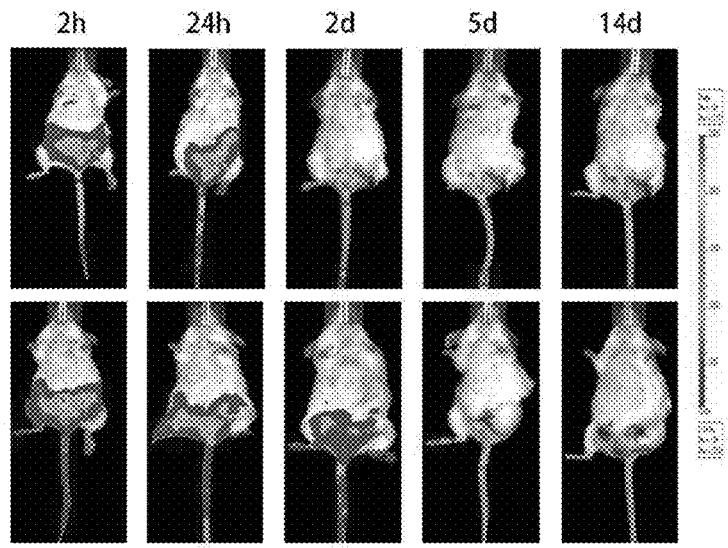
Figure 5D:
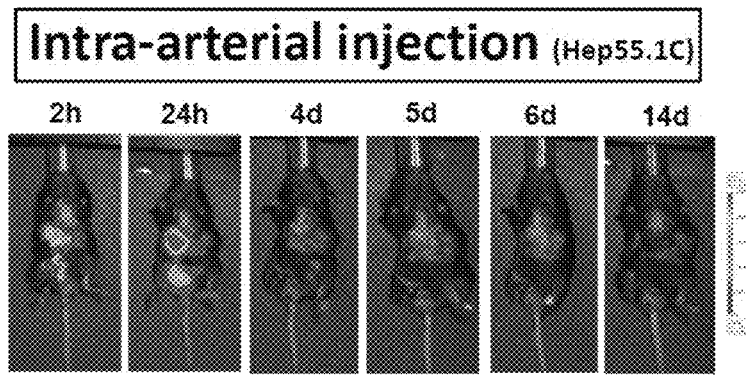
Figure 5E:
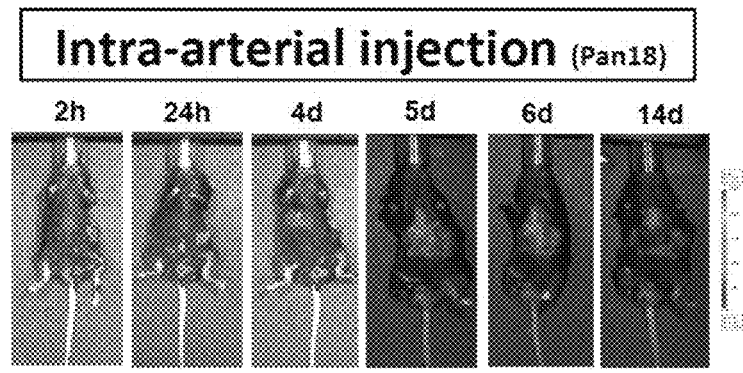

UMSC-TRAIL-TK-PD-1-Luc transplantation, was directly recruited to the orthotopic 4T1 tumor region (also for Hep55.1C and pan18 tumor region) two hours after intra-femoral artery injection without lung entrapment, which showed enhanced bioluminescent image of IVIS (FIG. 5C-E). Subsequently, homing of UMSC-TRAIL-TK-PD-1-Luc makes UMSC-TRAIL-TK-PD-1-Luc survive and relocate to the tumors sites.

Figure 5F:
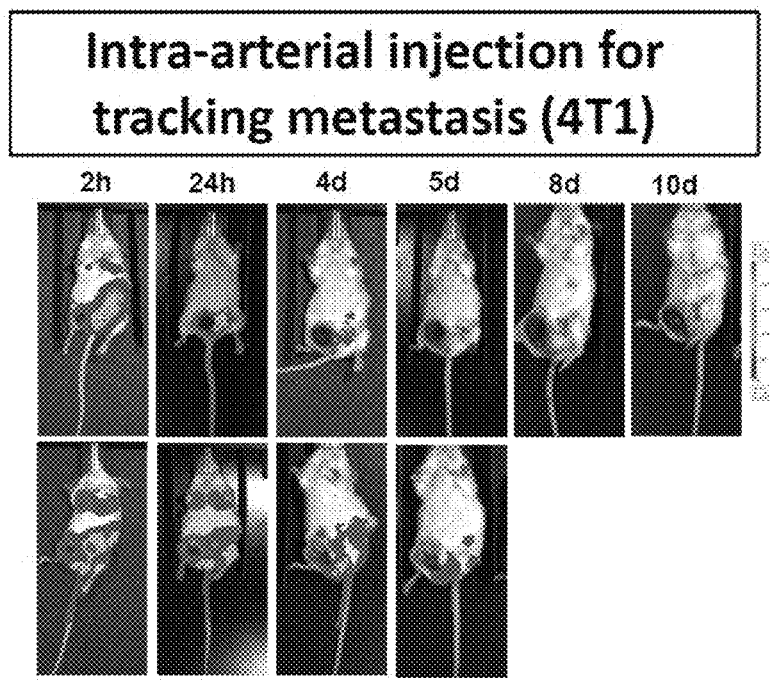
Figure 5G:
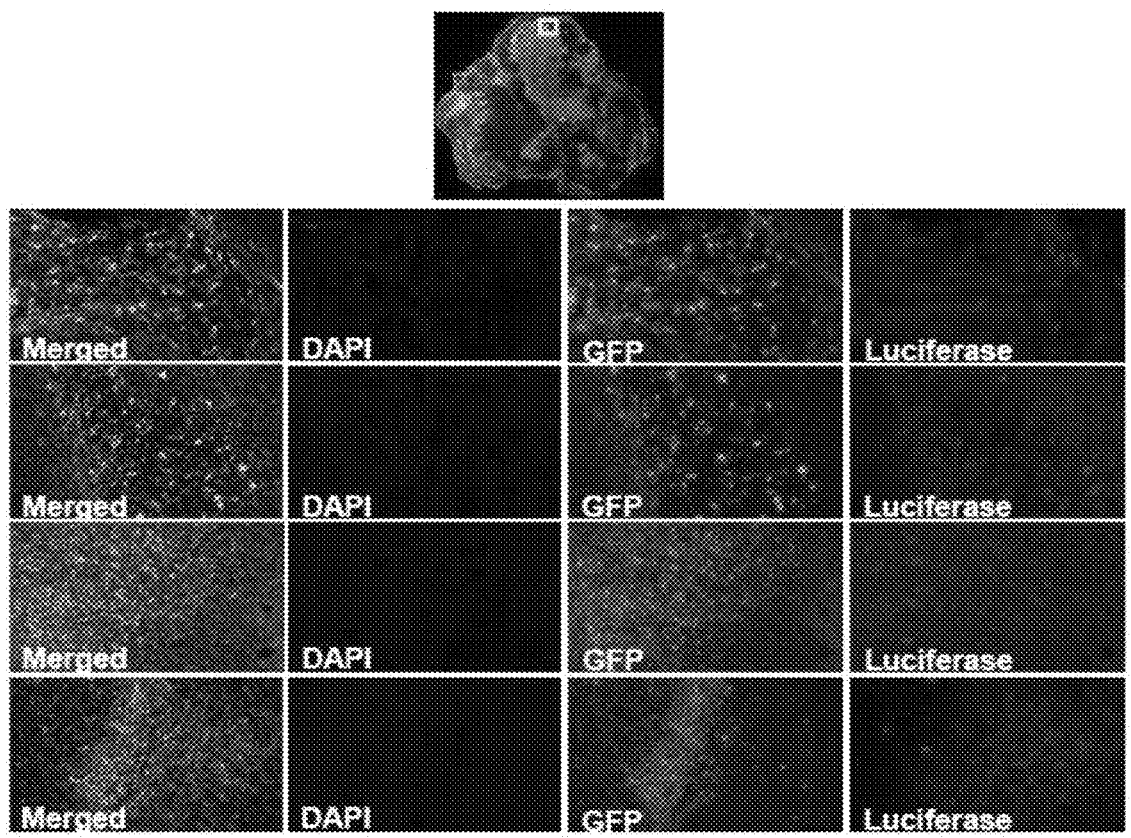

To further demonstrate whether UMSC-TRAIL-TK-PD-1-Luc could track the metastatic loci originating from 4T1-tumor model, intra-arterial implantation of UMSC-TRAIL-TK-PD-1-Luc was performed 21 days after induction of the 4T1-tumor model. Consistently, metastatic lung tumor from the original 4T1-tumor model significantly recruited the UMSC-TRAIL-TK-PD-1-Luc to increase the bioilluminance intensity as measured by IVIS in the multiple metastatic sites (FIG. 5F). Through immunohistochemical analysis, numerous $GFP^+Luciferase^+$ cells were found in the 4T1 tumor at one day after treatment, which indicated UMSC-TRAIL-TK-PD-1-GFP was recruited into the tumor microenvironment (FIG. 5G).

Example 6

Therapeutic Effect of UMSC-TRAIL-TK-PD-1 on 4T1-Luc Model

Figure 6A:
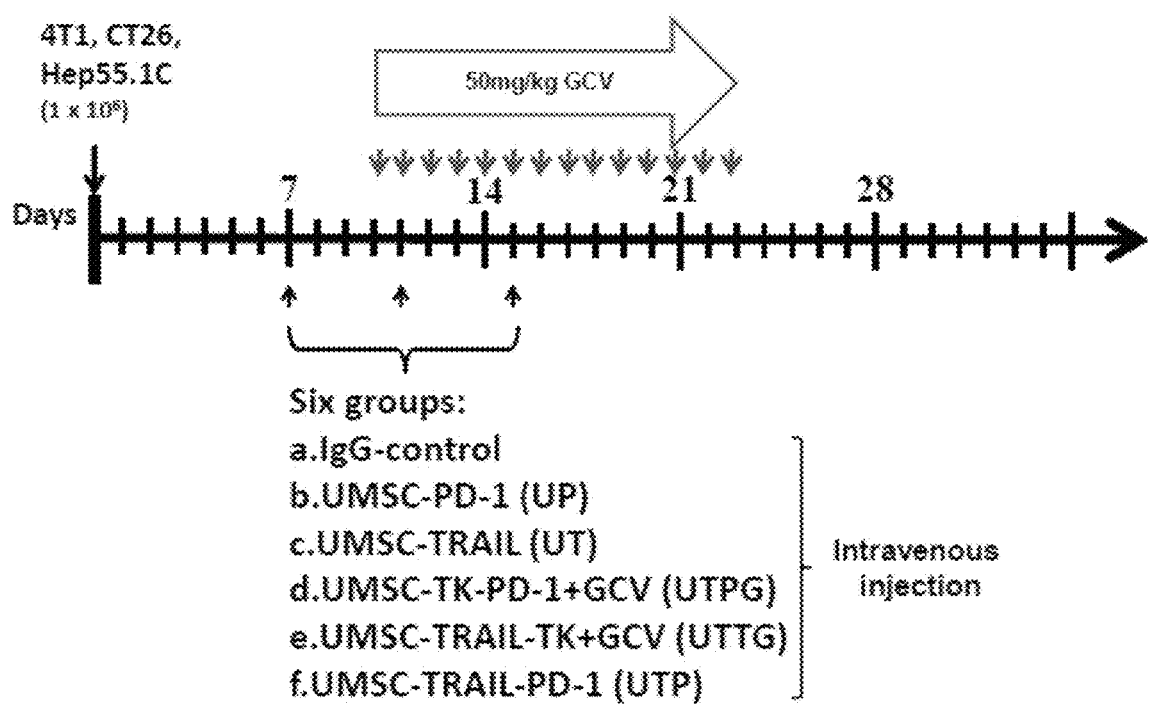
Figure 6B:
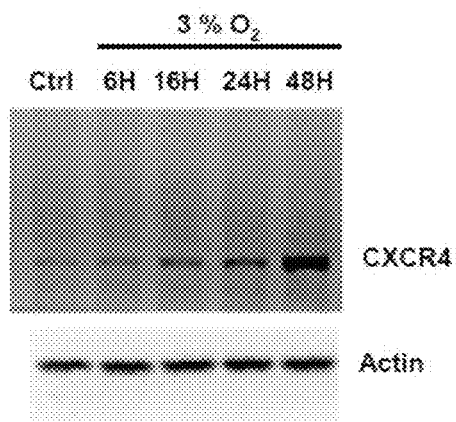
Figure 6C:
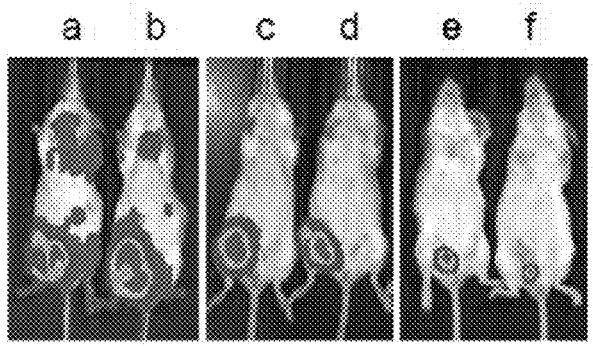
Figure 6C:
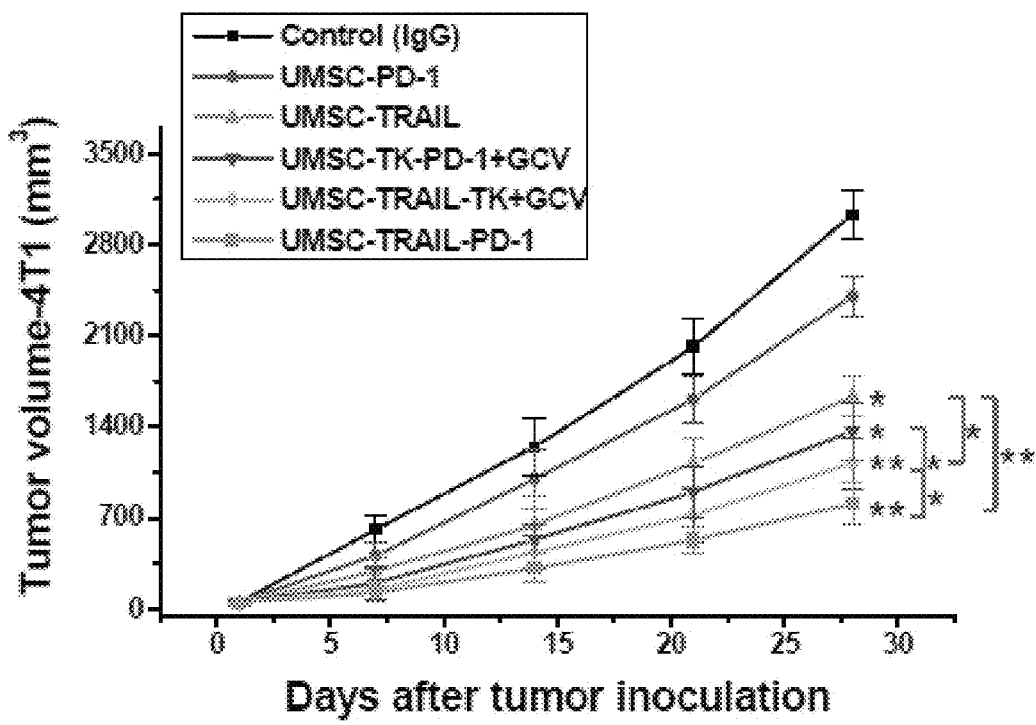
Figure 6E:
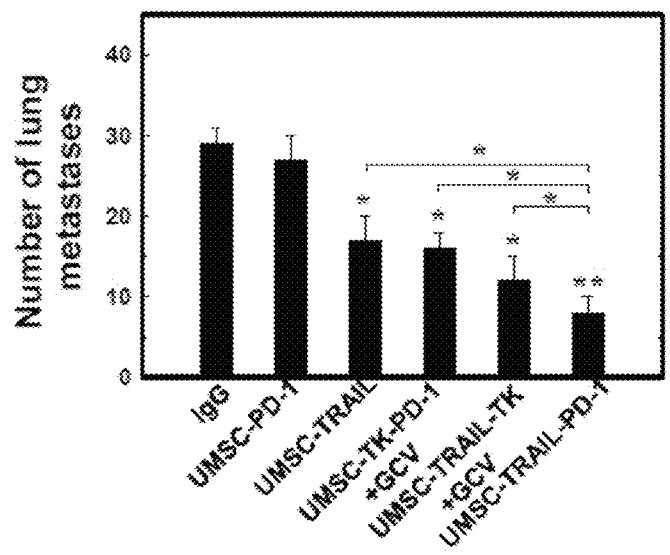
Figure 6E:
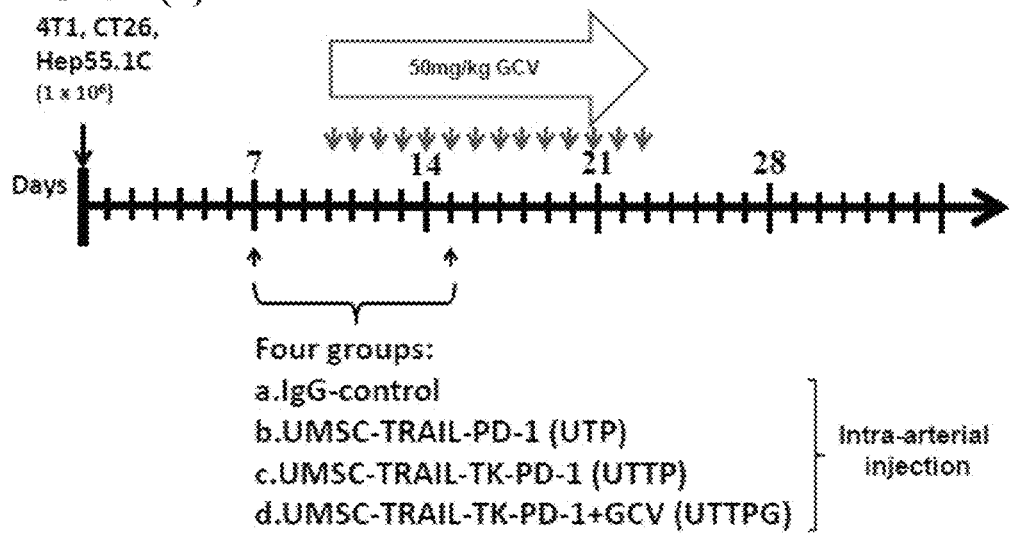
Figure 6E:
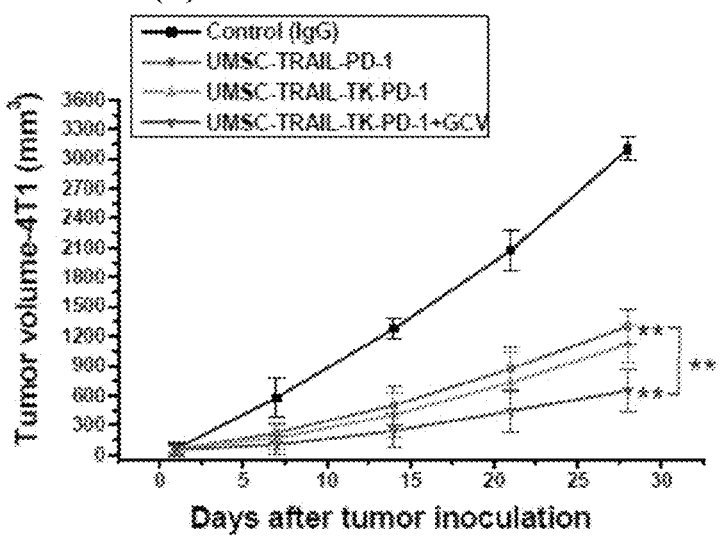

The tumoricidal effects in luciferase-expressing 4T1-Luc- and Hep55.1C-Luc-tumor-bearing mice treated with various strategies of gene modified UMSCs were assessed by IVIS, tumor volumes and survival time following the q4dx3 course of treatment protocol (FIG. 6A). Prior to treatment, every group of tested cells was subjected to hypoxia preconditioning culture in 3% $O_2$, which induced CXCR4 overexpression for enhancing stem cell homing in a time-dependent manner (FIG. 6B). Clearly, the UMSC-PD-1 (UP) group and UMSC-TRAIL (UT) group exhibited a therapeutic effect, reducing tumor volumes compared to those in the IgG control group as measured by IVIS (FIG. 6C). Moreover, the UMSC-TK-PD-1+GCV (UTPG) group, UMSC-TRAIL-TK+GCV (UTTG) group, and UMSC-TRAIL-PD-1 (UTP) group showed stronger antitumoral effects and each of them exhibited inhibition of tumor growth respectively (FIG. 6C). The median survival times of the mice treated with IgG, UP, UT, UTPG, UTTG, and UTP were 24, 32, 34, 34, 43, and 44 days, respectively (FIG. 6D). UTP significantly extended survival time to 63 days compared to the other groups (FIG. 6D). Furthermore, UTP significantly prevented tumor metastasis in lungs compared with other treatments (FIG. 6E). On average, fewer than 5 nodules of lung metastasis were discovered in UTP-treated mice compared to over 20 metastases in lungs of the control mice. However, UMSC-TK (UT), UP and UTP did not show a significant decrease in metastasis compared to the control group. As a result, we hypothesized that the metastasis was not only inhibited by UTP-induced bystander effect, but largely affected by the immune-enhancing effect from UTP in the TME, which led us to systemically analyze the intratumoral immunity.

Next, to verify whether intra-arterial injection of UMSC-TRAIL-TK-PD-1 displayed a significant therapeutic effect in 4T1-Luc and Hep55.1C-Luc model following the q7dx2 course of treatment protocol (FIG. 6F), four groups (UMSC-TK-PD-1+GCV (UTPG) group, UMSC-TRAIL-TK-PD-1 (UTTP) group, and UMSC-TRAIL-TK-PD-1+GCV (UTTPG) group) were examined the tumor growth and median survival time. Before the analysis of intra-arterial injection, intravenous administration of UMSC-TK-PD-1+GCV (UTPG) group, UMSC-TRAIL-TK-PD-1 (UTTP) group, and UMSC-TRAIL-TK-PD-1+GCV (UTTPG) group showed stronger antitumoral effects and exhibited inhibition of tumor growth respectively (FIG. 6F-G). Importantly, intra-arterial implantation revealed a robustly superior therapeutic effect to the intravenous ones. Moreover, the UTTPG group significantly inhibits tumor growth and enhances the median survival times of the mice than the other groups of IgG control, UTPG and UTTP in 4T1-Luc and Hep55.1C-Luc model, respectively (FIG. 6F-G). Unfortunately, administration of anti-PD-L1 did not show any significant therapeutic effect in 4T1-Luc and Hepa55.1C model (FIG. 6F-G).

Example 7

UTTPG Treatment Enhances Immunity in Tumor Microenvironment (TME)

Encouraged by the therapeutic outcomes, we evaluated the immunological properties of TME in 4T1 tumor model. Importantly, UTTPG could reverse the immune decline in the TME. There was an overall increase in the percentage of tumor-infiltrating $CD45^+$ leukocytes across the therapeutic groups of UTTPG and the other therapeutic groups (FIG. 7A). The results revealed that the frequencies for both $CD3^+CD8^+$ and $CD3^+CD4^+$ T cells were significantly enhanced in UTTPG treatment compared to the other groups (FIG. 7A). UTTPG also induced a significant reduction in Tregs (FIG. 7B), and thereby reversed the ratio of $CD8^+$ and $CD4^+$ T cells to Tregs within the tumors (FIG. 7C). Additionally, the number of TAMs dramatically decreased in response to UTTPG treatment (FIG. 7B), which increased the ratio of $CD8^+$ and $CD4^+$ T cells to TAMs in the TME (FIG. 7C). Of note, the marked upregulation in intracellular granzyme B ($Grb^+$) and $Ki67^+$ cells indicates that UTTPG treatment not only increased the antitumor immune population but also effectively achieved activation and proliferation of TILs (FIG. 7D).

What is claimed is:

1. An engineered stem cell, comprising a vector comprising a polynucleotide comprising a nucleic acid sequence of thymidine kinase (TK) gene, a nucleic acid sequence of programmed death receptor-1 (PD-1) gene, and a nucleic acid sequence of TNF-related apoptosis-inducing ligand (TRAIL) gene; wherein the stem cell is a tumor-targeting cell.

2. The engineered stem cell of claim 1, wherein the TK gene comprises a sequence as set forth in SEQ ID NO:1 or 2.

3. The engineered stem cell of claim 1, wherein the PD-1 gene has a sequence as set forth in SEQ ID NO:3.

4. The engineered stem cell of claim 1, wherein the TRAIL comprises a sequence as set forth in SEQ ID NO:5.

5. The engineered stem cell of claim 1, wherein the stem cell is selected from the group consisting of: embryonic stem cell, marrow stromal cell (MSC), hematopoietic stem cell and neural stem cell.

6. A combination comprising an engineered stem cell of claim 1 and an additional active agent.

7. A method for treating a cancer or enhancing intratumor immunity in a subject in need thereof, comprising administering an effective amount of a combination of claim 6 to the subject.

8. The method of claim 7, wherein the engineered stem cell and the additional active agent are administered separately, simultaneously or concurrently.

9. A method for treating a cancer or enhancing intratumor immunity in a subject in need thereof, comprising administering an effective amount of an engineered stem cell of claim 1 to the subject.

10. The method of claim 9, wherein the cancer is breast cancer, colon cancer, rectal cancer, lung cancer, ovarian cancer, prostate cancer, skin cancer, brain cancer, bladder cancer, endometrial cancer, kidney cancer, pancreatic cancer, thyroid cancer, melanoma, leukemia, fibrosarcoma, sarcoma, adenocarcinoma, or glioma.

11. The method of claim 9, wherein the effective amount ranges from 100,000 ($1 \times 10^5$) 2,000,000 ($2 \times 10^6$) cells.

12. The method of claim 9, wherein the engineered stem cell of claim 1 can be intravenously or intra-arterially administered to the subject, optionally in combination with an additional active agent.

13. The method of claim 12, wherein the additional active agent is ganciclovir (GCV).

14. The method of claim 9, wherein the method enhances immunity in tumor microenvironment through an increase in tumor-specific CD8$^+$IFN-γ$^+$CD44$^+$ T cells with central memory potential.

15. The method of claim 9, wherein the method induces a significant reduction in Tregs, and thereby reverses the ratio of CD8+ and CD4+ T cells to Tregs within the tumors.

16. The method of claim 9, wherein the method decreases the number of TAMs, which increases the ratio of CD8+ and CD4+ T cells to TAMs in the TME.

* * * * *